(12) United States Patent
Minvielle

(10) Patent No.: US 9,429,920 B2
(45) Date of Patent: Aug. 30, 2016

(54) INSTRUCTIONS FOR CONDITIONING NUTRITIONAL SUBSTANCES

(71) Applicant: Eugenio Minvielle, Rye, NY (US)

(72) Inventor: Eugenio Minvielle, Rye, NY (US)

( * ) Notice: Subject to any disclaimer, the term of this patent is extended or adjusted under 35 U.S.C. 154(b) by 0 days.

(21) Appl. No.: 14/467,433

(22) Filed: Aug. 25, 2014

(65) Prior Publication Data

US 2014/0364972 A1   Dec. 11, 2014

Related U.S. Application Data

(63) Continuation-in-part of application No. 14/074,664, filed on Nov. 7, 2013, now Pat. No. 8,851,365, which is a continuation-in-part of application No. 14/044,851, filed on Oct. 2, 2013, now Pat. No.

(Continued)

(51) Int. Cl.
*G06F 17/00* (2006.01)
*G05B 13/02* (2006.01)
(Continued)

(52) U.S. Cl.
CPC .............. *G05B 13/02* (2013.01); *A23P 1/00* (2013.01); *G01N 33/0001* (2013.01); *G01N 33/02* (2013.01); *G06F 17/30386* (2013.01); *G06Q 10/06* (2013.01); *G06Q 30/0207* (2013.01); *G09B 19/0092* (2013.01); *G06F 19/322* (2013.01)

(58) Field of Classification Search
CPC . G09B 19/0092; A23P 1/00; G01N 33/0001; G01N 33/02; G06F 19/3475; G06F 17/30; G06F 19/322; G06F 19/3406; G06F 19/3418; G06F 19/3481; G06F 19/3487; G06F 17/3061; G06F 19/30; G06F 19/3412; A61B 5/411; A61B 2560/0209; A61B 2560/0295; A61B 2560/0456; A61B 2562/0219; A61B 5/002; A61B 5/0022; A61B 5/0077; A61B 5/01; A61B 5/02055; A61B 5/02405; A61B 5/0533; A61B 5/11; A61B 5/1112; A61F 13/42; A61F 2007/0002; A61F 2007/0056; A61F 2007/0075; A61F 2007/009; A61F 2007/0093; A61F 2007/029; A61F 2007/101; A61F 2007/126; A61F 5/48; A61F 7/106; A61F 7/12
USPC ................ 235/375, 383, 381, 492, 486, 487
See application file for complete search history.

(56) References Cited

U.S. PATENT DOCUMENTS 3,685,308 A   8/1972   Lundquist
4,225,410 A   9/1980   Pace
(Continued)

FOREIGN PATENT DOCUMENTS

CN   101173316      5/2008
CN   102033043 A    4/2011
(Continued)

OTHER PUBLICATIONS

Office Action in U.S. Appl. No. 13/485,850, mailed Sep. 29, 2014.
(Continued)

*Primary Examiner* — Thien M Le
(74) *Attorney, Agent, or Firm* — Nixon Peabody LLP

(57) ABSTRACT

Nutritional substance systems and methods are disclosed enabling the tracking and communication of changes in nutritional, organoleptic, and aesthetic values of nutritional substances, and further enabling the adaptive storage and adaptive conditioning of nutritional substances.

27 Claims, 19 Drawing Sheets

Related U.S. Application Data 9,080,997, which is a continuation-in-part of application No. 13/931,733, filed on Jun. 28, 2013, now Pat. No. 9,171,061, which is a continuation-in-part of application No. 13/560,965, filed on Jul. 27, 2012, now Pat. No. 8,490,862, which is a continuation of application No. 13/485,863, filed on May 31, 2012, which is a continuation-in-part of application No. 13/602,040, filed on Aug. 31, 2012, which is a continuation of application No. 13/485,866, filed on May 31, 2012, which is a continuation-in-part of application No. 13/684,113, filed on Nov. 21, 2012.

(60) Provisional application No. 61/625,002, filed on Apr. 16, 2012, provisional application No. 61/625,010, filed on Apr. 16, 2012, provisional application No. 61/624,745, filed on Apr. 16, 2012, provisional application No. 61/624,765, filed on Apr. 16, 2012, provisional application No. 61/624,788, filed on Apr. 16, 2012, provisional application No. 61/624,992, filed on Apr. 16, 2012.

(51) Int. Cl.
| | |
|---|---|
| *A23P 1/00* | (2006.01) |
| *G01N 33/00* | (2006.01) |
| *G01N 33/02* | (2006.01) |
| *G06Q 10/06* | (2012.01) |
| *G09B 19/00* | (2006.01) |
| *G06F 17/30* | (2006.01) |
| *G06Q 30/02* | (2012.01) |
| *G06F 19/00* | (2011.01) |

(56) References Cited

U.S. PATENT DOCUMENTS

| | | | |
|---|---|---|---|
| 4,364,234 A | 12/1982 | Reed | |
| 4,555,930 A | 12/1985 | Leach et al. | |
| 4,644,137 A | 2/1987 | Asahi et al. | |
| 4,644,154 A | 2/1987 | Brogardh et al. | |
| 4,650,766 A | 3/1987 | Harm et al. | |
| 4,674,320 A | 6/1987 | Hirschfeld | |
| 4,777,599 A | 10/1988 | Dorogi et al. | |
| 4,837,035 A | 6/1989 | Baker et al. | |
| 4,874,928 A | 10/1989 | Kasai | |
| 5,034,242 A | 7/1991 | Lasdon et al. | |
| 5,062,066 A | 10/1991 | Scher et al. | |
| D333,782 S | 3/1993 | van Berlo | |
| 5,250,789 A | 10/1993 | Johnsen | |
| 5,361,681 A | 11/1994 | Hedström | |
| 5,412,560 A | 5/1995 | Dennision | |
| 5,442,669 A | 8/1995 | Medin | |
| 5,478,900 A | 12/1995 | Amano et al. | |
| 5,478,989 A | 12/1995 | Shepley | |
| 5,478,990 A | 12/1995 | Montanari et al. | |
| 5,483,799 A | 1/1996 | Dalto | |
| 5,496,576 A | 3/1996 | Jeong | |
| 5,558,797 A | 9/1996 | Takagi | |
| 5,673,691 A | 10/1997 | Abrams et al. | |
| 5,697,177 A | 12/1997 | Ludlow et al. | |
| 5,804,803 A | 9/1998 | Cragun et al. | |
| 5,853,790 A | 12/1998 | Glancy | |
| 5,872,721 A | 2/1999 | Huston et al. | |
| 5,954,640 A | 9/1999 | Szabo | |
| 6,012,415 A | 1/2000 | Linseth | |
| 6,080,972 A * | 6/2000 | May | A21B 1/02 219/486 |
| 6,119,531 A | 9/2000 | Wendte et al. | |
| 6,157,306 A | 12/2000 | Mularoni | |
| 6,182,725 B1 | 2/2001 | Sorvik | |
| 6,211,789 B1 | 4/2001 | Oldham et al. | |
| 6,270,724 B1 | 8/2001 | Woodaman | |
| 6,276,264 B1 | 8/2001 | Dumm | |
| 6,285,282 B1 | 9/2001 | Dorenbosch et al. | |
| 6,299,920 B1 | 10/2001 | Saksena | |
| 6,299,921 B1 | 10/2001 | Loffler et al. | |
| 6,310,964 B1 | 10/2001 | Mohan et al. | |
| 6,325,878 B1 | 12/2001 | Borgstrom | |
| 6,356,940 B1 | 3/2002 | Short | |
| 6,375,077 B1 | 4/2002 | Hankins | |
| 6,387,049 B1 | 5/2002 | Moore | |
| 6,444,233 B1 | 9/2002 | Arntzen et al. | |
| 6,483,434 B1 | 11/2002 | UmiKer | |
| 6,491,217 B2 | 12/2002 | Catan | |
| 6,502,411 B2 | 1/2003 | Okamoto | |
| 6,512,919 B2 | 1/2003 | Ogasawara | |
| 6,513,532 B2 | 2/2003 | Mault et al. | |
| 6,538,215 B2 | 3/2003 | Montagnino et al. | |
| 6,549,818 B1 | 4/2003 | Ali | |
| 6,553,386 B1 | 4/2003 | Alabaster | |
| 6,554,182 B1 | 4/2003 | Magnusson et al. | |
| 6,556,963 B1 | 4/2003 | Tetzlaff | |
| 6,571,603 B1 | 6/2003 | Doleman et al. | |
| D478,773 S | 8/2003 | Palen | |
| 6,616,047 B2 | 9/2003 | Catan | |
| 6,631,333 B1 | 10/2003 | Lewis et al. | |
| 6,671,698 B2 | 12/2003 | Pickett et al. | |
| 6,676,014 B2 | 1/2004 | Catan | |
| 6,689,398 B2 | 2/2004 | Haridas et al. | |
| 6,691,135 B2 | 2/2004 | Wagner et al. | |
| 6,716,462 B2 | 4/2004 | Prosise et al. | |
| 6,773,926 B1 | 8/2004 | Freund et al. | |
| 6,789,021 B2 | 9/2004 | Rendahl et al. | |
| 6,809,301 B1 * | 10/2004 | McIntyre | F24C 7/082 219/492 |
| 6,844,197 B1 | 1/2005 | Doleman et al. | |
| 6,874,000 B2 | 3/2005 | Sholl et al. | |
| 6,888,458 B2 | 5/2005 | Carlson | |
| 6,953,342 B2 | 10/2005 | Bisogno | |
| 6,953,919 B2 | 10/2005 | Clothier | |
| 6,975,910 B1 | 12/2005 | Brown et al. | |
| 6,982,640 B2 | 1/2006 | Lindsay et al. | |
| 7,024,369 B1 | 4/2006 | Brown et al. | |
| 7,076,438 B1 | 7/2006 | Tobelmann et al. | |
| 7,080,593 B1 | 7/2006 | Frankel | |
| 7,085,777 B2 | 8/2006 | Beck et al. | |
| 7,090,638 B2 | 8/2006 | Vidgen | |
| 7,103,481 B2 | 9/2006 | Negri | |
| 7,151,447 B1 | 12/2006 | Willms et al. | |
| 7,152,040 B1 | 12/2006 | Hawthorne et al. | |
| D534,758 S | 1/2007 | Lee et al. | |
| D539,072 S | 3/2007 | Kawata et al. | |
| D539,595 S | 4/2007 | Okuda et al. | |
| D540,613 S | 4/2007 | Jeon | |
| D541,578 S | 5/2007 | Jeon | |
| 7,212,955 B2 | 5/2007 | Kirshenbau et al. | |
| 7,213,743 B2 | 5/2007 | Carlson et al. | |
| 7,215,420 B2 | 5/2007 | Gellerman et al. | |
| 7,237,400 B2 | 7/2007 | Owada | |
| 7,256,699 B2 | 8/2007 | Tethrake et al. | |
| 7,275,863 B1 | 10/2007 | Akers et al. | |
| 7,295,889 B2 | 11/2007 | Lahteenmaki | |
| D560,960 S | 2/2008 | Hillmann et al. | |
| 7,349,857 B2 | 3/2008 | Manzo | |
| 7,357,316 B2 | 4/2008 | Heckel et al. | |
| 7,359,802 B1 | 4/2008 | Lewis et al. | |
| 7,372,003 B2 | 5/2008 | Kates | |
| 7,396,550 B2 * | 7/2008 | Angel | 426/96 |
| 7,403,855 B2 | 7/2008 | Fuessley et al. | |
| 7,440,901 B1 | 10/2008 | Dlott et al. | |
| 7,445,372 B1 | 11/2008 | Engel et al. | |
| 7,474,965 B2 | 1/2009 | Johnson et al. | |
| 7,509,839 B2 | 3/2009 | Duranton | |
| 7,532,106 B2 | 5/2009 | Debord et al. | |
| 7,571,676 B2 | 8/2009 | Nelson et al. | |
| 7,620,531 B1 | 11/2009 | Johnson | |
| D607,264 S | 1/2010 | Lee | |
| 7,681,383 B2 | 3/2010 | Argetsinger et al. | |
| D618,488 S | 6/2010 | Knochner | |
| 7,743,591 B2 | 6/2010 | Meier et al. | |
| 7,797,204 B2 | 9/2010 | Balent | |

(56) References Cited

U.S. PATENT DOCUMENTS

| | | | |
|---|---|---|---|
| 7,809,601 B2 | 10/2010 | Shaya et al. | |
| 7,836,876 B2 | 11/2010 | Schellenberg | |
| 7,840,359 B2 | 11/2010 | Hsiung et al. | |
| 7,854,108 B2 | 12/2010 | Koselka et al. | |
| D633,326 S | 3/2011 | Shin et al. | |
| 7,933,733 B2 | 4/2011 | Ashrafzadeh et al. | |
| 7,942,867 B2 | 5/2011 | Hood et al. | |
| 7,951,079 B1 | 5/2011 | Moore | |
| 7,957,850 B2 | 6/2011 | Anderson | |
| 7,996,134 B2 | 8/2011 | Roberts | |
| 8,009,048 B2 | 8/2011 | Hyde et al. | |
| 8,033,237 B2 | 10/2011 | Havens et al. | |
| 8,082,809 B2 | 12/2011 | Luellen et al. | |
| D654,299 S | 2/2012 | Benold | |
| 8,112,303 B2 | 2/2012 | Eglen et al. | |
| D657,607 S | 4/2012 | Ohmae et al. | |
| 8,147,888 B2 | 4/2012 | Kling et al. | |
| 8,173,188 B2 | 5/2012 | Suetsugu | |
| 8,193,474 B2 | 6/2012 | Harris | |
| D665,220 S | 8/2012 | Ohmae et al. | |
| 8,265,957 B2 | 9/2012 | Craine | |
| 8,285,593 B2 | 10/2012 | Bhatt et al. | |
| 8,314,701 B2 | 11/2012 | Grieco et al. | |
| D673,001 S | 12/2012 | Becze et al. | |
| 8,393,137 B1 | 3/2013 | Crosby | |
| 8,403,215 B2 | 3/2013 | Aihara et al. | |
| 8,490,862 B1 | 7/2013 | Minvielle | |
| 8,550,365 B1 | 10/2013 | Minvielle | |
| 8,626,796 B2 | 1/2014 | McBride et al. | |
| 8,631,050 B1* | 1/2014 | Gayle | 707/803 |
| 8,668,140 B2 | 3/2014 | Minvielle | |
| D702,482 S | 4/2014 | Davis et al. | |
| 8,733,631 B2 | 5/2014 | Minvielle | |
| 8,783,556 B2 | 7/2014 | Minvielle | |
| 8,788,341 B1 | 7/2014 | Patel | |
| 8,796,510 B2 | 8/2014 | Heard et al. | |
| 8,825,516 B2 | 9/2014 | Grant et al. | |
| 8,851,365 B2 | 10/2014 | Minvielle | |
| 9,016,193 B2 | 4/2015 | Minvielle | |
| 9,084,566 B2 | 7/2015 | Zdeblick | |
| 9,165,320 B1 | 10/2015 | Belvin | |
| 9,241,909 B2 | 1/2016 | Selanikio | |
| 2002/0004749 A1 | 1/2002 | Froseth et al. | |
| 2002/0005412 A1 | 1/2002 | Laforcade | |
| 2002/0011567 A1 | 1/2002 | Ozanich | |
| 2002/0040564 A1 | 4/2002 | Killingbeck et al. | |
| 2002/0059175 A1 | 5/2002 | Nakano | |
| 2002/0085164 A1 | 7/2002 | Stanford-Clark | |
| 2002/0091593 A1 | 7/2002 | Fowler | |
| 2002/0106432 A1 | 8/2002 | Yamagata et al. | |
| 2002/0123070 A1 | 9/2002 | Hsieh | |
| 2002/0125313 A1 | 9/2002 | Broff | |
| 2002/0163436 A1 | 11/2002 | Singh et al. | |
| 2002/0168456 A1 | 11/2002 | Robbins | |
| 2003/0006281 A1 | 1/2003 | Thomas et al. | |
| 2003/0027161 A1 | 2/2003 | Bejanin et al. | |
| 2003/0050730 A1 | 3/2003 | Greeven et al. | |
| 2003/0099157 A1 | 5/2003 | Quine | |
| 2003/0136960 A1 | 7/2003 | Goodman et al. | |
| 2003/0163354 A1 | 8/2003 | Shamoun | |
| 2003/0165602 A1 | 9/2003 | Garwood | |
| 2003/0185937 A1 | 10/2003 | Garwood | |
| 2003/0185948 A1 | 10/2003 | Garwood | |
| 2003/0204359 A1 | 10/2003 | Blakley | |
| 2003/0227392 A1 | 12/2003 | Ebert et al. | |
| 2004/0045202 A1 | 3/2004 | Arrendale, III et al. | |
| 2004/0083201 A1 | 4/2004 | Sholl et al. | |
| 2004/0093274 A1 | 5/2004 | Vanska et al. | |
| 2004/0100380 A1 | 5/2004 | Lindsay et al. | |
| 2004/0130714 A1 | 7/2004 | Gellerman et al. | |
| 2004/0147038 A1 | 7/2004 | Lewis et al. | |
| 2004/0148117 A1 | 7/2004 | Kirshenbaum et al. | |
| 2004/0152131 A1 | 8/2004 | Hsieh | |
| 2004/0158447 A1 | 8/2004 | Leger et al. | |
| 2004/0167724 A1 | 8/2004 | Federer et al. | |
| 2004/0177011 A1 | 9/2004 | Ramsay et al. | |
| 2004/0191382 A1* | 9/2004 | Cooper et al. | 426/521 |
| 2004/0201454 A1 | 10/2004 | Waterhouse et al. | |
| 2004/0215402 A1 | 10/2004 | Hsiung et al. | |
| 2004/0261280 A1 | 12/2004 | Znaiden et al. | |
| 2004/0267098 A1 | 12/2004 | Moore | |
| 2005/0001728 A1 | 1/2005 | Appelt et al. | |
| 2005/0027726 A1 | 2/2005 | Guivarch et al. | |
| 2005/0049920 A1 | 3/2005 | Day et al. | |
| 2005/0075900 A1 | 4/2005 | Arguimbau, III | |
| 2005/0079491 A1 | 4/2005 | Donne-Gousse et al. | |
| 2005/0106103 A1 | 5/2005 | Dussaud et al. | |
| 2005/0168325 A1 | 8/2005 | Lievre et al. | |
| 2005/0171738 A1 | 8/2005 | Kadaba | |
| 2005/0184148 A1 | 8/2005 | Perlman | |
| 2005/0247213 A1 | 11/2005 | Slilaty | |
| 2005/0248455 A1 | 11/2005 | Pope et al. | |
| 2005/0251449 A1 | 11/2005 | Pape et al. | |
| 2006/0015371 A1 | 1/2006 | Knauf et al. | |
| 2006/0061454 A1 | 3/2006 | Debord et al. | |
| 2006/0062835 A1 | 3/2006 | Weil | |
| 2006/0073483 A1 | 4/2006 | White et al. | |
| 2006/0078658 A1 | 4/2006 | Owens et al. | |
| 2006/0099310 A1 | 5/2006 | Koekkoek | |
| 2006/0130498 A1 | 6/2006 | Joshi et al. | |
| 2006/0172048 A1 | 8/2006 | Etchells et al. | |
| 2006/0178841 A1 | 8/2006 | Fernandez | |
| 2006/0200480 A1 | 9/2006 | Harris et al. | |
| 2006/0201432 A1 | 9/2006 | Pratt | |
| 2006/0228428 A1 | 10/2006 | Kang et al. | |
| 2006/0240174 A1* | 10/2006 | Jung et al. | 426/658 |
| 2006/0256132 A1 | 11/2006 | Shin et al. | |
| 2006/0277064 A1 | 12/2006 | Cannata | |
| 2006/0286211 A1 | 12/2006 | Lang | |
| 2007/0016852 A1 | 1/2007 | Kim et al. | |
| 2007/0036840 A1 | 2/2007 | Tuduri et al. | |
| 2007/0049910 A1 | 3/2007 | Altshuler et al. | |
| 2007/0055551 A1 | 3/2007 | Szabo | |
| 2007/0055573 A1 | 3/2007 | Grell | |
| 2007/0059402 A1 | 3/2007 | Barmore | |
| 2007/0118394 A1 | 5/2007 | Cahoon | |
| 2007/0191689 A1 | 8/2007 | Elitok | |
| 2007/0204691 A1 | 9/2007 | Bogner et al. | |
| 2007/0207242 A1 | 9/2007 | Carlsen | |
| 2007/0209656 A1 | 9/2007 | Lee | |
| 2007/0254080 A1 | 11/2007 | Schackmuith et al. | |
| 2007/0258048 A1 | 11/2007 | Pitchers | |
| 2007/0269557 A1 | 11/2007 | Culver et al. | |
| 2007/0294129 A1 | 12/2007 | Froseth et al. | |
| 2007/0298147 A1 | 12/2007 | Haus | |
| 2008/0058783 A1 | 3/2008 | Altshuler et al. | |
| 2008/0059342 A1 | 3/2008 | Culver et al. | |
| 2008/0077455 A1 | 3/2008 | Gilboa | |
| 2008/0083825 A1 | 4/2008 | Yang et al. | |
| 2008/0091705 A1 | 4/2008 | McBride et al. | |
| 2008/0102175 A1* | 5/2008 | Jeon | F24C 15/14 426/233 |
| 2008/0158543 A1 | 7/2008 | Puskas et al. | |
| 2008/0162186 A1 | 7/2008 | Jones | |
| 2008/0171120 A1 | 7/2008 | Willett | |
| 2008/0183588 A1 | 7/2008 | Agrawal et al. | |
| 2008/0186175 A1 | 8/2008 | Stern | |
| 2008/0193614 A1 | 8/2008 | Greiner et al. | |
| 2008/0195456 A1 | 8/2008 | Fitzpatrick et al. | |
| 2008/0254449 A1 | 10/2008 | Plante | |
| 2008/0275309 A1 | 11/2008 | Stivoric et al. | |
| 2008/0280000 A1 | 11/2008 | Breunig et al. | |
| 2009/0029014 A1 | 1/2009 | Walter et al. | |
| 2009/0035392 A1 | 2/2009 | Wilkinson | |
| 2009/0065570 A1 | 3/2009 | Peters et al. | |
| 2009/0070040 A1 | 3/2009 | Rabinovitch et al. | |
| 2009/0099873 A1 | 4/2009 | Kurple | |
| 2009/0157460 A1 | 6/2009 | Narayanaswamy | |
| 2009/0177068 A1* | 7/2009 | Stivoric et al. | 600/365 |
| 2009/0202700 A1 | 8/2009 | Bunke et al. | |
| 2009/0208607 A1 | 8/2009 | Bunke et al. | |
| 2009/0232958 A1 | 9/2009 | Samoto et al. | |
| 2009/0275002 A1 | 11/2009 | Hoggle | |
| 2009/0276912 A1 | 11/2009 | Sherman et al. | |

(56) References Cited

U.S. PATENT DOCUMENTS

| | | |
|---|---|---|
| 2009/0278685 A1 | 11/2009 | Potyrailo et al. |
| 2009/0282004 A1 | 11/2009 | Williams |
| 2009/0283517 A1 | 11/2009 | Mackay et al. |
| 2009/0286212 A1 | 11/2009 | Gordon |
| 2009/0288606 A1 | 11/2009 | Zimmerman |
| 2010/0055259 A1 | 3/2010 | Bourg, Jr. |
| 2010/0055653 A1 | 3/2010 | Miller-Kovach et al. |
| 2010/0075436 A1 | 3/2010 | Urdea et al. |
| 2010/0076585 A1 | 3/2010 | Mayer et al. |
| 2010/0076942 A1 | 3/2010 | Lee |
| 2010/0086655 A1 | 4/2010 | Singer |
| 2010/0097193 A1 | 4/2010 | Tang |
| 2010/0102959 A1 | 4/2010 | Ashrafzadeh et al. |
| 2010/0106625 A1 | 4/2010 | McCoy |
| 2010/0106626 A1 | 4/2010 | Ashrafzadeh et al. |
| 2010/0117819 A1 | 5/2010 | Murray |
| 2010/0119659 A1 | 5/2010 | Ovadia et al. |
| 2010/0125419 A1 | 5/2010 | Hyde et al. |
| 2010/0135211 A1 | 6/2010 | Park et al. |
| 2010/0152687 A1 | 6/2010 | Carlozzi |
| 2010/0175886 A1 | 7/2010 | Bohacs et al. |
| 2010/0185064 A1 | 7/2010 | Bandic et al. |
| 2010/0198605 A1 | 8/2010 | Saulet |
| 2010/0213187 A1 | 8/2010 | Bandholz et al. |
| 2010/0216098 A1 | 8/2010 | Montgomery |
| 2010/0216136 A1 | 8/2010 | Man et al. |
| 2010/0218044 A1 | 8/2010 | Roblett et al. |
| 2010/0228160 A1 | 9/2010 | Schweizer |
| 2010/0250271 A1 | 9/2010 | Pearce et al. |
| 2010/0253519 A1 | 10/2010 | Brackmann et al. |
| 2010/0264205 A1 | 10/2010 | Iida |
| 2010/0268658 A1 | 10/2010 | Medo et al. |
| 2010/0280895 A1 | 11/2010 | Mottola |
| 2010/0281636 A1 | 11/2010 | Ortins et al. |
| 2010/0287057 A1 | 11/2010 | Aihara et al. |
| 2010/0287101 A1 | 11/2010 | Ishikawa et al. |
| 2011/0020785 A1 | 1/2011 | Lowery, Jr. et al. |
| 2011/0029364 A1 | 2/2011 | Roeding et al. |
| 2011/0082711 A1 | 4/2011 | Poeze et al. |
| 2011/0123689 A1 | 5/2011 | Luckhardt et al. |
| 2011/0124096 A1 | 5/2011 | Philipak et al. |
| 2011/0153364 A1 | 6/2011 | Kerr et al. |
| 2011/0197827 A1 | 8/2011 | Chang |
| 2011/0204137 A1 | 8/2011 | Scharfenort et al. |
| 2011/0217205 A1 | 9/2011 | Peeters |
| 2011/0236862 A1 | 9/2011 | Culver et al. |
| 2011/0240730 A1 | 10/2011 | Covely |
| 2011/0257496 A1 | 10/2011 | Terashima et al. |
| 2011/0258130 A1 | 10/2011 | Grabiner et al. |
| 2011/0259953 A1 | 10/2011 | Baarman et al. |
| 2011/0259960 A1 | 10/2011 | Baarman et al. |
| 2011/0276402 A1 | 11/2011 | Boone |
| 2011/0301441 A1 | 12/2011 | Bandic et al. |
| 2011/0302050 A1 | 12/2011 | Kildevaeld |
| 2011/0318717 A1 | 12/2011 | Adamowicz |
| 2012/0004935 A1 | 1/2012 | Winkler |
| 2012/0005105 A1 | 1/2012 | Beier et al. |
| 2012/0005222 A1 | 1/2012 | Bhagwan et al. |
| 2012/0009550 A1 * | 1/2012 | Gayle ............................ 434/127 |
| 2012/0016814 A1 | 1/2012 | Evans |
| 2012/0027897 A1 | 2/2012 | Innocenzi |
| 2012/0052162 A1 | 3/2012 | Goulart |
| 2012/0055718 A1 | 3/2012 | Chen |
| 2012/0083669 A1 | 4/2012 | Abujbara |
| 2012/0085828 A1 | 4/2012 | Ziegler |
| 2012/0085829 A1 | 4/2012 | Ziegler |
| 2012/0097050 A1 | 4/2012 | Schaefer et al. |
| 2012/0105424 A1 | 5/2012 | Lee et al. |
| 2012/0135455 A1 | 5/2012 | Nerin De La Puerta et al. |
| 2012/0152406 A1 | 6/2012 | Bartholomew et al. |
| 2012/0169469 A1 | 7/2012 | Butler et al. |
| 2012/0173269 A1 * | 7/2012 | Omidi ................................ 705/2 |
| 2012/0179665 A1 | 7/2012 | Baarman et al. |
| 2012/0199643 A1 | 8/2012 | Minnick et al. |
| 2012/0203572 A1 | 8/2012 | Christensen |
| 2012/0216911 A1 | 8/2012 | Bartholomew et al. |
| 2012/0251663 A1 | 10/2012 | Prins et al. |
| 2012/0274470 A1 | 11/2012 | Sandvick |
| 2012/0290051 A1 * | 11/2012 | Boyden et al. ................ 607/113 |
| 2012/0315609 A1 | 12/2012 | Miller-Kovach et al. |
| 2012/0321759 A1 | 12/2012 | Marinkovich et al. |
| 2013/0030944 A1 | 1/2013 | Nicod et al. |
| 2013/0033031 A1 | 2/2013 | Key |
| 2013/0035787 A1 | 2/2013 | Canter |
| 2013/0048736 A1 | 2/2013 | Wien |
| 2013/0048737 A1 | 2/2013 | Baym et al. |
| 2013/0052616 A1 | 2/2013 | Silverstein et al. |
| 2013/0080098 A1 | 3/2013 | Hadad et al. |
| 2013/0080784 A1 | 3/2013 | Oertli |
| 2013/0105470 A1 | 5/2013 | De Luca et al. |
| 2013/0105565 A1 | 5/2013 | Kamprath |
| 2013/0117310 A1 | 5/2013 | Chai et al. |
| 2013/0209615 A1 | 8/2013 | Lee et al. |
| 2013/0231711 A1 | 9/2013 | Kaib |
| 2013/0255507 A1 | 10/2013 | Meunier et al. |
| 2013/0269297 A1 | 10/2013 | Minvielle |
| 2013/0269454 A1 | 10/2013 | Minvielle |
| 2013/0269537 A1 | 10/2013 | Minvielle |
| 2013/0269538 A1 | 10/2013 | Minvielle |
| 2013/0269542 A1 | 10/2013 | Minvielle |
| 2013/0269543 A1 | 10/2013 | Minvielle |
| 2013/0269544 A1 | 10/2013 | Minvielle |
| 2013/0270337 A1 | 10/2013 | Minvielle |
| 2013/0273217 A1 | 10/2013 | Minvielle |
| 2013/0273222 A1 | 10/2013 | Minvielle |
| 2013/0273507 A1 | 10/2013 | Minvielle |
| 2013/0273509 A1 | 10/2013 | Mutti |
| 2013/0275037 A1 | 10/2013 | Minvielle |
| 2013/0275318 A1 | 10/2013 | Minvielle |
| 2013/0275342 A1 | 10/2013 | Minvielle |
| 2013/0275343 A1 | 10/2013 | Minvielle |
| 2013/0275370 A1 | 10/2013 | Minvielle |
| 2013/0275426 A1 | 10/2013 | Minvielle |
| 2013/0275439 A1 | 10/2013 | Minvielle |
| 2013/0275460 A1 | 10/2013 | Minvielle |
| 2013/0275477 A1 | 10/2013 | Minvielle |
| 2013/0276644 A1 | 10/2013 | Minvielle |
| 2013/0287060 A1 | 10/2013 | Langdoc et al. |
| 2013/0290364 A1 | 10/2013 | Minvielle |
| 2013/0295532 A1 | 11/2013 | Minvielle |
| 2013/0297642 A1 | 11/2013 | Minvielle |
| 2013/0302483 A1 | 11/2013 | Riefenstein |
| 2013/0309138 A1 | 11/2013 | Minvielle |
| 2013/0309636 A1 | 11/2013 | Minvielle |
| 2013/0309637 A1 | 11/2013 | Minvielle |
| 2013/0310955 A1 | 11/2013 | Minvielle |
| 2013/0327231 A1 | 12/2013 | Holman et al. |
| 2013/0337516 A1 | 12/2013 | Herrema |
| 2014/0018636 A1 * | 1/2014 | Contant et al. ................ 600/301 |
| 2014/0026762 A1 | 1/2014 | Riefenstein |
| 2014/0037805 A1 | 2/2014 | Minvielle |
| 2014/0038140 A1 | 2/2014 | Minvielle |
| 2014/0041532 A1 | 2/2014 | Minvielle |
| 2014/0041533 A1 | 2/2014 | Minvielle |
| 2014/0061296 A1 | 3/2014 | Minvielle |
| 2014/0069838 A1 | 3/2014 | Minvielle |
| 2014/0191025 A1 | 7/2014 | Minvielle |
| 2014/0214714 A1 | 7/2014 | Minvielle |
| 2014/0236359 A1 | 8/2014 | Minvielle |
| 2014/0263640 A1 | 9/2014 | Heit et al. |
| 2014/0279088 A1 | 9/2014 | Hurst et al. |
| 2014/0290395 A1 | 10/2014 | Minvielle |
| 2014/0290396 A1 | 10/2014 | Minvielle |
| 2014/0292520 A1 | 10/2014 | Carney et al. |
| 2014/0339296 A1 | 11/2014 | McAdams et al. |
| 2014/0364971 A1 | 12/2014 | Minvielle |
| 2015/0012122 A1 | 1/2015 | Minvielle |
| 2015/0017252 A1 * | 1/2015 | Garland et al. ................ 424/538 |
| 2015/0037764 A1 | 2/2015 | Minvielle |
| 2015/0051841 A1 | 2/2015 | Minvielle |
| 2015/0057773 A1 | 2/2015 | Minvielle |
| 2015/0100350 A1 | 4/2015 | Minvielle |
| 2015/0100462 A1 | 4/2015 | Minvielle |
| 2015/0118659 A1 | 4/2015 | Meyer |

(56) References Cited

U.S. PATENT DOCUMENTS

| | | |
|---|---|---|
| 2015/0149120 A1 | 5/2015 | Burkhardt et al. |
| 2015/0227887 A1 | 8/2015 | Minvielle |
| 2015/0235566 A1 | 8/2015 | Minvielle |
| 2015/0236913 A1 | 8/2015 | Nakano et al. |
| 2015/0320808 A1 | 11/2015 | Burcelin et al. |

FOREIGN PATENT DOCUMENTS

| | | |
|---|---|---|
| DE | 19843016 A1 | 3/2000 |
| DE | 10 2005 040206 A1 | 2/2007 |
| DE | 10 2007 032 303 A | 1/2008 |
| EP | 1 253 203 A1 | 10/2002 |
| EP | 1117055 A2 | 7/2007 |
| FR | 2813683 A1 | 3/2002 |
| GB | 2312054 A | 10/1997 |
| WO | WO 91/13304 A1 | 9/1991 |
| WO | WO 02/06984 | 1/2002 |
| WO | WO 02/37375 A1 | 5/2002 |
| WO | WO 2007/108906 A2 | 9/2007 |
| WO | WO 2008/054231 A1 | 5/2008 |
| WO | 2009/157750 | 12/2009 |
| WO | WO 2013/126579 A1 | 8/2013 |
| WO | 2013/134325 A1 | 9/2013 |
| WO | WO 2013/134544 A1 | 9/2013 |
| WO | WO 2013/142218 A1 | 9/2013 |
| WO | 2013/158571 A2 | 10/2013 |
| WO | 2013/158572 A2 | 10/2013 |
| WO | 2013/158576 A1 | 10/2013 |
| WO | 2013/176800 A1 | 11/2013 |
| WO | WO 2013/180925 A2 | 12/2013 |
| WO | 2014/168844 A2 | 10/2014 |
| WO | WO 2014/182566 A2 | 11/2014 |
| WO | WO 2014/210531 A2 | 12/2014 |
| WO | WO 2015/006351 A1 | 1/2015 |
| WO | WO 2015/013030 A1 | 1/2015 |
| WO | WO 2015/013031 A2 | 1/2015 |
| WO | 2015/054082 | 4/2015 |
| WO | WO 2015/069325 A1 | 5/2015 |
| WO | WO 2015/069950 A1 | 5/2015 |
| WO | WO 2015/073569 A1 | 5/2015 |

OTHER PUBLICATIONS

Advisory Action in U.S. Appl. No. 13/485,878, mailed Sep. 16, 2014.
Office Action in U.S. Appl. No. 13/888,353, mailed Oct. 1, 2014.
PCT International Search Report and Written Opinion in International Application No. PCT/US2014/044696, mailed Oct. 10, 2014.
PCT International Search Report and Written Opinion in International Application No. PCT/US2014/045796, mailed Oct. 15, 2014.
PCT International Search Report and Written Opinion in International Application No. PCT/US2014/045798, mailed Oct. 15, 2014.
Bell, S. et al., "Report on nutrient losses and gains factors used in European food composition databases", Technical Report, Apr. 2006, 66 pages (Retrieved from the Internet on Mar. 2, 2015 at: http://www.eurofir.net).
Hugh, J. "Recipe Calculations: Where Do We Stand?", Proceedings of the 12th National Nutrient Databank Conference, Houston, Texas, Apr. 12, 1987, pp. 135-139 (Retrieved from the Internet on Feb. 13, 2015 at http://www.nutrientdataconf.org/PastConf/NDBC12/5-2_Joseph.pdf).
Valero, C., et al., "Design Guidelines for a Quality Assessment System of Fresh Fruits in Fruit Centers and Hypermarkets", Abstract, Agriculture Engineering International: the CIGR Journal of Scientific Research and Development, vol. II, Aug. 2000, 20 pages. Available online at http://dspace.library.cornell.edu/retrieve/237/, accessed Feb. 19, 2015.
Office Action in U.S. Appl. No. 13/485,863, mailed Feb. 9, 2015.
Office Action in U.S. Appl. No. 13/485,883, mailed Feb. 3, 2015.
Office Action in U.S. Appl. No. 13/485,900, mailed Feb. 3, 2015.
Office Action in U.S. Appl. No. 13/684,113, mailed Dec. 15, 2014.
Office Action in U.S. Appl. No. 13/861,300 mailed Feb. 24, 2015.
Office Action in U.S. Appl. No. 14/044,851, mailed Jan. 5, 2015.
Notice of Allowance in U.S. Appl. No. 14/059,441, mailed Jan. 5, 2015.
Notice of Allowance in U.S. Appl. No. 14/137,963, mailed Jan. 28, 2015.
Office Action in U.S. Appl. No. 14/304,671, mailed Feb. 4, 2015.
PCT International Search Report and Written Opinion in International Application No. PCT/US2014/045807, mailed Jan. 22, 2015.
PCT International Search Report and Written Opinion in International Application No. PCT/US14/59186, mailed Dec. 22, 2014.
PCT International Search Report and Written Opinion in International Application No. PCT/US2014/064434, mailed Feb. 20, 2015.
Communication Pursuant to Article 94(3) in European Application No. 13731655.0, dated Jan. 22, 2015.
Extended European Search Report in European Application No. 13751912.0, dated Feb. 25, 2015.
Office Action in U.S. Appl. No. 13/729,548, mailed Dec. 2, 2014.
"Automated Fruit Recognition" Fraunhofer, accessed online Nov. 13, 2014 and, available at http://www.iosb.fraunhofer.de/servlet/is/33328/.
Chung, I-C. et al., "A Portable Electrochemical Sensor for Caffeine and (-)Epigallocatechin Gallate Based on Molecularly Imprinted Poly(ethylene-co-vinyl alcohol) Recognition Element", J Nanosci Nanotechnol., vol. 11, No. 12, Dec. 2011, pp. 10633-10638.
"Cool runnings needed for fine wines," AFP, Apr. 28, 2008, retrieved from internet URL http://www.google.com/hostednews/afp/article/ALeqM5hm5gRK3maWqEJppJOBObR71THV on Feb. 10, 2014.
Composition of Foods Raw, Processed, Prepared USDA National Nutrient Database for Standard Reference, Release 26 Documentation and User Guide, U.S. Department of Agriculture Agricultural Research Service, Aug. 2013 (revised Nov. 2013), 136 pages, accessed on its website, at http://www.ars.usda.gov/SP2UserFiles/Place/12354500/Data/SR26/sr26_doc.pdf.
De Vos, K. et al., "Multiplexed antibody detection with an array of silicon-on-insulator microring resonators", IEEE, Photonics Journal, vol. 1, Issue 4, Oct. 2009, pp. 225-235.
Dorokhin, D. et al., "Imaging surface plasmon resonance for multiplex microassay sensing of mycotoxins", Analytical and Bioanalytical Chemistry, vol. 400, Issue 9, published online Apr. 12, 2011, pp. 3005-3011.
Ebarvia, et al, "Biomimetic piezoelectric quartz sensor for caffeine based on a molecularly imprinted polymer", Analytical and Bioanalytical Chemistry, vol. 378, Issue 5, Mar. 2004, published online Jan. 27, 2004, pp. 1331-1337.
Focke, M. et al., "Lab-on-a-Foil: microfluidics on thin and flexible films", Lab on a Chip, vol. 10, Issue 11, published online Mar. 19, 2010, pp. 1365-1386.
Gartia, M. et al., "Colorimetric plasmon resonance imaging using nano lycurgus cup arrays", Advanced Optical Materials, vol. 1, Issue 1, Jan. 2013, pp. 68-76.
Huang, et al., "A passive radio•frequency pH sensing tag for wireless food quality monitoring", IEEE Sensors Journal, vol. 12, Issue 3, Mar. 2012, pp. 487-495.
Kumar, A. et al., "Study of fiber optic sugar sensor", Pramana, vol. 67, Issue 2, Aug. 2006, pp. 383-387.
Kwon, H. et al., "Fluorescent DNAs printed on paper: Sensing food spoilage and ripening in the vapor phase", Chemical Science, vol. 3, Issue 8, published online May 17, 2012, pp. 2542-2549.
Lin, et al., "Multiplex fiber-optic biosensor using multiple particle plasmon resonances", International Society for Optics and Photonics: Third Asia Pacific Optical Sensors Conference, vol. 8351, Sydney, Australia, Jan. 31, 2012, pp. 83512S1-83512S7.
Ricci, F. et al., "A review on novel developments and applications of immunosensors in food analysis", Analytica Chimica Acta, vol. 605, Issue 2, Dec. 19, 2007, pp. 111-129.
Roche, PJR, et al., "A Camera Phone Localised Surface Plasmon Biosensing Platform Towards Low-Cost Label-Free Diagnostic Testing", Journal of Sensors, vol. 2011, 2011, 7 pages.
Scampicchio, M. et al., "Optical nanoprobes based on gold nanoparticles for sugar sensing", Nanotechnology, vol. 20, Issue 13, Apr. 1, 2009, 5 pages.

(56) References Cited

OTHER PUBLICATIONS

Zhu, H. et al., "Quantum dot enabled detection of *Escherichia coli* using a cell-phone", Analyst, vol. 137, Issue 11, Jun. 7, 2012, pp. 2541-2544.
Office Action in U.S. Appl. No. 13/685,575, mailed Oct. 27, 2014.
Office Action in U.S. Appl. No. 13/921,078, mailed Nov. 4, 2014.
Office Action in U.S. Appl. No. 13/931,733, mailed Nov. 6, 2014.
Office Action in U.S. Appl. No. 14/306,111, mailed Nov. 13, 2014.
Office Action in U.S. Appl. No. 29/497,888, mailed Nov. 19, 2014.
European Examination Report in European Application No. 13757669.0, dated Oct. 13, 2014.
Arora, P. et al., "An overview of transducers as platform for the rapid detection of foodborne pathogens", Appl. Microbial. Biotechnol., vol. 97, Issue 5, pp. 1829-1840, Jan. 18, 2013 (Published online).
"SIRA Technologies Food Sentinal System Thermal Barcode for Packaging", Sustainable is Good: Lifestyle and Design Blog, Mar. 4, 2009, 2 pages.
Aernecke, M.J. et al., "Optical-fiber Arrays for Vapor Sensing", Sensors and Actuators B: Chemical, Nov. 2009, vol. 142, Issue 2, pp. 464-469.
Anslyn, E.V., "Supramolecular Analytical Chemistry", The Journal of Organic Chemistry, Feb. 2, 2007, vol. 72, No. 3, pp. 687-699.
Chaudhry, Q. et al., "Applications and Implications of Nanotechnologies for the Food Sector", Food Additives and Contaminants: Part A, Mar. 2008, vol. 25, Issue 3, pp. 241-258.
Cheftel, J. Claude, "Food and Nutrition Labelling in the European Union", Food Chemistry 93.3, Dec. 2005, pp. 531-550, retrieved on Mar. 10, 2013 from URL: <http://www.sciencedirect.com/science/article/pii/S0308814604008581>.
Diller, K.R., "Stress Protein Expression Kinetics", Annual Review of Biomedical Engineering, 2006, vol. 8, pp. 403-424.
Etherington, Darrell, "iCarte Turns the iPhone Into an RFID Reader," Gigaom, Nov. 18, 2009 (downloaded Oct. 3, 2013, from URL http://gigaom.com/2009/11/18/icarte-turns-the-iphone-into-an-rfid-reader/).
Frankel, E.N., "Chemistry of Extra Virgin Olive Oil: Adulteration, Oxidative Stability, and Antioxidants", Journal of Agricultural and Food Chemistry, 2010, vol. 58 (10), pp. 5991-6006.
Garcia-Gonzalez, D.L. et al., "Research in Olive Oil: Challenges for the Near Future", Journal of Agricultural and Food Chemistry, 2010, vol. 58 (24), pp. 12569-12577.
Ghasemi-Varnamkhasti, M. et al., "Biomimetic-based odor and taste sensing systems to food quality and safety characterization: An overview on basic principles and recent achievements", Journal of Food Engineering, vol. 100, pp. 377-387, May 2010.
Grate, J.W., "Acoustic Wave Microsensor Arrays for Vapor Sensing", Chemical Reviews, 2000, vol. 100, No. 7, pp. 2627-2647.
Greenfield, H. et al., "Food composition data," FAO, 2003 ("FAO").
Hayano-Kanashiro, C. et al., "Analysis of Gene Expression and Physiological Responses in Three Mexican Maize Landraces Under Drought Stress and Recovery Irrigation", PLoS One, Oct. 2009, vol. 4, Issue 10, e7531, pp. 1-19.
Hierlemann, A. et al., "Higher-Order Chemical Sensing", Chemical Reviews, 2008, vol. 108, No. 2, pp. 563-613.
Hoffman, B., "IBM Announces Food Traceability Technology", Food+Tech Connect, Oct. 19, 2011, 2 pages.
Hsieh, Meng-Da et al., "Limits of Recognition for Simple Vapor Mixtures Determined with a Microsensor Array", Analytical Chemistry, Apr. 1, 2004, vol. 76, No. 7, pp. 1885-1895.
James, D. et al., "Chemical Sensors for Electronic Nose Systems", Microchimica Acta, Feb. 2005, vol. 149, pp. 1-17.
Janata, J. et al., "Conducting Polymers in Electronic Chemical Sensors", Nature Materials, Jan. 2003, vol. 2, pp. 19-24.
Kaume, L. et al., "The Blackberry Fruit: A Review on Its Composition and Chemistry, Metabolism and Bioavailability, and Health Benefits", Journal of Agricultural and Food Chemistry, 2012, vol. 60 (23), pp. 5716-5727.
Kharif, Olga, "Janne Haverinen: Mapping the Great Indoors", Bloomberg BusinessWeek, May 9, 2012, retrieved from URL: <http://www.businessweek.com/articles/2012-08-09/janne-haverinen-mapping-the-great-indoors on Apr. 12, 2013>.
Kingsmore, S.F., "Multiplexed Protein Measurement: Technologies and Applications of Protein and Antibody Arrays", Nature Reviews Drug Discovery, Apr. 2006, vol. 5, pp. 310-321.
Lago, Fatima C. et al., "FINS Methodology to Identification of Sardines and Related Species in Canned Products and Detection of Mixture by Means of SNP Analysis Systems", European Food Research and Technology, Jun. 2011, vol. 232(6), pp. 1077-1086.
Lago, Fatima C. et al., "Genetic Identification of Horse Mackerel and Related Species in Seafood Products by Means of Forensically Informative Nucleotide Sequencing Methodology", Journal of Agricultural and Food Chemistry, 2011, vol. 59 (6), pp. 2223-2228.
Lewis, N.S., "Comparisons Between Mammalian and Artificial Olfaction Based on Arrays of Carbon Black-Polymer Composite Vapor Detectors", Accounts of Chemical Research, 2004, vol. 37, No. 9, pp. 663-672.
Martins-Lopes, P. et al., "DNA Markers for Portuguese Olive Oil Fingerprinting", Journal of Agricultural and Food Chemistry, 2008, vol. 56 (24), pp. 11786-11791.
Montealegre, C. et al., "Traceability Markers to the Botanical Origin in Olive Oils", Journal of Agricultural and Food Chemistry, 2010, vol. 58 (1), pp. 28-38.
Montesinos, E., "Plant-associated Microorganisms: a View from the Scope of Microbiology", International Microbiology, (2003), vol. 6, Issue 4, pp. 221-223.
Ni, Fu-Tai et al., "Gene Expression and Regulation of Higher Plants Under Soil Water Stress", Current Genomics, Jun. 2009, vol. 10, pp. 269-280.
Perks, B., "Fighting Food Fraud with Science", Text Reproduced from Chemistry World, 2007, vol. 4 (9), pp. 48-52.
Preechaburana, Pakorn et al., "Surface Plasmon Resonance Chemical Sensing on Cell Phones", Angewandte Chemie International Edition, vol. 51, Issue 46, pp. 11585-11588, first published online Oct. 16, 2012.
Primrose, S. et al., "Food Forensics: Methods for Determining the Authenticity of Foodstuffs", Trends in Food Science & Technology, Dec. 2010, vol. 21 (12), pp. 582-590.
Rashidi, L. et al., "The Applications of Nanotechnology in Food Industry", Critical Reviews in Food Science and Nutrition, 2011, vol. 51, Issue 8, pp. 723-730.
Röck, F. et al., "Electronic Nose: Current Status and Future Trends", Chemical Reviews, 2008, vol. 108, No. 2, pp. 705-725.
Sinclair, D.A. et al., "Unlocking the Secrets of Longevity Genes", Scientific American, Mar. 2006, vol. 294, Issue 3, pp. 48-57.
Srinivas, P.R. et al., "Nanotechnology Research: Applications in Nutritional Sciences", The Journal of Nutrition, Symposium-Nanotechnology Research: Applications in Nutritional Sciences, Jan. 2010, vol. 140, No. 1, pp. 119-124.
Staggers, N. et al., "Nanotechnology: The Coming Revolution and its Implications for Consumers, Clinicians, and Informatics", Nursing Outlook, Sep.-Oct. 2008, vol. 56, No. 5, pp. 268-274.
Suslick, B.A. et al., "Discrimination of Complex Mixtures by a Colorimetric Sensor Array: Coffee Aromas", Analytical Chemistry, Mar. 1, 2010, vol. 82, No. 5, pp. 2067-2073.
Thakur, M. et al., "Food Traceability, R&D in Norway", Food Technology, Apr. 2012, p. 42-46.
Walt, D.R., "Electronic Noses: Wake Up and Smell the Coffee", Analytical Chemistry, Feb. 1, 2005, vol. 77 (3), p. A-45.
Wolfbeis, O.S., "Materials for Fluorescence-based Optical Chemical Sensors", Journal of Materials Chemistry, 2005, vol. 15, pp. 2657-2669.
Zerebecki, R.A. et al., "Temperature Tolerance and Stress Proteins as Mechanisms of Invasive Species Success", PLoS One, Apr. 2011, vol. 6, Issue 4, e14806, pp. 1-7.
Zou, Ming-Qiang et al., "Rapid Authentication of Olive Oil Adulteration by Raman Spectrometry", Journal of Agricultural and Food Chemistry, 2009, vol. 57 (14), pp. 6001-6006.
PCT International Search Report and Written Opinion in International Application No. PCT/US2013/029686, mailed May 13, 2013.
PCT International Search Report and Written Opinion in International Application No. PCT/US2013/031106, mailed May 31, 2013.

(56) References Cited

OTHER PUBLICATIONS

PCT International Search Report and Written Opinion in International Application No. PCT/US2013/27148, mailed Jun. 18, 2013.
PCT International Search Report and Written Opinion in International Application No. PCT/US2013/29219, mailed Jun. 20, 2013.
PCT International Search Report and Written Opinion in International Application No. PCT/US2013/36666, mailed Oct. 4, 2013.
PCT International Search Report and Written Opinion in International Application No. PCT/US2013/036668, mailed Dec. 6, 2013.
PCT International Search Report and Written Opinion in International Application No. PCT/US2013/036670, mailed Aug. 19, 2013.
PCT International Search Report and Written Opinion in International Application No. PCT/US2013/036673, mailed Aug. 20, 2013.
PCT International Search Report and Written Opinion in International Application No. PCT/US2013/040445, mailed Oct. 25, 2013.
Extended European Search Report in European Application No. 13757669.0, dated Jan. 31, 2014.
Extended European Search Report in European Application No. 13731655.0, dated Feb. 24, 2014.
Statement in accordance with the Notice from the European Patent Office, dated Oct. 1, 2007, concerning business methods.
Notice from the European Patent Office, dated Oct. 1, 2007, concerning business methods, Official Journal EPO, pp. 592-593.
Office Action in U.S. Appl. No. 13/485,850, mailed May 9, 2013.
Office Action in U.S. Appl. No. 13/485,850, mailed Sep. 30, 2013.
Office Action in U.S. Appl. No. 13/485,850, mailed Mar. 20, 2014.
Office Action in U.S. Appl. No. 13/485,878, mailed Oct. 24, 2013.
Office Action in U.S. Appl. No. 13/485,878, mailed Jun. 5, 2014.
Office Action in U.S. Appl. No. 13/560,965, mailed Feb. 1, 2013.
Office Action in U.S. Appl. No. 13/602,040, mailed Oct. 23, 2013.
Office Action in U.S. Appl. No. 13/602,040, mailed Jul. 17, 2014.
Office Action in U.S. Appl. No. 13/685,575, mailed May 6, 2013.
Office Action in U.S. Appl. No. 13/685,575, mailed Oct. 24, 2013.
Office Action in U.S. Appl. No. 13/732,050, mailed Oct. 24, 2013.
Office Action in U.S. Appl. No. 13/732,050, mailed Apr. 10, 2014.
Office Action in U.S. Appl. No. 13/750,804, mailed Mar. 12, 2013.
Office Action in U.S. Appl. No. 13/771,004, mailed May 15, 2013.
Office Action in U.S. Appl. No. 13/771,004, mailed Jul. 8, 2013.
Office Action in U.S. Appl. No. 13/771,004, mailed Apr. 4, 2014.
Office Action in U.S. Appl. No. 13/900,426, mailed Aug. 8, 2013.
Office Action in U.S. Appl. No. 13/888,353, mailed May 1, 2014.
Office Action in U.S. Appl. No. 13/931,744, mailed Aug. 20, 2013.
Office Action in U.S. Appl. No. 13/937,167, mailed Oct. 28, 2013.
Office Action in U.S. Appl. No. 13/937,167, mailed Apr. 14, 2014.
Office Action in U.S. Appl. No. 13/948,004, mailed Oct. 24, 2013.
Office Action in U.S. Appl. No. 13/948,004, mailed Jun. 11, 2014.
Office Action in U.S. Appl. No. 14/047,817, mailed Nov. 29, 2013.
Office Action in U.S. Appl. No. 14/059,441, mailed Dec. 20, 2013.
Office Action in U.S. Appl. No. 14/059,441, mailed Feb. 11, 2014.
Office Action in U.S. Appl. No. 14/059,441 mailed Jul. 10, 2014.
Office Action in U.S. Appl. No. 14/074,664, mailed Jan. 8, 2014.
Notice of Allowance in U.S. Appl. No. 13/560,965, mailed Mar. 22, 2013.
Notice of Allowance in U.S. Appl. No. 13/750,804, mailed May 31, 2013.
Notice of Allowance in U.S. Appl. No. 13/900,426, mailed Dec. 16, 2013.
Notice of Allowance in U.S. Appl. No. 13/931,744, mailed Feb. 28, 2014.
Notice of Allowance in U.S. Appl. No. 14/047,817, mailed Apr. 14, 2014.
Office Action in U.S. Appl. No. 14/137,963, mailed Aug. 5, 2014.
Notice of Allowance in U.S. Appl. No. 14/074,664, mailed Jun. 2, 2014.
Office Action in U.S. Appl. No. 13/485,850, mailed Mar. 19, 2015.
Office Action in U.S. Appl. No. 13/485,866, mailed May 7, 2015.
Office Action in U.S. Appl. No. 13/485,883, mailed May 20, 2015.
Office Action in U.S. Appl. No. 13/485,916, mailed Mar. 27, 2015.
Office Action in U.S. Appl. No. 13/646,632, mailed Mar. 26, 2015.
Office Action in U.S. Appl. No. 13/685,575, mailed May 5, 2015.
Office Action in U.S. Appl. No. 13/771,004, mailed Mar. 10, 2015.
Office Action in U.S. Appl. No. 13/888,353, mailed Mar. 26, 2015.
Notice of Allowance in U.S. Appl. No. 13/921,078, mailed Apr. 1, 2015.
Office Action in U.S. Appl. No. 13/931,733, mailed Mar. 10, 2015.
Notice of Allowance in U.S. Appl. No. 14/044,851, mailed Mar. 31, 2015.
Office Action in U.S. Appl. No. 14/203,353, mailed Mar. 31, 2015.
Office Action in U.S. Appl. No. 14/260,115, mailed Apr. 16, 2015.
Office Action in U.S. Appl. No. 14/466,805, mailed Apr. 13, 2015.
Office Action in U.S. Appl. No. 14/286,627, mailed Apr. 24, 2015.
Office Action in U.S. Appl. No. 14/466,824, mailed May 7, 2015.
Notice of Allowance in U.S. Appl. No. 14/306,111, mailed Mar. 17, 2015.
PCT International Search Report and Written Opinion in International Application No. PCT/US2014/033084, mailed Mar. 6, 2015.
PCT International Search Report and Written Opinion in International Application No. PCT/US2014/036570, mailed Mar. 10, 2015.
PCT International Search Report and Written Opinion in International Application No. PCT/US2014/044700, mailed May 18, 2015.
PCT International Search Report and Written Opinion in International Application No. PCT/US2014/065281, mailed Mar. 13, 2015.
Office Action in U.S. Appl. No. 13/485,850 mailed Sep. 24, 2015.
Office Action in U.S. Appl. No. 13/485,854, mailed Aug. 21, 2015.
Office Action in U.S. Appl. No. 13/485,863, mailed Sep. 2, 2015.
Office Action in U.S. Appl. No. 13/485,878, mailed Jul. 8, 2015.
Office Action in U.S. Appl. No. 13/485,883, mailed Oct. 28, 2015.
Office Action in U.S. Appl. No. 13/485,916, mailed Sep. 18, 2015.
Office Action in U.S. Appl. No. 13/602,040, mailed Jul. 6, 2015.
Office Action in U.S. Appl. No. 13/646,632, mailed Oct. 20, 2015.
Office Action in U.S. Appl. No. 13/684,113, mailed Jul. 1, 2015.
Office Action in U.S. Appl. No. 13/729,548, mailed Jul. 14, 2015.
Office Action in U.S. Appl. No. 13/732,050, mailed Jun. 23, 2015.
Office Action in U.S. Appl. No. 13/771,004, mailed Oct. 22, 2015.
Office Action in U.S. Appl. No. 13/861,300 mailed Sep. 29, 2015.
Office Action in U.S. Appl. No. 13/888,353, mailed Sep. 9, 2015.
Notice of Allowance in U.S. Appl. No. 13/931,733, mailed Jun. 11, 2015.
Office Action in U.S. Appl. No. 13/937,167 mailed Aug. 17, 2015.
Office Action in U.S. Appl. No. 13/948,071, mailed Jul. 20, 2015.
Office Action in U.S. Appl. No. 13/948,078, mailed Aug. 5, 2015.
Office Action in U.S. Appl. No. 13/948,004, mailed Jul. 31, 2015.
Office Action in U.S. Appl. No. 14/080,768, mailed Jun. 17, 2015.
Office Action in U.S. Appl. No. 14/304,671, mailed Sep. 3, 2015.
Office Action in U.S. Appl. No. 14/203,353, mailed Aug. 20, 2015.
Office Action in U.S. Appl. No. 141/286,627, mailed Oct. 9, 2015.
Office Action in U.S. Appl. No. 14/667,608 mailed Nov. 2, 2015.
Office Action in U.S. Appl. No. 14/725,114 mailed Oct. 22, 2015.
Further Exam Report in European Application No. 13731655.0, dated Aug. 13, 2015.
Search Report and Written Opinion in Singapore application 2013045448 dated Jun. 24, 2015.
Extended European Search Report in European Application No. 13763782.3, dated Jun. 11, 2015.
PCT International Search Report and Written Opinion in International Application No. PCT/US2015/035872, mailed Sep. 3, 2015.
PCT International Search Report and Written Opinion in International Application No. PCT/US2015/035875, mailed Sep. 4, 2015.
alKanhal et al., "Changes in protein nutritional quality in fresh and recombined ultra high temperature treated milk during storage.", Int. J. Food Sci. Nutr., Nov. 2001; 52(6): 509-14, 2 pgs.
Qiao, Y, "Routine Techniques for Monitoring the Value of Animal Meals", Unknown, 2001, 224 pgs. https://books.google.com/books/about/Routine_Techniques_for_Monitoring_the_Nu.html?id=LhsktkRPZ7EC (No Copies Available Online Copyright Restricted).
Wijtzes, T., et al., "A decision support system for the prediction of microbial food safety and food quality", International Journal of Food Microbiology 42 (1997) 79-90.
Office Action in U.S. Appl. No. 13/485,854, mailed Mar. 17, 2016.
Office Action in U.S. Appl. No. 13/485,863, mailed Dec. 30, 2015.
Office Action in U.S. Appl. No. 13/485,866, mailed Dec. 24, 2015.
Office Action in U.S. Appl. No. 13/485,878, mailed Feb. 1, 2016.

(56) References Cited

OTHER PUBLICATIONS

Office Action in U.S. Appl. No. 13/485,883, mailed Apr. 19, 2016.
Office Action in U.S. Appl. No. 13/485,916, mailed Feb. 18, 2016.
Office Action in U.S. Appl. No. 13/602,040, mailed May 6, 2016.
Office Action in U.S. Appl. No. 13/646,632, mailed Dec. 31, 2015.
Office Action in U.S. Appl. No. 13/646,632, mailed Apr. 21, 2016.
Office Action in U.S. Appl. No. 13/685,575, mailed May 11, 2016.
Office Action in U.S. Appl. No. 13/684,113, mailed Jun. 8, 2016.
Office Action in U.S. Appl. No. 13/729,548, mailed Feb. 5, 2016.
Office Action in U.S. Appl. No. 13/732,050, mailed Jan. 15, 2016.
Office Action in U.S. Appl. No. 13/771,004, mailed May 31, 2016.
Notice of Allowance in U.S. Appl. No. 13/861,300, mailed Apr. 15, 2016.
Office Action in U.S. Appl. No. 13/887,150 mailed Nov. 20, 2015.
Office Action in U.S. Appl. No. 13/888,353, mailed Apr. 21, 2016.
Office Action in U.S. Appl. No. 13/937,167 mailed Mar. 2, 2016.
Office Action in U.S. Appl. No. 13/948,004, mailed Dec. 17, 2015.
Office Action in U.S. Appl. No. 14/080,768, mailed Jan. 25, 2016.
Office Action in U.S. Appl. No. 14/304,671, mailed Apr. 8, 2016.
Office Action in U.S. Appl. No. 14/203,353, mailed Mar. 7, 2016.
Office Action in U.S. Appl. No. 14/260,115, mailed Dec. 4, 2015.
Office Action in U.S. Appl. No. 14/466,805, mailed Nov. 20, 2015.
Office Action in U.S. Appl. No. 14/466,805, mailed Mar. 8, 2016.
Office Action in U.S. Appl. No. 14/286,627, mailed Mar. 3, 2016.
Office Action in U.S. Appl. No. 14/466,824, mailed Jan. 13, 2016.
Office Action in U.S. Appl. No. 14/307,365, mailed May 3, 2016.
Office Action in U.S. Appl. No. 14/667,608 mailed Mar. 16, 2016.
Office Action in U.S. Appl. No. 14/860,340 mailed Apr. 20, 2016.
Extended European Search Report in European Application No. 13778362.7, dated Nov. 27, 2015.
Search Report and Written Opinion in Singapore application 10201406107X dated Feb. 11, 2016.
Extended European Search Report in European Application No. 13757527.0, dated Mar. 24, 2016.
Extended European Search Report in European Application No. 13777608.4, dated Nov. 19, 2015.
Extended European Search Report in European Application No. 13793073.1 dated Jan. 14, 2016.
Extended European Search Report in European Application No. 13778042.5, dated Nov. 20, 2015.
PCT International Search Report and Written Opinion in International Application No. PCT/US2015/045562, mailed Nov. 23, 2015.
Office Action in U.S. Appl. No. 13/887,150 mailed Jun. 17, 2016.
Office Action in U.S. Appl. No. 13/948,083, mailed Jul. 14, 2016.
Notice of Allowance in U.S. Appl. No. 14/260,115, mailed Jun. 21, 2016.
Notice of Allowance in U.S. Appl. No. 14/286,627, mailed Jun. 22, 2016.
Office Action in U.S. Appl. No. 14/643,995 mailed Jun. 14, 2016.
Office Action in U.S. Appl. No. 14/725,114 mailed Jun. 27, 2016.

* cited by examiner

ΔN Meter (represented through color change)

ΔN Meter (represented through percentage change)

Sample Retention Nutrition Factors USD Data

Figure 15

Sample Data of Cooking Yields

| Food Group Code | NDB | Yield Description | Preparation Method | Cooking Yield % | n | SD | Yield Minimum % | Yield Maximum % | Moisture Gain/Loss % | Fat Gain/Loss % | Release Year |
|---|---|---|---|---|---|---|---|---|---|---|---|
| 13 | 13985 | Beef, bottom sirloin butt, tri-tip roast, separable lean only, trimmed to 0" fat, all grades | Baked or Roasted, unspecified | 84 | 20 | 3.1 | 77 | 89 | -25.3 | 0.4 | 2001 |
| 13 | 13953 | Beef, bottom sirloin, tri-tip roast, separable lean and fat, trimmed to 0" fat, all grades | Baked or Roasted, unspecified | 84 | 20 | 3.1 | 77 | 89 | -22.4 | -0.1 | 2003 |
| 13 | 13606 | Beef, brisket, flat half, separable lean and fat, trimmed to 1/8" fat, all grades | Braised | 69 | 20 | 3.0 | 65 | 76 | -25.0 | -10.2 | 2000 |
| 13 | 23595 | Beef, brisket, flat half, separable lean only, trimmed to 1/8" fat, all grades | Braised | 69 | 20 | 3.0 | 65 | 76 | -29.7 | 0.5 | 2003 |
| 13 | 23134 | Beef, chuck eye country-style ribs, boneless, separable lean and fat, trimmed to 0" fat, all grades | Braised | 68 | 70 | 5.3 | 61 | 80 | -35.4 | -2.1 | 2010 |

Figure 18

INSTRUCTIONS FOR CONDITIONING NUTRITIONAL SUBSTANCES

RELATED PATENT APPLICATIONS

This application is a continuation in part of U.S. patent application Ser. No. 14/074,664 titled ADAPTIVE STORAGE AND CONDITIONING SYSTEMS FOR NUTRITIONAL SUBSTANCES, filed Nov. 7, 2013, which is a continuation in part of U.S. patent application Ser. No. 14/044,851 titled LOCAL STORAGE AND CONDITIONING SYSTEM FOR NUTRITIONAL SUBSTANCES, filed Oct. 2, 2013; which is a continuation-in-part of U.S. patent application Ser. No. 13/931,733 titled LOCAL STORAGE AND CONDITIONING SYSTEM FOR NUTRITIONAL SUBSTANCES, filed Jun. 28, 2013, which is a continuation-in-part of U.S. patent application Ser. No. 13/560,965, filed Jul. 27, 2012 and issued as U.S. Pat. No. 8,490,862, issued on Jul. 23, 2013, titled TRANSFORMATION SYSTEM FOR NUTRITIONAL SUBSTANCES, which is a continuation of Utility application Ser. No. 13/485,863 filed May 31, 2012, which, in turn, claims the benefit of U.S. Provisional Patent Application Ser. No. 61/625,002, filed Apr. 16, 2012; and U.S. Provisional Patent Application 61/625,010, filed Apr. 16, 2012, the contents of which are incorporated herein by reference in their entirety.

U.S. patent application Ser. No. 13/931,733 is also a continuation-in-part of U.S. patent application Ser. No. 13/602,040, titled CONDITIONING SYSTEM FOR NUTRITIONAL SUBSTANCES, filed Aug. 31, 2012, which is a continuation of U.S. patent application Ser. No. 13/485,866, filed May 31, 2012, which claims priority to U.S. Provisional Application No. 61/624,745, filed Apr. 16, 2012, U.S. Provisional Application No. 61/624,765, filed Apr. 16, 2012, and U.S. Provisional Application No. 61/624,788, filed Apr. 16, 2012, the contents of which are incorporated herein by reference in their entirety.

U.S. patent application Ser. No. 13/931,733 is also a continuation-in-part of U.S. patent application Ser. No. 13/684,113, titled TRANSFORMATION SYSTEM FOR OPTIMIZATION OF NUTRITIONAL SUBSTANCES AT CONSUMPTION, filed Nov. 21, 2012, which is a continuation of Utility application Ser. No. 13/485,863 filed May 31, 2012, which claims priority to U.S. Provisional Patent Application Ser. No. 61/624,992 filed Apr. 16, 2012; U.S. Provisional Patent Application Ser. No. 61/625,002, filed Apr. 16, 2012; and U.S. Provisional Patent Application 61/625,010, filed Apr. 16, 2012, the contents of which are incorporated herein by reference in their entirety.

FIELD OF THE INVENTION

The present inventions relate to appliances for nutritional substances in conjunction with the collection, transmission, and use of information regarding a current nutritional, organoleptic, or aesthetic value of the nutritional substance.

BACKGROUND OF THE INVENTION

Nutritional substances are traditionally grown (plants), raised (animals) or synthesized (synthetic compounds). Additionally, nutritional substances can be found in a wild, non-cultivated form, which can be caught or collected. While the collectors and creators of nutritional substances generally obtain and/or generate information about the source, history, caloric content and/or nutritional content of their products, they generally do not pass such information along to the users of their products. It would be desirable for such information be available to the consumers of nutritional substances, as well as all participants in the food and beverage industry—the nutritional substance supply system.

Caloric content refers to the energy in nutritional substances, commonly measured in calories. The caloric content could be represented as sugars and/or carbohydrates in the nutritional substances. The nutritional content, also referred to herein as nutritional value, of foods and beverages, as used herein, refers to the non-caloric content of these nutritional substances which are beneficial to the organisms which consume these nutritional substances. For example, the nutritional content of a nutritional substance could include vitamins, minerals, proteins, and other non-caloric components which are necessary, or at least beneficial, to the organism consuming the nutritional substances.

Consumers are beginning to that the food and beverage industry offer products which include higher nutritional content, and/or at least information regarding nutritional content of such products, as well as information regarding the source, creation and other origin information for the nutritional substance. In fact, consumers are already willing to pay higher prices for higher nutritional content. This can be seen at high-end grocery stores which offer organic, minimally processed, fresh, non-adulterated nutritional substances. Further, as societies and governments seek to improve their constituents' health and lower healthcare costs, incentives and/or mandates will be given to the food and beverage industry to track, maintain, and/or increase the nutritional content of nutritional substances they handle. There will be a need for an industry-wide solution to allow the management of nutritional content across the entire cycle from creation to consumption. In order to manage the nutritional content of nutritional substances across the entire cycle from creation to consumption, the nutritional substance industry will need to identify, track, measure, estimate, preserve, transform, condition, and record nutritional content for nutritional substances. Of particular importance are the measurement, estimation, and tracking of changes to the nutritional content of a nutritional substance from creation to consumption. This information could be used, not only by the consumer in selecting particular nutritional substances to consume, but could be used by the other food and beverage industry participants, including creation, preservation, transformation, and conditioning, to make decisions on how to create, handle and process nutritional substances. Additionally, those who sell nutritional substances to consumers, such as restaurants and grocery stores, could communicate perceived qualitative values of the nutritional substance in their efforts to market and position their nutritional substance products. Further, a determinant of price of the nutritional substance could be particular nutritional, organoleptic, or aesthetic values, and if changes to those values are perceived as desirable. For example, if a desirable value has been maintained, improved, or minimally degraded, it could be marketed as a premium product. Still further, a system allowing creators, preservers, transformers, and conditioners of nutritional substances to update labeling content to reflect the most current information about the nutritional substance would provide consumers with the information they need to make informed decisions regarding the nutritional substances they purchase and consume. Such information updates could include nutritional, organoleptic, or aesthetic values of the nutritional substance, and may further include information regarding the source, creation and other origin information for the nutritional substance.

For example, the grower of sweet corn generally only provides basic information as the variety and grade of its corn to the packager, who preserves and ships the corn to a producer for use in a ready-to-eat dinner. The packager may only tell the producer that the corn has been frozen as loose kernels of sweet corn. The producer may only provide the consumer with rudimentary instructions how to cook or reheat the ready-to-eat dinner in a microwave oven, toaster oven or conventional oven, and only tell the consumer that the dinner contains whole kernel corn among the various items in the dinner. Finally, the consumer of the dinner will likely keep her opinions on the quality of the dinner to herself, unless it was an especially bad experience, where she might contact the producer's customer support program to complain. Very minimal, or no, information on the nutritional content of the ready-to-eat dinner is passed along to the consumer. The consumer knows essentially nothing about changes (generally a degradation, but could be a maintenance or even an improvement) to the nutritional content of the sweet corn from creation, processing, packaging, cooking, preservation, preparation by consumer, and finally consumption by the consumer. The consumer is even more unlikely to be aware of possible changes to labeling content that a creator, preserver, transformer, or conditioner may just have become aware of, such as changes in information about nutritional, organoleptic, or aesthetic values of the nutritional substance or changes in information regarding the source, creation and other origin information about the nutritional substance. If communicated, such changes to labeling content could affect a purchasing preference or consumption preference of a consumer. Further, if communicated, such changes to labeling content could affect the health, safety, and wellbeing of the consumer. It is also clear that such changes would best be communicated rapidly and by a means readily utilized by a consumer.

Consumers' needs are changing as consumers are demanding healthier foods, such as "organic foods." Consumers are also asking for more information about the nutritional substances they consume, such as specific characteristics' relating not only to nutritional content, but to allergens or digestive intolerances. For example, nutritional substances which contain lactose, gluten, nuts, dyes, etc. need to be avoided by certain consumers. However, the producer of the ready-to-eat dinner, in the prior example, has very little information to share other than possibly the source of the elements of the ready-to-eat dinner and its processing steps in preparing the dinner. Generally, the producer of the ready-to-eat dinner does not know the nutritional content and organoleptic state and aesthetic condition of the product after it has been reheated or cooked by the consumer, cannot predict changes to these properties, and cannot inform a consumer of this information to enable the consumer to better meet their needs. For example, the consumer may want to know what proportion of desired organoleptic properties or values, desired nutritional content or values, or desired aesthetic properties or values of the corn in the ready-to-eat dinner remain after cooking or reheating, and the change in the desired nutritional content or values, the desired organoleptic properties or values, or the desired aesthetic properties or values (usually a degradation, but could be a maintenance or even improvement). There is a need to preserve, measure, estimate, store and/or transmit information regarding such nutritional, organoleptic, and aesthetic values, including changes to these values, throughout the nutritional substance supply system. Given the opportunity and a system capable of receiving and processing real time consumer feedback and updates regarding changes in the nutritional, organoleptic, and/or aesthetic value of nutritional substances, consumers can even play a role in updating dynamic information about the nutritional substances they have purchased and/or prepared for consumption, such that the information is available and useful to others in the nutritional substance supply system. Ideally, equipment for local storage of nutritional substances by consumers, such as any food preparation appliance, storage location, portable container, tray, bag, and so forth, could interact with nutritional substance products to provide such consumer feedback and updates. Ideally, equipment for conditioning of nutritional substances by consumers, such as any food preparation appliance, oven, toaster oven, toaster, blender, stove top, grill, microwave, and so forth, could interact with nutritional substance products to provide such consumer feedback and updates. Further, equipment for local storage of medicament products by consumers, such as any medicine cabinet, storage location, portable container, tray, bag, and so forth, could interact with the medicament product to provide such consumer feedback and updates.

The caloric and nutritional content information for a prepared food that is provided to the consumer is often minimal. For example, when sugar is listed in the ingredient list, the consumer generally does receive any information about the source of the sugar, which can come from a variety of plants, such as sugarcane, beets, or corn, which will affect its nutritional content. Conversely, some nutritional information that is provided to consumers is so detailed, the consumer can do little with it. For example, this of ingredients is from a nutritional label on a consumer product: Vitamins—A 355 IU 7%, E 0.8 mg 4%, K 0.5 mcg, 1%, Thiamin 0.6 mg 43%, Riboflavin 0.3 mg 20%, Niacin 6.0 mg 30%, B6 1.0 mg 52%, Foliate 31.5 mcg 8%, Pantothenic 7%; Minerals Calcium 11.6 1%, Iron 4.5 mg 25%, Phosphorus 349 mg 35%, Potassium 476 mg 14%, Sodium 58.1 mg 2%, Zinc 3.7 mg 24%, Copper 0.5 mg 26%, Manganese 0.8 mg 40%, Selenium 25.7 mcg 37%; Carbohydrate 123 g, Dietary fiber 12.1 g, Saturated fat 7.9 g, Monosaturated Fat 2.1 g, Polysaturated Fat 3.6 g, Omega 3 fatty acids 108 g, Omega 6 fatty acids 3481, Ash 2.0 g and Water 17.2 g. (%=Daily Value). There is a need to provide information about nutritional substances in a meaningful manner. Such information needs to be presented in a manner that meets the specific needs of a particular consumer. For example, consumers with a medical condition, such as diabetes, would want to track specific information regarding nutritional values associated with sugar and other nutrients in the foods and beverages they consume, and would benefit further from knowing changes in these values or having tools to quickly indicate or estimate these changes in a retrospective, current, or prospective fashion, and even tools to report these changes, or impressions of these changes, in a real-time fashion. Consumers would want to track medicaments for specific requirements, changes in their medicinal values, degradation, and for potential interactions with other medicaments and nutritional substances they are consuming or planning to consume.

In fact, each industry participant in the food and beverage industry already creates and tracks some information, including caloric and nutritional information, about their product internally. For example, the farmer who grew the corn knows the variety of the seed, condition of the soil, the source of the water, the fertilizers and pesticides used, and can measure the caloric and nutritional content at creation. The packager of the corn knows when it was picked, how it was transported to the packaging plant, how the corn was preserved and packaged before being sent to the ready-to-eat dinner producer, when it was delivered to the producer, and what degradation to caloric and nutritional content has occurred. The producer knows the source of each element of the ready-to-eat dinner, how it was processed, including the recipe followed, and how it was preserved and packaged for the consumer. Not only does such a producer know what degradation to caloric and nutritional content occurred, the producer can modify its processing and post-processing preservation to minimally affect nutritional content. The preparation of the nutritional substance for consumption can also degrade the nutritional content of nutritional substances. Finally, the consumer knows how she prepared the dinner, what condiments were added, and whether she did or did not enjoy it.

If there was a mechanism to share this information, the quality of the nutritional substances, including caloric and nutritional, organoleptic, and aesthetic value, could be preserved and improved. Consumers could be better informed about nutritional substances they select and consume, including the state, and changes in the state, of the nutritional substance throughout its lifecycle from creation to consumption. The efficiency and cost effectiveness of nutritional substances could also be improved. Feedback within the entire chain from creator to consumer could provide a closed-loop system that could improve quality (taste, appearance, and caloric and nutritional content), efficiency, value and profit. For example, in the milk supply chain, at least 10% of the milk produced is wasted due to safety margins included in product expiration dates. The use of more accurate tracking information, measured quality (including nutritional content) information, and historical environmental information could substantially reduce such waste. Collecting, preserving, measuring and/or tracking information about a nutritional substance in the nutritional substance supply system, would allow needed accountability. There would be nothing to hide.

As consumers are demanding more information about what they consume, they are asking for products that have higher nutritional content and more closely match good nutritional requirements, and would like nutritional products to actually meet their specific nutritional requirements. While grocery stores, restaurants, and all those who process and sell food and beverages may obtain some information from current nutritional substance tracking systems, such as labels, these current systems can provide only limited information.

Current packaging materials for nutritional substances include plastics, paper, cardboard, glass, and synthetic materials. Generally, the packaging material is chosen by the producer to best preserve the quality of the nutritional substance until used by the customer. In some cases, the packaging may include some information regarding type of nutritional substance, identity of the producer, and the country of origin. Such packaging generally does not transmit source information of the nutritional substance, such as creation information, current or historic information as to the external conditions of the packaged nutritional substance, or current or historic information as to the internal conditions of the packaged nutritional substance.

Traditional food processors take nutritional substances from producers and transform them into nutritional substances for consumption by consumers. While they have some knowledge of the nutritional substances they purchase, and make such selections to meet the needs of the consumers, they generally do not transmit that information along to consumers, nor change the way they transform the nutritional substances based on the history or current condition of the nutritional substances they receive for transformation.

Consumers of nutritional substances are sometimes given options on how to prepare nutritional substances they have obtained from the store, such as different cooking devices: microwave ovens, toaster ovens, conventional ovens, etc., and/or limited taste preferences such as crunchy or soft. However, if the consumer desires to prepare a specific recipe, they must obtain all the proper ingredients themselves, as well as prepare the recipe themselves including which cooking appliances need to be used. Further, the consumer has no way of knowing the history or current condition of the nutritional substances they obtain for preparing a desired recipe. Still further, the consumer has no way of knowing how to change or modify the conditioning process to achieve desired nutritional, organoleptic, and aesthetic properties after preparation. Consumers locally store, condition, and consume nutritional substances they acquire, but have no way to change the way they locally store, condition, and consume the nutritional substances based on the history or current condition of the nutritional substances.

An important issue in the creation, preservation, transformation, conditioning, and consumption of nutritional substances are the changes that occur in nutritional substances due to a variety of internal and external factors. Because nutritional substances are composed of biological, organic, and/or chemical compounds, they are generally subject to degradation. This degradation generally reduces the nutritional, organoleptic, and/or aesthetic values of nutritional substances. While not always true, nutritional substances are best consumed at their point of creation. However, being able to consume nutritional substances at the farm, at the slaughterhouse, at the fishery, or at the food processing plant is at least inconvenient, if not impossible. Currently, the food and beverage industry attempts to minimize the loss of nutritional, organoleptic, and/or aesthetic value, often through the use of additives or preservatives and often through freezing the nutritional substance, and/or attempts to hide this loss of nutritional, organoleptic, and/or aesthetic value from consumers. Consumers are left are provided with virtually no tools to help them in their attempts to determine and minimize the loss of nutritional, organoleptic, and/or aesthetic value of the nutritional substances they acquire, locally store, condition, and consume.

Overall, the examples herein of some prior or related systems and their associated limitations are intended to be illustrative and not exclusive. Other limitations of existing or prior systems will become apparent to those of skill in the art upon reading the following Detailed Description.

Objects of the Invention

In an object of the present invention is to allow for changes of nutritional, organoleptic, and/or aesthetic values of a nutritional substance to be tracked and degradation of said value to be tracked and minimized. In a further object, information regarding said changes or degradation, and information related to origin and creation of the nutritional substance, is collected, stored, and transmitted, from creation through consumption, including all phases of preservation, transformation, local storage and conditioning.

In an object of the present invention, appliances and equipment are provided to track changes of nutritional, organoleptic, and/or aesthetic values of a nutritional substance, and to minimize and/or track degradation of said values, and/or collect, store, and/or transmit information regarding these changes or degradation, and information related to origin and creation of the nutritional substance, during local storage and conditioning of the nutritional substance.

In an object of the present invention, local storage of a nutritional substance is modified or adapted to maintain and/or minimize degradation of and/or improve nutritional, organoleptic, and/or aesthetic values of the nutritional substance, responsive to information related to changes or degradation of nutritional, organoleptic, and/or aesthetic values of the nutritional substance.

In a further object of the present invention, local storage of a nutritional substance is modified or adapted to maintain and/or minimize degradation of and/or improve nutritional, organoleptic, and/or aesthetic values of the nutritional substance responsive to information regarding a residual nutritional, organoleptic, or aesthetic value of the nutritional substance at the initiation of said local storage.

In a further object of the present invention, local storage of a nutritional substance is modified or adapted to maintain and/or minimize degradation of and/or improve nutritional, organoleptic, and/or aesthetic values of the nutritional substance, responsive to information sensed during said local storage regarding a nutritional, organoleptic, or aesthetic value of the nutritional substance, including information relating to the weight of the substance.

In a further object of the present invention, an appliance for a nutritional substance is modified or adapted to display or output organoleptic, and/or aesthetic values of the nutritional substance, responsive to information sensed during said local storage regarding a nutritional, organoleptic, or aesthetic value of the nutritional substance, including information relating to the weight of the substance.

In a further object of the present invention, a nutritional substance database is provided that contains dynamic conditioning protocols that are modifiable or updatable, to improve the protocols impact on nutritional, organoleptic, and/or aesthetic values of the nutritional substance during conditioning.

In an object of the present invention, conditioning of a nutritional substance is modified or adapted to maintain and/or minimize degradation of and/or improve nutritional, organoleptic, and/or aesthetic values of the nutritional substance, responsive to information related to changes or degradation of nutritional, organoleptic, and/or aesthetic values of the nutritional substance.

In a further object of the present invention, conditioning of a nutritional substance is modified or adapted to maintain and/or minimize degradation of and/or improve nutritional, organoleptic, and/or aesthetic values of the nutritional substance responsive to information regarding a residual nutritional, organoleptic, or aesthetic value of the nutritional substance at the initiation of said conditioning.

In a further object of the present invention, conditioning of a nutritional substance is modified or adapted to maintain and/or minimize degradation of and/or improve nutritional, organoleptic, and/or aesthetic values of the nutritional substance, responsive to information sensed during said conditioning regarding a nutritional, organoleptic, or aesthetic value of the nutritional substance.

In a further object of the present invention, conditioning of a nutritional substance is modified or adapted to maintain and/or minimize degradation of and/or improve nutritional, organoleptic, and/or aesthetic values of the nutritional substance, responsive to at least one of current consumer information, current consumer input, or consumer input regarding prior experience.

In an object of the present invention, information related to changes or degradation of nutritional, organoleptic, and/or aesthetic values of a nutritional substance, including initial nutritional, organoleptic, and/or aesthetic values or other information related to the origin and creation of a nutritional substance, and information related to nutritional, organoleptic, and/or aesthetic values sensed during local storage and conditioning, can be utilized during local storage and conditioning of the nutritional substance to confirm compliance, or non-compliance, with general consumer requirements, or with a specific consumer's requirements, regarding nutritional, organoleptic, and/or aesthetic values, or regarding origin and creation of the nutritional substance.

In an object of the present invention, information collected by sensors of, or sensors communicating with, a local storage appliance, can collect all types of physical attribute data by sensing a nutritional substance, including weight data, and that the nutritional substance can be identified and its current nutritional, organoleptic, and aesthetic state determined, by comparing the sensed data to a library of data for known nutritional substances at known nutritional, organoleptic, and aesthetic states, and further that the nutritional substance can be adaptively stored responsive to: its initial nutritional, organoleptic, or aesthetic state; consumer input received through a consumer interface of the local storage appliance related to a desired nutritional, organoleptic, or aesthetic state after local storage; and information sensed during local storage related to changes in the nutritional substance's nutritional, organoleptic, or aesthetic state In an object of the present invention, information collected by sensors of, or sensors communicating with, a conditioning appliance, can collect all types of physical attribute data, including weight data, by sensing a nutritional substance, and that the nutritional substance can be identified and its current nutritional, organoleptic, and aesthetic state determined, by comparing the sensed data to a library of data for known nutritional substances at known nutritional, organoleptic, and aesthetic states, and further that the nutritional substance can be adaptively conditioned responsive to: its initial nutritional, organoleptic, or aesthetic state; consumer input received through a consumer interface of the conditioning appliance related to a desired nutritional, organoleptic, or aesthetic state after conditioning; and information sensed during conditioning related to changes in the nutritional substance's nutritional, organoleptic, or aesthetic state.

SUMMARY OF THE INVENTION

In an embodiment of the present invention, a system is provided for the tracking of changes of nutritional, organoleptic, and/or aesthetic values of a nutritional substance, wherein the system may collect, store, and transmit information regarding the changes of nutritional, organoleptic, and/or aesthetic values of the nutritional substance, and information related to origin and creation of the nutritional substance, from creation through consumption, including all phases of preservation, transformation, local storage and conditioning.

In embodiments of the present invention, appliances and equipment track changes of nutritional, organoleptic, and/or aesthetic values of a nutritional substance, and minimize and/or track degradation of said values, wherein the appliances and equipment may collect, store, and transmit information regarding the changes of nutritional, organoleptic, and/or aesthetic values of the nutritional substance, and information related to origin and creation of the nutritional substance, during local storage and conditioning of the nutritional substance.

In an embodiment of the present invention, local storage appliances and equipment modify or adapt local storage of a nutritional substance to maintain and/or minimize degradation of and/or improve, and/or display nutritional, organoleptic, and/or aesthetic values of the nutritional substance, responsive to information related to changes or degradation of nutritional, organoleptic, and/or aesthetic values of the nutritional substance.

In a further embodiment of the present invention, local storage appliances and equipment modify or adapt local storage of a nutritional substance to maintain and/or minimize degradation of and/or improve, and/or display nutritional, organoleptic, and/or aesthetic values of the nutritional substance responsive to information regarding a residual nutritional, organoleptic, or aesthetic value of the nutritional substance at the initiation of said local storage.

In a further embodiment of the present invention, local storage appliances and equipment modify or adapt local storage of a nutritional substance to maintain and/or minimize degradation of and/or improve, and/or display nutritional, organoleptic, and/or aesthetic values of the nutritional substance, responsive to information sensed during said local storage regarding a nutritional, organoleptic, or aesthetic value of the nutritional substance.

In an embodiment of the present invention, conditioning appliances and equipment modify or adapt conditioning of a nutritional substance to maintain and/or minimize degradation of and/or improve, and/or display nutritional, organoleptic, and/or aesthetic values of the nutritional substance, responsive to information related to changes or degradation of nutritional, organoleptic, and/or aesthetic values of the nutritional substance and responsive to information sensed within the conditioner and/or the of the nutritional substance.

In a further embodiment of the present invention, conditioning appliances and equipment modify or adapt local storage of a nutritional substance to maintain and/or minimize degradation of and/or improve, and/or display nutritional, organoleptic, and/or aesthetic values of the nutritional substance responsive to information regarding a residual nutritional, organoleptic, or aesthetic value of the nutritional substance at the initiation of said conditioning.

In a further embodiment of the present invention, conditioning appliances and equipment modify or adapt local storage of a nutritional substance to maintain and/or minimize degradation of and/or improve, and/or display nutritional, organoleptic, and/or aesthetic values of the nutritional substance, responsive to information sensed during said conditioning regarding a nutritional, organoleptic, or aesthetic value of the nutritional substance In an embodiment of the present invention, during local storage or conditioning of a nutritional substance, information related to changes or degradation of nutritional, organoleptic, and/or aesthetic values of the nutritional substance, including initial nutritional, organoleptic, and/or aesthetic values or other information related to the origin and creation of the nutritional substance, and information related to nutritional, organoleptic, and/or aesthetic values sensed during local storage and conditioning, is compared with general consumer requirements, or with a specific consumer's requirements, to confirm compliance, or non-compliance, regarding nutritional, organoleptic, and/or aesthetic values, or regarding origin and creation of the nutritional substance, or to display the nutritional, organoleptic, and/or aesthetic values to the consumer.

In an embodiment of the present invention, conditioning of a nutritional substance is modified or adapted to maintain and/or minimize degradation of and/or improve nutritional, organoleptic, and/or aesthetic values of the nutritional substance, responsive to at least one of current consumer information, current consumer input, or consumer input regarding prior experience.

In an embodiment of the present invention, information collected by sensors of, or sensors communicating with, a local storage appliance, for example weight measurement sensors, can collect all types of physical attribute data by sensing a nutritional substance, and can be identify the nutritional substance and its current nutritional, organoleptic, and aesthetic state by comparing the sensed data to a library of data for known nutritional substances at known nutritional, organoleptic, and aesthetic states, and further can be adaptively store the nutritional substance responsive to: its initial nutritional, organoleptic, or aesthetic state; consumer input received through a consumer interface of the local storage appliance related to a desired nutritional, organoleptic, or aesthetic state after local storage; and information sensed during local storage related to changes in the nutritional substance's nutritional, organoleptic, or aesthetic state.

In an embodiment of the present invention, information collected by sensors of, or sensors communicating with, a conditioning appliance, can collect all types of physical attribute data by sensing a nutritional substance including weight data, and can be identify the nutritional substance and its current nutritional, organoleptic, and aesthetic state by comparing the sensed data to a library of data for known nutritional substances at known nutritional, organoleptic, and aesthetic states, and further can be adaptively condition the nutritional substance responsive to: its initial nutritional, organoleptic, or aesthetic state; consumer input received through a consumer interface of the conditioning appliance related to a desired nutritional, organoleptic, or aesthetic state after conditioning; and information sensed during conditioning related to changes in the nutritional substance's nutritional, organoleptic, or aesthetic state.

Other advantages and features will become apparent from the following description and claims. It should be understood that the description and specific examples are intended for purposes of illustration only and not intended to limit the scope of the present disclosure.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 15 shows a table including values of the amount of nutritional content retained after cooking various nutritional substances based on data from the USDA.

FIG. 18 shows a table including values of various cooking yields for various nutritional substances based on data from the USDA.

Figure 1:
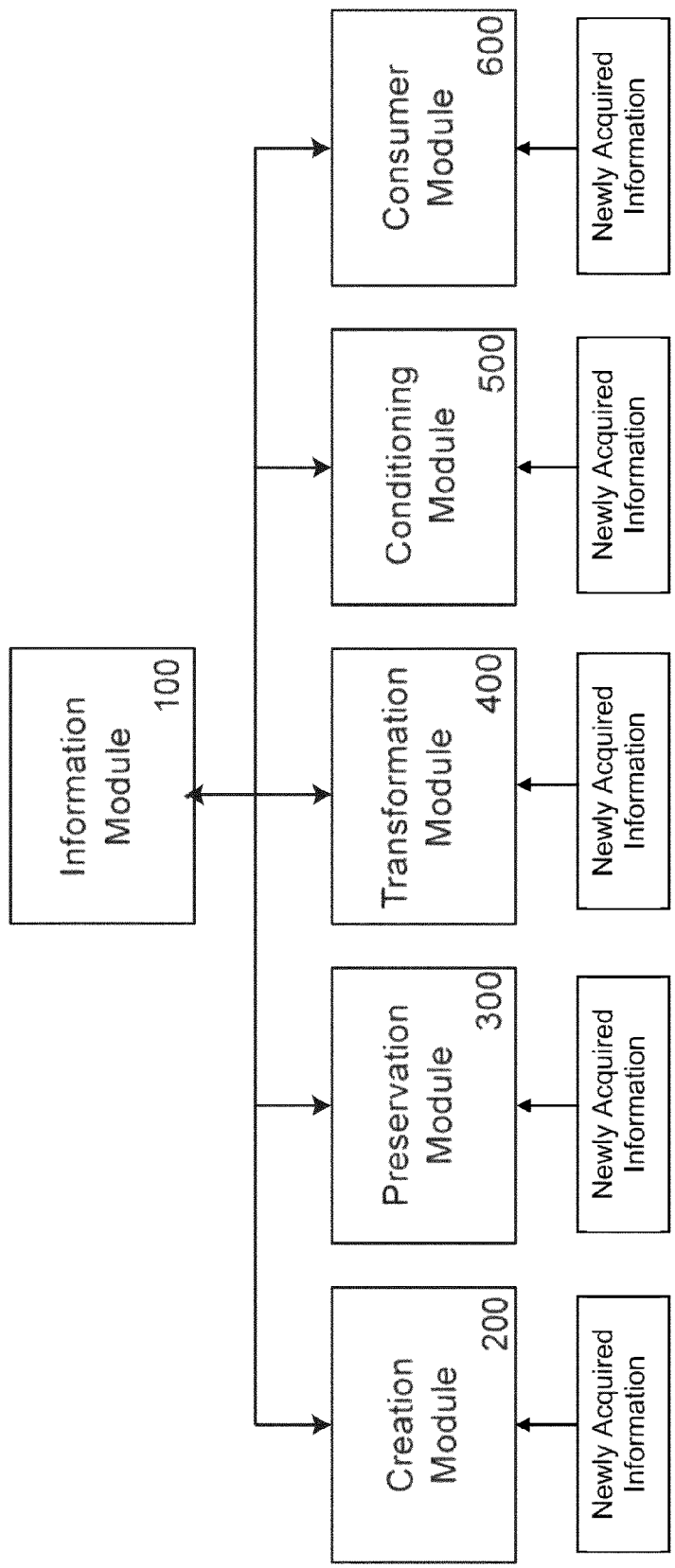
FIG. 1 shows a schematic functional block diagram of a nutritional substance supply system relating to the present invention.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION OF THE INVENTION

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

The following discussion provides a brief, general description of a representative environment in which the invention can be implemented. Although not required, aspects of the invention may be described below in the general context of computer-executable instructions, such as routines executed by a general-purpose data processing device (e.g., a server computer or a personal computer). Those skilled in the relevant art will appreciate that the invention can be practiced with other communications, data processing, or computer system configurations, including: wireless devices, Internet appliances, hand-held devices (including personal digital assistants (PDAs)), wearable computers, all manner of cellular or mobile phones, multi-processor systems, microprocessor-based or programmable consumer electronics, set-top boxes, network PCs, mini-computers, mainframe computers, and the like. Indeed, the terms "controller," "computer," "server," and the like are used interchangeably herein, and may refer to any of the above devices and systems.

While aspects of the invention, such as certain functions, are described as being performed exclusively on a single device, the invention can also be practiced in distributed environments where functions or modules are shared among disparate processing devices. The disparate processing devices are linked through a communications network, such as a Local Area Network (LAN), Wide Area Network (WAN), or the Internet. In a distributed computing environment, program modules may be located in both local and remote memory storage devices.

Aspects of the invention may be stored or distributed on tangible computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data related to the invention may be distributed over the Internet or over other networks (including wireless networks), on a propagated signal on a propagation medium (e.g., an electromagnetic wave(s), a sound wave, etc.) over a period of time. In some implementations, the data may be provided on any analog or digital network (packet switched, circuit switched, or other scheme).

In some instances, the interconnection between modules is the internet, allowing the modules (with, for example, WiFi capability) to access web content offered through various web servers. The network may be any type of cellular, IP-based or converged telecommunications network, including but not limited to Global System for Mobile Communications (GSM), Time Division Multiple Access (TDMA), Code Division Multiple Access (CDMA), Orthogonal Frequency Division Multiple Access (OFDM), General Packet Radio Service (GPRS), Enhanced Data GSM Environment (EDGE), Advanced Mobile Phone System (AMPS), Worldwide Interoperability for Microwave Access (WiMAX), Universal Mobile Telecommunications System (UMTS), Evolution-Data Optimized (EVDO), Long Term Evolution (LTE), Ultra Mobile Broadband (UMB), Voice over Internet Protocol (VoIP), Unlicensed Mobile Access (UMA), etc.

The modules in the systems can be understood to be integrated in some instances and in particular embodiments, only particular modules may be interconnected.

FIG. 1 shows the components of a nutritional substance industry 10. It should be understood that this could be the food and beverage ecosystem for human consumption, but could also be the feed industry for animal consumption, such as the pet food industry. A goal of the present invention for nutritional substance industry 10 is to create, preserve, transform and trace the change in nutritional, organoleptic and/or aesthetic values of nutritional substances, collectively and individually also referred to herein as ΔN, through their creation, preservation, transformation, conditioning and consumption. While the nutritional substance industry 10 can be composed of many companies or businesses, it can also be integrated into combinations of business serving many roles, or can be one business or even individual. Since ΔN is a measure of the change in a value of a nutritional substance, knowledge of a prior value (or state) of a nutritional substance and the ΔN value will provide knowledge of the changed value (or state) of a nutritional substance, and can further provide the ability to estimate a change in value (or state). The ΔN value may be represented or displayed to a consumer as a per unit weight (e.g., ΔN per ounce, or ΔN per grain) format or value, may be displayed as a graph showing the change of the in the nutritional substance over time or in various other formats that would demonstrate a change in a ΔN. For example, a consumer may be presented with a graph showing the historical or prospective change in the nutritional, organoleptic and/or aesthetic values of the nutritional substance, over time, cooking temperatures, or other choices or attributes. This presents a continuum to the consumer of how ΔN may change with the change in various factors including time and cooking temperature.

The ΔN value may also represent a comparison between the gold standard or average for a nutritional substance, and a particular or actual nutritional substance a consumer is considering purchasing. Accordingly, the attributes of a particular nutritional substance can be compared to the expected or optimal attributes of that type or category of nutritional substance. This allows a consumer to make more informed choices about the nutritional value of a substance a consumer is contemplating purchasing, or make informed decisions about preparation of the nutritional substance. For example, ΔN may represent a difference in the vitamin C content between on optimal orange that is picked when ripe from the vine, and an actual orange that a consumer is considering purchasing. In this example, if the consumer's orange was picked from the vine early, it may have both different surface physical characteristics that may be detectable by the sensors and methods described herein, and different vitamin C content. A database as described herein may include information regarding the physical attributes of an orange and how those factors correlate to the vitamin C content and other nutritional information. Accordingly, the systems disclosed herein may be able to determine the difference in vitamin C between a specific orange and the average vitamin C in oranges or the optimal vitamin C of, for example, an orange just picked from the vine when ripe. Accordingly, ripeness of tomatoes, water content, vitamin content, and other nutritional, organoleptic and/or aesthetic values may be compared for a specific, actual item a consumer is considering purchasing to the average or gold standard for that item. Accordingly, a consumer may then discern whether that particular item is providing at least an average or optimal nutrient, organoleptic and/or aesthetic value.

These differences may be presented in absolute value, for instance the difference in vitamin C, as a per unit weight value, as a graph comparing the present item versus an average curve for that specific item, or may be presented as a difference in nutritional content per unit price. For example, certain oranges or farmer's market produce may claim to have higher nutritional content because they are fresher or were harvested from the vines/roots closer in time to when the fruit ripened, leading to a higher nutritional content. However, these fruits tend to be higher in price, and accordingly, the system may be utilized to determine whether higher priced fruits are actually worth the higher price, and the amount of nutritional value gained per dollar difference. Accordingly, consumers could make informed choices based on quantitative data about whether and how much more nutritious more expensive fruit may be actually worth to the consumer.

In other examples, ΔN may represent the difference between the nutritional content of different subtypes of a broader category of nutritional substance. For instance, wild caught salmon is claimed to have up to 10 times greater omega three content than farm raised salmon. Accordingly, the present system could compare the nutritional content of a specific farm raised salmon to different types of wild caught salmon to determine the difference or ΔN in the omega three values. As described herein, this difference may be presented as an absolute value based on weight, an omega three difference per dollar, a per unit weight difference, or a graph indicating difference points including, average, optimum, and the current value of the fish on the graph.

Module 200 is the creation module. This can be a system, organization, or individual which creates and/or originates nutritional substances. Examples of this module include a farm which grows produce; a ranch which raises beef; an aquaculture farm for growing shrimp; a factory that synthesizes nutritional compounds; a collector of wild truffles; or a deep sea crab trawler.

Preservation module 300, described in co-pending application U.S. Ser. No. 13/888,353, titled "Preservation System for Nutritional Substances", and incorporated in its entirety by reference herein, is a preservation system for storing, preserving and protecting the nutritional substances created by creation module 200. Once the nutritional substance has been created, generally, it will need to be packaged in some manner for its transition to other modules in the nutritional substances industry 10. While preservation module 300 is shown in a particular position in the nutritional substance industry 10, following the creation module 200, it should be understood that the preservation module 300 actually can be placed anywhere nutritional substances need to be stored and preserved during their transition from creation to consumption. For instance, preservation module 300 may be placed after transformation module 400 but prior to conditioning module 500, to store the nutritional substance either in a retail establishment or in a consumer's household. This storage may include on a shelf, in a refrigerator, or in a freezer at a consumer residence, restaurant, grocery store or other retail establishment. It is understood that a nutritional substance may experience more than one preservation event, and that such preservation events may include the local storage of the nutritional substance, such as by a consumer prior to conditioning or consumption in addition to storage along the food processing chain.

A specific aspect of the present invention in achieving its goal related to ΔN information is to provide a system that tracks ΔN information during local storage or local preservation of a nutritional substance by a consumer. It is understood that a nutritional substance may experience more than one preservation event, and that such preservation events may include any known form of local storage or local preservation of a nutritional substance prior to conditioning and/or consumption, hereinafter referred to as local storage. Such local storage may take many forms, such as the storage of refrigerated items in a refrigerator, the storage of frozen items in a freezer, the storage of wine bottles in a wine-rack, the storage of canned or dry goods in a pantry, the storage of bread in a bread drawer, the storage of fruit in a counter top tray, and any other form of local nutritional substance storage known to those skilled in the art. It is understood that the present inventions include the local storage of consumable items such as medicaments, for example, medicaments stored in a refrigerator, medicaments stored in a medicine cabinet, or medicaments stored in any other known fashion.

Local storage according to the present invention can be enabled by local storage environments according to the present invention, such as a refrigerator, drawer, cabinet, portable cooler, and any other type of storage environment, wherein the local storage environment is provided with the same capabilities as the preservation module. In addition; local storage according to the present invention can be enabled by local storage containers according to the present invention, such as storage bags, trays, resalable storageware, jars, boxes, bottles, and any other type of storage environment, wherein the local storage container is provided with the same capabilities as the preservation module. In a further embodiment of the present invention, currently known traditional formats of storage environments and storage containers are enabled to provide local storage according to the present invention by being coupled with a coupon, hereinafter referred to as a local storage coupon, wherein the local storage coupon provides a traditional storage environment or traditional storage container with the same capabilities as the preservation module. The local storage coupon can be attached to, placed within, or in any known fashion coupled with, any known formats of traditional storage environments and traditional storage containers.

Transformation module 400 is a nutritional substance processing system, such as a manufacturer who processes raw materials such as grains into breakfast cereals. Transformation module 400 could also be a ready-to-eat dinner manufacturer who receives the components, or ingredients, also referred to herein as component nutritional substances, for a ready-to-eat dinner from preservation module 300 and prepares them into a frozen dinner. While transformation module 400 is depicted as one module, it will be understood that nutritional substances may be transformed by a number of transformation modules 400 on their path to consumption.

Conditioning module 500 is a consumer preparation system for preparing the nutritional substance immediately before consumption by the consumer. Conditioning module 500 can be a microwave oven, a blender, a toaster, a convection oven, toaster oven, a cook, etc. It can also be systems used by commercial establishments to prepare nutritional substance for consumers such as a restaurant, an espresso maker, pizza oven, and other devices located at businesses which provide nutritional substances to consumers. Such nutritional substances could be for consumption at the business or for the consumer to take out from the business. Conditioning module 500 can also be a combination of any of these devices used to prepare nutritional substances for consumption by consumers.

Consumer module 600 collects information from the living entity which consumes the nutritional substance which has passed through the various modules from creation to consumption. The consumer can be a human being, but could also be an animal, such as pets, zoo animals and livestock, which are they themselves nutritional substances for other consumption chains. Consumers could also be plant life which consumes nutritional substances to grow.

Information module 100 receives and transmits information regarding a nutritional substance between each of the modules in the nutritional substance industry 10 including, the creation module 200, the preservation module 300, the transformation module 400, the conditioning module 500, and the consumer module 600. The nutritional substance information module 100 can be an interconnecting information transmission system which allows the transmission of information between various modules. Information module 100 contains a database, also referred to herein as a dynamic nutritional value database, where the information regarding the nutritional substance resides, particularly ΔN for the nutritional substance. Information module 100 may also contain a massive database of physical attributes of known nutritional substances at known nutritional, organoleptic, and aesthetic states, also referred to herein as nutritional substance attribute library, which can be utilized for determining the identity and current nutritional, organoleptic, and aesthetic state of a nutritional substance. Information module 100 can be connected to the other modules by a variety of communication systems, such as paper, computer networks, the internet and telecommunication systems, such as wireless telecommunication systems. In a system capable of receiving and processing real time consumer feedback and updates regarding changes in the nutritional, organoleptic, and/or aesthetic value of nutritional substances, or ΔN, consumers can even play a role in updating a dynamic nutritional value database with observed or measured information about the nutritional substances they have purchased and/or prepared for consumption, so that the information is available and useful to others in the nutritional substance supply system, such as through reports reflecting the consumer input or through modification of ΔN.

In an embodiment of the present invention, such consumer feedback and updates related to ΔN information are provided during the local storage of a nutritional substance. In a preferred embodiment, such consumer feedback and updates related to ΔN information are obtained through, or provided by, local storage environments, local storage containers, and local storage coupons according to the present invention.

In some embodiments of the present invention, consumer feedback and updates regarding ΔN information may be obtainable from appliances that include the ability to display ΔN information, including ΔN information calculated based on a sensed physical attribute of the nutritional substance. The ΔN value may be calculated, represented, or displayed to a consumer as a per unit weight (e.g., ΔN per ounce, or ΔN per gram) format or value. The ΔN value may also represent a comparison between the gold standard or average for a particular nutritional substance, and a particular nutritional substance. Accordingly, the attributes of a particular nutritional substance can be compared to the expected or optimal attributes of that type or category of nutritional substance. This allows a consumer to make more informed choices about the nutritional value of a substance a consumer is contemplating purchasing, or make informed decisions about preparation of the nutritional substance. For instance, a scale or other weight measurement device, alone or incorporated into another appliance may be provided with the ability to detect the weight and calculate a ΔN based on a current weight of the nutritional substance and be interconnected to nutritional substance information module 100. Accordingly, a standalone scale may be provided with the ability to detect the weight of a nutritional substance, and display ΔN information to the consumer based on the current weight of the nutritional substance and provide that information to the nutritional substance information module 100. Accordingly, this information may be integrated with the other modules including conditioning module 500 and preservation module 300. Additionally, a scale or other weight sensor may be integrated into a variety of other appliances to provide the ability to display ΔN information to the consumer based on the current weight of a nutritional substance. Accordingly, a weight sensor may be integrated into a storage container, shelf, drawer, refrigerator, microwave, smartoven, oven, conditioner 570, local storage container, or any other appliances that store, condition or otherwise interact with nutritional substances. An example of an electronic scale is described in, for example, U.S. Pat. No. 6,538,215, issued on Mar. 25, 2003, titled Programmable Digital Scale, which is incorporated by reference herein in its entirety.

In some embodiments nutritional substances may be identified by detection of a nutritional substance's optical characteristics. For example, various products are available capable using optical technology to visually identify produce and other nutritional substances, and various other items. For example, an automated optical fruit recognition system developed by Fraunhofer is capable of detecting and identifying various produce optically as described by an article titled "Automated Fruit Recognition" available at http://www.isob.fraunhofer.de/servlet/is/33328/which is incorporated by reference herein in its entirety. Accordingly, the Fraunhofer system may be utilized to determine the identity of a nutritional substance by utilizing optical data detected from the nutritional substance. Accordingly, a user could then utilize their mobile phone or other devices with optical sensors to identify nutritional substances. Additionally, an optical object recognition system is disclosed in U.S. Pat. No. 6,310,964 that is described as capable of identifying produce and is incorporated herein by reference in its entirety.

Figure 2:
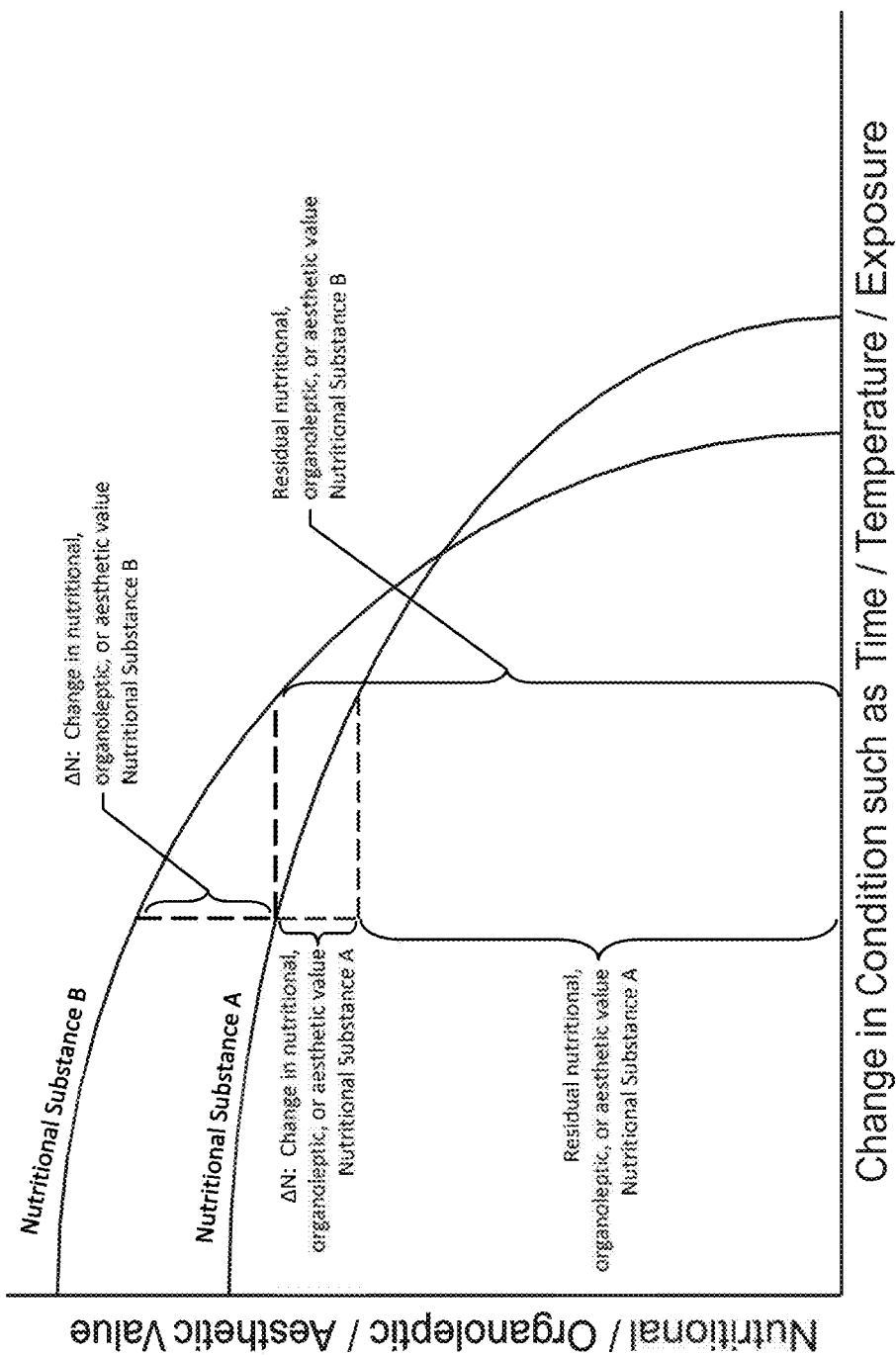
FIG. 2 shows a graph representing a value of a nutritional substance which changes according to a change of condition for the nutritional substance.

FIG. 2 is a graph showing the function of how a nutritional, organoleptic, or aesthetic value of a nutritional substance varies over the change in a condition of the nutritional substance. Plotted on the vertical axis of this graph can be either the nutritional value, organoleptic value, or even the aesthetic value of a nutritional substance. Plotted on the horizontal axis can be the change in condition of the nutritional substance over a variable such as time, temperature, location, and/or exposure to environmental conditions. This exposure to environmental conditions can include: exposure to air, including the air pressure and partial pressures of oxygen, carbon dioxide, water, or ozone; airborne chemicals, pollutants, allergens, dust, smoke, carcinogens, radioactive isotopes, or combustion byproducts; exposure to moisture; exposure to energy such as mechanical impact, mechanical vibration, irradiation, heat, or sunlight; or exposure to materials such as packaging. The function plotted as nutritional substance A could show a ΔN for milk, such as the degradation of a nutritional value of milk over time. Any point on this curve can be compared to another point on the same curve to measure and/or describe the change in nutritional value, or the ΔN, of nutritional substance A. The plot of the degradation in the same nutritional value of nutritional substance B, also milk, describes the change in nutritional value, or the ΔN, of nutritional substance B, a nutritional substance which starts out with a higher nutritional value than nutritional substance A, but degrades over time more quickly than nutritional substance A.

In this example, where nutritional substance A and nutritional substance B are milk, this ΔN information regarding the nutritional substance degradation profile of each milk could be used by the consumer in the selection and/or consumption of the milk. If the consumer has this information at time zero when selecting a milk product for purchase, the consumer could consider when the consumer plans to consume the milk, and whether that is on one occasion or multiple occasions. For example, if the consumer planned to consume the milk prior to the point when the curve represented by nutritional substance B crosses the curve represented by nutritional substance A, then the consumer should choose the milk represented by nutritional substance B because it has a higher nutritional value until it crosses the curve represented by nutritional substance A. However, if the consumer expects to consume at least some of the milk at a point in time after the time when the curve represented by nutritional substance B crosses the curve represented by nutritional substance A, then the consumer might choose to select the milk represented by the nutritional substance A, even though milk represented by nutritional substance A has a lower nutritional value than the milk represented by nutritional substance B at an earlier time. This change to a desired nutritional value in a nutritional substance over a change in a condition of the nutritional substance described in FIG. 2 can be measured and/or controlled throughout nutritional substance supply system 10 in FIG. 1. This example demonstrates how dynamically generated information regarding a ΔN of a nutritional substance, in this case a change in nutritional value of milk, can be used to understand a rate at which that nutritional value changes or degrades; when that nutritional value expires; and a residual nutritional value of the nutritional substance over a change in a condition of the nutritional substance, in this example a change in time. This ΔN information could further be used to determine a best consumption date for nutritional substance A and B, which could be different from each other depending upon the dynamically generated information generated for each.

Figure 10:
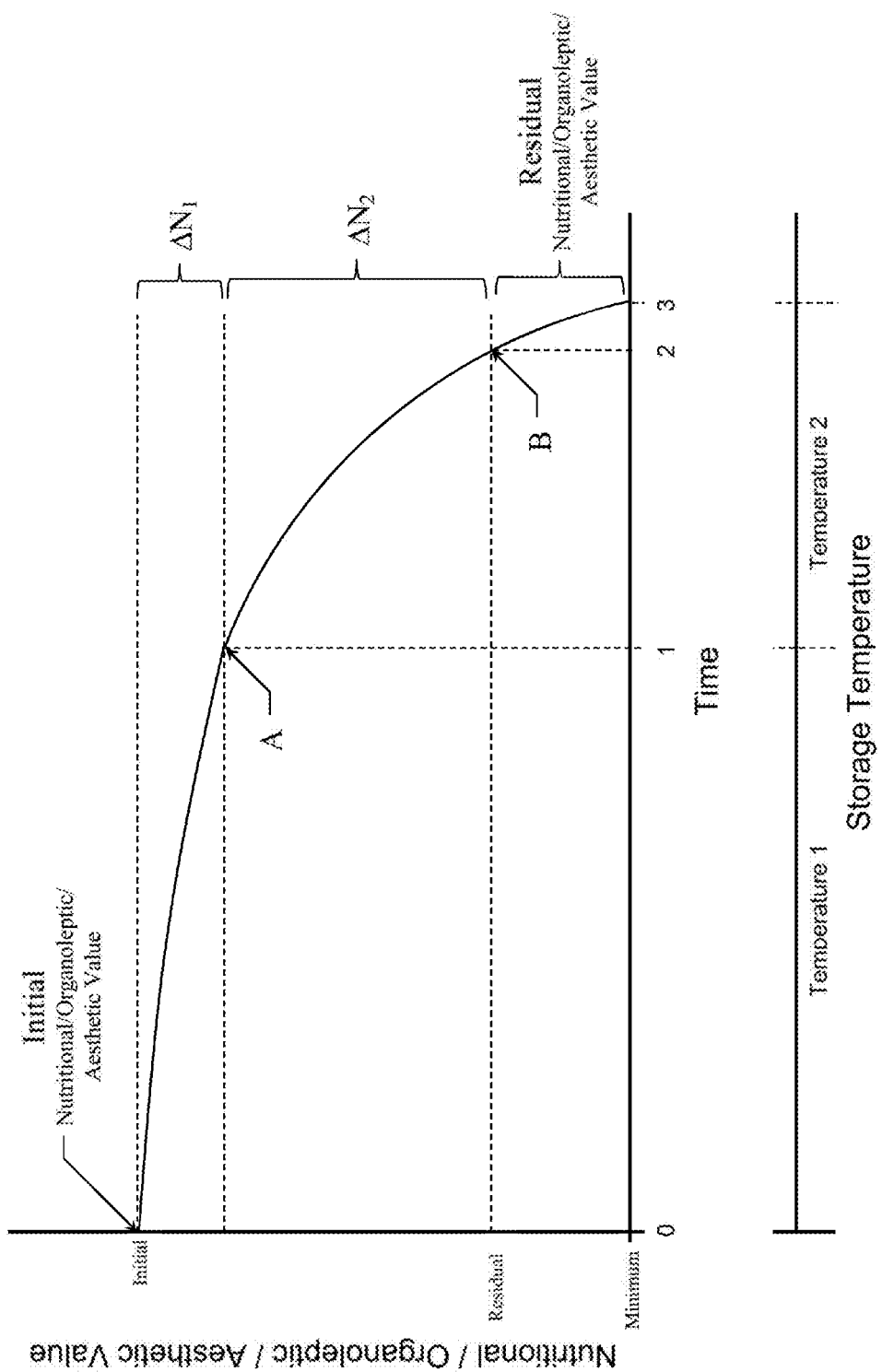
FIG. 10 shows a graph representing a value of a nutritional substance which changes according to changes in multiple conditions for the nutritional substance.

FIG. 10 is a graph showing the function of how a nutritional, organoleptic, or aesthetic value of a nutritional substance varies over a change in time and a change in a second condition, the storage temperature of the nutritional substance. It is understood that change in time and change in storage temperature are offered by way of example, and are in no way limiting to the types of condition changes to which the present inventions may be applied. As an example, the change in a nutritional property of milk is shown over a period of time including its preservation at the supermarket and a subsequent period of time including its local storage in a consumer's refrigerator, which is a local storage environment according to the present invention. The graph shows that the milk is preserved at a first temperature, Temperature 1, for a first period of time indicated as 0 to 1, while at the supermarket. The milk is purchased by a consumer at time 1, and subsequently stored at a second temperature, Temperature 2, for a second period of time indicated as 1 to 3, during local storage in the refrigerator, which is a local storage environment according to the present invention. It is noted that Temperature 2 is greater than Temperature 1, and accordingly the shape of the graph changes at point A when the milk is taken from Temperature 1 and stored at Temperature 2. As in the preservation module, the local storage environment can identify the milk stored within it by reading or scanning its dynamic information identifier (or by the consumer entering it), can communicate with the nutritional substance information module, and accordingly can determine the milk's $\Delta N$ prior to placement within the refrigerator, and continue to track the milk's $\Delta N$ while in the refrigerator. The refrigerator is provided with a consumer interface, such as a screen, keyboard, sound system, or any known consumer interface. The consumer interface enables the refrigerator to communicate to the consumer that it contains the particular carton of milk, information related to $\Delta N$, including current nutritional, organoleptic, and aesthetic values of the milk, and when the milk will reach a minimum acceptable nutritional, organoleptic, or aesthetic value, indicated by "Minimum" on the vertical axis of the graph. The minimum acceptable values may be automatically provided by the information module, may be provided by the consumer through the consumer interface, or may be the higher of the two values. In this case the consumer can see how the nutritional value of the milk has degraded prior to purchasing it, and can continue to see how the nutritional value degrades during local storage after its purchase, and when it will reach its minimum acceptable nutritional value. For example, at the time indicated as 2, the consumer can determine the residual nutritional value of the milk, corresponding to point B and "Residual" on the vertical axis of the graph. Further, the consumer can determine the milk's nutritional value will reach a minimum acceptable level at time 3, as indicated by "Minimum" on the vertical axis of the graph, thus knowing the window of time in which the milk will maintain an acceptable nutritional level, as indicated by time 1 to 3. Further, the refrigerator can notify the consumer through its consumer interface when the milk's nutritional value has reached or fallen below the minimum acceptable value.

In fact, if the consumer knows the internal temperature of his own refrigerator prior to purchasing the milk, he can predict the degradation of nutritional value of the milk that will occur after he purchases it and locally stores it in his refrigerator, thus knowing the window of time in which it will maintain an acceptable nutritional level, as indicated by time 1 to 3. For example, the consumer may utilize an application on his smartphone to store, or even monitor, the internal temperature of his refrigerator. When he goes to the supermarket, he could scan the milk's dynamic information identifier with his smartphone, and the application can communicate with the nutritional substance information module to determine a current $\Delta N$, and predict the $\Delta N$ of the milk when stored in his refrigerator. Further, the consumer may utilize such an application on his smartphone to store, or even monitor, the internal conditions of various local storage environments, local storage containers, and local storage coupons. In this way, when he goes to the supermarket, he can scan the dynamic information identifier of a wide variety of nutritional substances with his smartphone, and the application can communicate with the nutritional substance information module to determine a current $\Delta N$, and predict the $\Delta N$ of the nutritional substance when stored in the corresponding local storage environment or local storage container. In other embodiments, the consumer may place the milk, on a scale or other weight measurement device that allows the consumer to determine the current $\Delta N$ based on the weight of the milk left in the carton and the dynamic information identifier. For instance, the scale may have its own reader, or may be wirelessly connected to a smartphone that reads the identifier, and sends the data to a remote server or directly to the scale to combine with the weight data to determine the current $\Delta N$.

Figure 11:
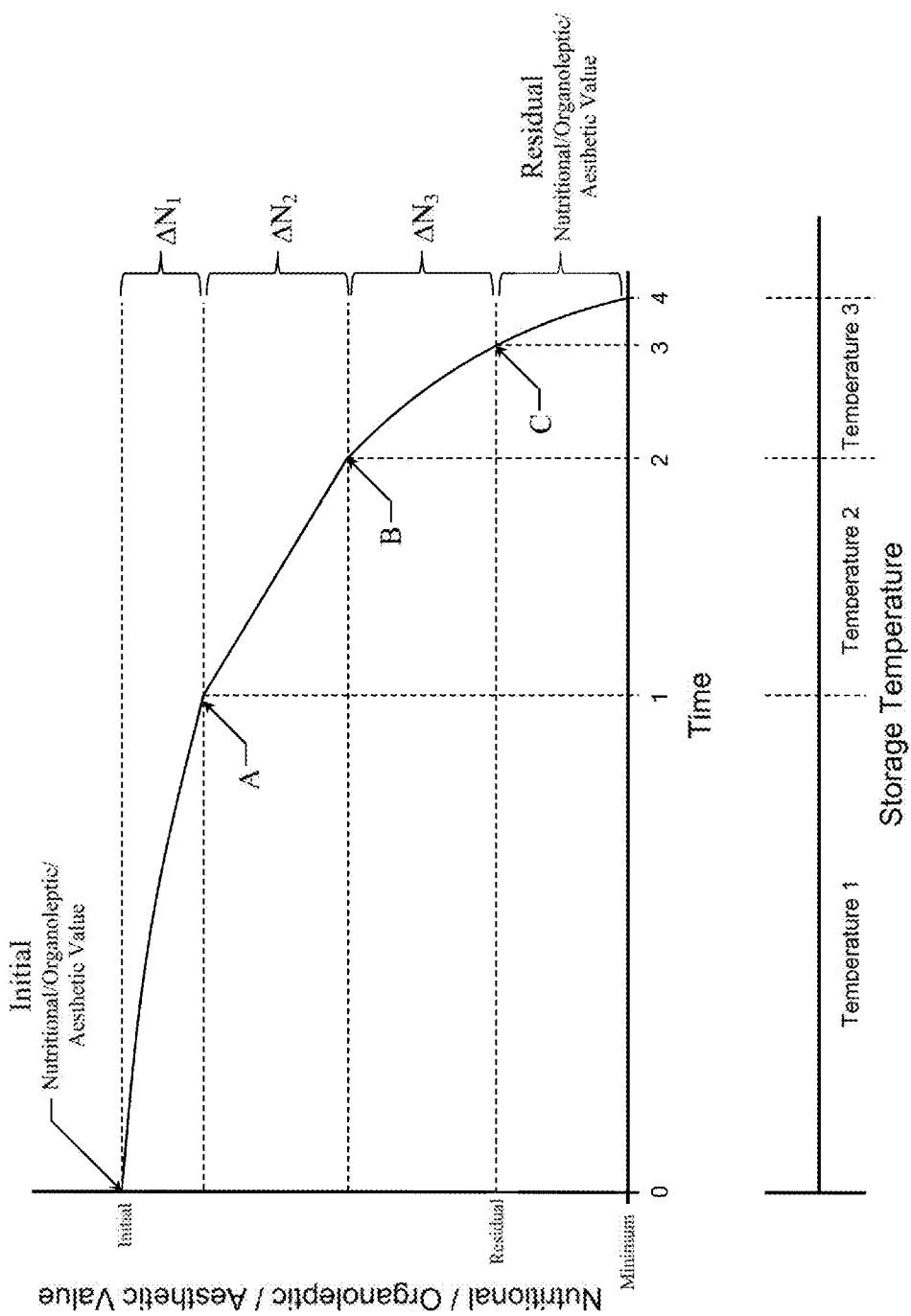
FIG. 11 shows a graph representing a value of a nutritional substance which changes according to changes in multiple conditions for the nutritional substance.

FIG. 11 is a graph showing the function of how a nutritional, organoleptic, or aesthetic value of a nutritional substance varies over a change in time and multiple changes in a second condition, the storage temperature of the nutritional substance. It is understood that change in time and change in storage temperature are offered by way of example, and are in no way limiting to the types on condition changes to which the present inventions may be applied. In this example, the change in a nutritional property of potato salad is shown over a period of time including its preservation at the supermarket and a subsequent period of time including its local storage in a consumer's refrigerator, which is a local storage environment according to the present invention, and subsequent storage in the consumer's picnic cooler, which contains a local storage coupon according to the present invention. The graph shows that the potato salad is preserved at a first temperature, Temperature 1, for a first period of time indicated as 0 to 1, while at the supermarket. The potato salad is purchased by a consumer at time 1, and subsequently stored at a second temperature, Temperature 2, for a second period of time indicated as 1 to 2, during local storage in the consumer's refrigerator, which is a local storage environment according to the present invention. It is noted that Temperature 2 is greater than Temperature 1, and accordingly the shape of the graph changes at point A when the potato salad is taken from Temperature 1 and stored at Temperature 2. As in the preservation module, the local storage environment can identify the potato salad stored within it by reading or scanning its dynamic information identifier (or by the consumer entering it), can communicate with the nutritional substance information module, and accordingly can determine the potato salad's $\Delta N$ prior to placement within the refrigerator, and continue to track the potato salad's $\Delta N$ while in the refrigerator. The refrigerator is provided with a consumer interface, such as a screen, keyboard, sound system, or any known consumer interface. Alternatively, an application on the consumer's smartphone can enable the refrigerator to communicate with the smartphone such that the smartphone acts as the consumer interface. The consumer interface enables the refrigerator to communicate to the consumer that it contains the particular container of potato salad, information related to $\Delta N$, including current nutritional, organoleptic, and aesthetic values of the potato salad while stored in the refrigerator. At time 2, the potato salad is taken from the refrigerator and placed inside the consumer's traditional picnic cooler, along with a coupon according to the present invention, where it is stored at Temperature 3, for a period of time indicated as 2 to 4. It is noted that Temperature 3 is greater than Temperature 2, and accordingly the shape of the graph changes at point B when the potato salad is taken from Temperature 2 and stored at Temperature 3. The local storage coupon can identify the potato salad stored within it by reading or scanning its dynamic information identifier (or by the consumer entering it), can communicate with the nutritional substance information module, and accordingly can determine the potato salad's $\Delta N$ prior to placement within the cooler, and continue to track the potato salad's $\Delta N$ while in the cooler. The coupon is provided with a consumer interface, such as a screen, keyboard, sound system, or any known consumer interface, or alternatively, an application on the consumer's smartphone can enable the coupon to communicate with the smartphone such that the smartphone acts as the consumer interface. The consumer interface enables the coupon to communicate to the consumer that the cooler contains the particular container of potato salad, information related to $\Delta N$, including current nutritional, organoleptic, and aesthetic values of the potato salad while stored in the cooler, and when the potato salad will reach a minimum acceptable nutritional, organoleptic, or aesthetic value, indicated by "Minimum" on the vertical axis of the graph. The minimum acceptable values may be automatically provided by the information module, may be provided by the consumer through the consumer interface, or may be the higher of the two values. In this case the consumer can see how the nutritional value of the potato salad has degraded prior to placing it in the cooler with the coupon, and can continue to see how the nutritional value degrades during local storage in the cooler, and when it will reach its minimum acceptable nutritional value. For example, at the time indicated as 3, the consumer can determine the residual nutritional value of the potato salad, corresponding to point C and "Residual" on the vertical axis of the graph. Further, the consumer can determine the potato salad's nutritional value will reach a minimum acceptable level at time 4, as indicated by "Minimum" on the vertical axis of the graph, thus knowing the window of time in which the potato salad in the cooler will maintain an acceptable nutritional level, as indicated by time 2 to 4. Further, the coupon can notify the consumer through the consumer interface when the potato salad's nutritional value has reached or fallen below the minimum acceptable value.

In some embodiments the nutritional substance, for example turkey, may be removed from the local storage or coupon and a portion of the nutritional substance placed on a scale, or another appliance that includes a weight measurement apparatus to sense the weight of the amount nutritional substance, and display $\Delta N$ information relating to that amount. In other embodiments, the local storage may contain a weight measurement apparatus. This allows the consumer to determine $\Delta N$ information for a portion of the nutritional substance the consumer may plan on eating that is less than the entire portion stored or purchased. For example, an oven or microwave may be provided that allows a consumer to place a portion of the turkey in the oven or microwave, and a scale or other weight measurement apparatus may be included that determines the amount of turkey removed, and $\Delta N$ information for that turkey. In some embodiments, the oven or microwave may then communicate different conditioning or cooking options that result in different $\Delta Ns$ based on information in the database regarding cooking or conditioning regimes. For example, microwaving the turkey at a lower temperature for longer may retain more of the amino acid chains in a non-denatured and nutritionally viable form than microwaving the turkey at the highest setting for a short time. Accordingly, these different conditioning options may be displayed to the consumer together with the resultant $\Delta Ns$ for each option and the final nutritional values that would result from selecting each option. This may also include the choice for the consumer regarding the type (e.g. oven or microwave) of conditioning and the associated $\Delta Ns$ that would result from those options. In addition, these $\Delta Ns$ may be displayed to the consumer as graphs.

It is understood that local storage environments according to the present invention can comprise any local storage environment for a nutritional substance provided with the features enabling it to identify a dynamic information identifier on the nutritional substance, track one or more conditions related to a $\Delta N$ of the nutritional substance, communicate with the nutritional substance information module, determine a current $\Delta N$, such as by the use of any known environmental or nutritional substance attribute sensor including a weight measurement sensor or scale, track and predict the $\Delta N$ of the nutritional substance while stored therein, and communicate information related to the $\Delta N$ to a consumer. In some embodiments, a standalone scale may be provided for removing the nutritional substance from the local storage environment and determining the weight of all or a portion of the nutritional substance in preparation for conditioning or consumption in order to determine the $\Delta N$ of the portion of nutritional substance removed from the local storage environment. Examples of such local storage environments include, but are not limited to: a pantry capable of identifying a dynamic information identifier on canned or bottled goods and tracking one or more conditions related to a $\Delta N$ of the canned or bottled goods, such as time, storage temperature, and weight; a shelf capable of identifying a dynamic information identifier on dry goods and tracking one or more conditions related to a $\Delta N$ of the dry goods, such as time, storage humidity and weight; a vegetable bin capable of identifying a dynamic information identifier on vegetables and tracking one or more conditions related to a $\Delta N$ of the vegetables, such as time, storage temperature, gaseous or volatile emissions from the vegetables, color of the vegetables, weight, and storage humidity; a drawer capable of identifying a dynamic information identifier on fruit and tracking one or more conditions related to a $\Delta N$ of the fruit, such as time, storage temperature, gaseous or volatile emissions from the fruit, weight, color of the fruit, and exposure to light; a medicine cabinet capable of identifying a dynamic information identifier on medicaments and tracking one or more conditions related to a $\Delta N$ of the medicaments, such as time, storage temperature, storage humidity, weight and exposure to light; a standalone scale capable of identifying a dynamic information identifier on a nutritional substance or optically identifying the substance itself and determining the weight of the nutritional substance in order to calculate a $\Delta N$. These local storage environments or standalone scales may be provided with a consumer interface, such as a screen, keyboard, sound system, or any known consumer interface. Standalone scales include any freestanding electronic scale that is capable of detecting the weight of a nutritional substance and outputting that weight to the nutritional substance information module 100 or other components of the system to determine a $\Delta N$ and display that a $\Delta N$ to the consumer. In some embodiments weight or mass determination may be utilized by an optical object recognition system, in place of or in addition to a scale. For example, various products are available that are capable of using optical technology to visually identify produce and other nutritional substances, and various other items. For example, an automated optical fruit recognition system developed by Fraunhofer is capable of detecting and identifying various produce optically as described by an article titled "Automated Fruit Recognition" available at http://www.isob.fraunhofer.de/servlet/is/33328/which is incorporated by reference herein in its entirety. Accordingly, a user could then utilize their mobile phone or other devices with optical sensors to identify nutritional substances. Additionally, an optical object recognition system is disclosed in U.S. Pat. No. 6,310,964 that is described as capable of detecting identity of produce and is incorporated herein by reference in its entirety An application on the consumer's smartphone can enable these local storage environments or standalone scales to communicate with the smartphone such that the smartphone acts as the consumer interface. The consumer interface enables the local storage environment or standalone scale to communicate to the consumer that it contains a particular nutritional substance, information related to its ΔN including a ΔN based on the weight of the nutritional substance, including current nutritional, organoleptic, and aesthetic values of the nutritional substance while stored in the local storage environment. In some embodiments, the local storage environment may be placed directly on the scale in order to determine the weight of the nutritional substance inside the local storage environment.

It is understood that local storage containers according to the present invention can comprise any local storage container for a nutritional substance provided with the features enabling it to identify a dynamic information identifier on the nutritional substance, track one or more conditions related to a ΔN of the nutritional substance, communicate with the nutritional substance information module, determine a current ΔN, such as by the use of any known environmental or nutritional substance attribute sensor, track and predict the ΔN of the nutritional substance while stored therein, and communicate information related to the ΔN to a consumer. Examples of such local storage containers include, but are not limited to: a plastic, sealable container capable of identifying a dynamic information identifier on dry goods and tracking one or more conditions related to a ΔN of the dry goods, such as time, gaseous or volatile emissions from the dry goods, weight, color of the dry goods, and storage humidity; a tray capable of identifying a dynamic information identifier on fruit and tracking one or more conditions related to a ΔN of the fruit, such as time, gaseous or volatile emissions from the fruit, color of the fruit, weight, storage temperature, and exposure to light; a resalable bag capable of identifying a dynamic information identifier on vegetables and tracking one or more conditions related to a ΔN of the vegetables, such as time, storage temperature, gaseous or volatile emissions from the vegetables, color of the vegetables, and storage humidity; a purse capable of identifying a dynamic information identifier on a medicament and tracking one or more conditions related to a ΔN of the medicament, such as time, storage temperature, storage humidity, and exposure to light; a picnic cooler capable of identifying a dynamic information identifier on potato salad and tracking one or more conditions related to a ΔN of the potato salad, such as time, gaseous or volatile emissions from the potato salad, weight, color of the potato salad, and storage temperature. These local storage containers may be provided with a consumer interface, such as a screen, keyboard, sound system, or any known consumer interface. Alternatively, an application on the consumer's smartphone can enable these local storage containers to communicate with the smartphone such that the smartphone acts as the consumer interface. The consumer interface enables the local storage container to communicate to the consumer that it contains a particular nutritional substance, information related to its ΔN, including current nutritional, organoleptic, and aesthetic values of the nutritional substance while stored in the local storage container.

It is understood that local storage coupons according to the present invention can comprise any form of tag, badge, transponder, label, or any other device, individually and collectively referred to herein as a coupon, placed in proximity to a traditional local storage environment or traditional local storage container, and capable of identifying a dynamic information identifier on a nutritional substance stored in the traditional local storage environment or traditional local storage container, tracking one or more conditions related to a ΔN of the nutritional substance, communicating with the nutritional substance information module, determining a current ΔN, such as by the use of any known environmental or nutritional substance attribute sensor, tracking and predicting the ΔN of the nutritional substance, and communicating information related to the ΔN to a consumer. Examples of such local storage coupons include, but are not limited to: a coupon placed in a plastic container with dry goods, wherein the coupon is capable of identifying a dynamic information identifier on dry goods and tracking one or more conditions related to a ΔN of the dry goods, such as time, gaseous or volatile emissions from the dry goods, color of the dry goods, weight, and storage humidity; a coupon placed on a tray for holding fruit, wherein the coupon is capable of identifying a dynamic information identifier on fruit and tracking one or more conditions related to a ΔN of the fruit, such as time, storage temperature, gaseous or volatile emissions from the fruit, color of the fruit, and exposure to light; a coupon placed within a resalable vegetable bag, wherein the coupon is capable of identifying a dynamic information identifier on vegetables and tracking one or more conditions related to a ΔN of the vegetables, such as time, storage temperature, gaseous or volatile emissions from the vegetables, weight, color of the vegetables, and storage humidity; a coupon placed within a purse, wherein the coupon is capable of identifying a dynamic information identifier on a medicament placed within the purse and tracking one or more conditions related to a ΔN of the medicament, such as time, storage temperature, storage humidity, and exposure to light; a coupon attached to the inner surface of a picnic cooler, wherein the coupon is capable of identifying a dynamic information identifier on potato salad stored in the cooler and tracking one or more conditions related to a ΔN of the potato salad, such as time, gaseous or volatile emissions from the potato salad, color of the potato salad, and storage temperature; a coupon hung in a pantry, wherein the coupon is capable of identifying a dynamic information identifier on canned or bottled goods and tracking one or more conditions related to a ΔN of the canned or bottled goods, such as time, exposure to light (in the case of bottled goods), and storage temperature; a coupon attached to a shelf, wherein the coupon is capable of identifying a dynamic information identifier on dry goods and tracking one or more conditions related to a ΔN of the dry goods, such as time, gaseous or volatile emissions from the dry goods, color of the dry goods, weight, and storage humidity; a coupon attached to an inner surface of a vegetable bin, wherein the coupon is capable of identifying a dynamic information identifier on vegetables and tracking one or more conditions related to a ΔN of the vegetables, such as time, gaseous or volatile emissions from the vegetables, weight, color of the vegetables, storage temperature, and storage humidity; a coupon placed within a drawer, wherein the coupon is capable of identifying a dynamic information identifier on fruit and tracking one or more conditions related to a ΔN of the fruit, such as time, gaseous or volatile emissions from the fruit, color of the fruit, storage temperature, and exposure to light; a coupon attached to the inner surface of a medicine cabinet, wherein the coupon is capable of identifying a dynamic information identifier on medicaments and track one or more conditions related to a ΔN of the medicaments, such as time, storage temperature, storage humidity, and exposure to light.

In FIG. 1, Creation module 200 can dynamically encode nutritional substances to enable the tracking of changes in nutritional, organoleptic, and/or aesthetic value of the nutritional substance, or ΔN. This dynamic encoding, also referred to herein as a dynamic information identifier, can replace and/or complement existing nutritional substance marking systems such as barcodes, labels, and/or ink markings. This dynamic encoding, or dynamic information identifier, can be used to make nutritional substance information from creation module 200 available to information module 100 for use by preservation module 300, transformation module 400, conditioning module 500, and/or consumption module 600, which includes the ultimate consumer of the nutritional substance. One method of marking the nutritional substance with a dynamic information identifier by creation module 200, or any other module in nutritional supply system 10, could include an electronic tagging system, such as the tagging system manufactured by Kovio of San Jose, Calif., USA. Such thin film chips can be used not only for tracking nutritional substances, but can include components to measure attributes of nutritional substances, and record and transmit such information. Such information may be readable by a reader including a satellite-based system. Such a satellite-based nutritional substance information tracking system could comprise a network of satellites with coverage of some or all the surface of the earth, so as to allow the dynamic nutritional value database of information module 100 real time, or near real time updates about a ΔN of a particular nutritional substance.

Preservation module 300 includes packers and shippers of nutritional substances. The tracking of changes in nutritional, organoleptic, and/or aesthetic values, or a ΔN, during the preservation period within preservation module 300 allows for dynamic expiration dates for nutritional substances. For example, expiration dates for dairy products are currently based generally only on time using assumptions regarding minimal conditions at which dairy products are maintained. This extrapolated expiration date is based on a worst-case scenario for when the product becomes unsafe to consume during the preservation period. In reality, the degradation of dairy products may be significantly less than this worst-case. If preservation module 300 could measure or derive the actual degradation information such as ΔN, an actual expiration date, referred to herein as a dynamic expiration date, can be determined dynamically, and could be significantly later in time than an extrapolated expiration date. This would allow the nutritional substance supply system to dispose of fewer products due to expiration dates. This ability to dynamically generate expiration dates for nutritional substances is of particular significance when nutritional substances contain few or no preservatives. Such products are highly valued throughout nutritional substance supply system 10, including consumers who are willing to pay a premium for nutritional substances with few or no preservatives.

It should be noted that a dynamic expiration date need not be indicated numerically (i.e., as a numerical date) but could be indicated symbolically as by the use of colors—such as green, yellow and red employed on semaphores—or other designations. In those instances, the dynamic expiration date would not be interpreted literally but, rather, as a dynamically-determined advisory date. In practice a dynamic expiration date will be provided for at least one component of a single or multi-component nutritional substance. For multi-component nutritional substances, the dynamic expiration date could be interpreted as a "best' date for consumption for particular components.

By law, in many localities, food processors such as those in transformation module 400 are required to provide nutritional substance information regarding their products. Often, this information takes the form of a nutritional table applied to the packaging of the nutritional substance. Currently, the information in this nutritional table is based on averages or minimums for their typical product. Using the nutritional substance information from information module 100 provided by creation module 200, preservation module 300, and/or information from the transformation of the nutritional substance by transformation module 400, and consumer feedback and updates related to ΔN, preferably obtained through or provided by local storage environments, appliances, scales and other weight measurement devices, local storage containers, and local storage coupons according to the present invention, the food processor could include a dynamically generated nutritional value table, also referred to herein as a dynamic nutritional value table, for the actual nutritional substance being supplied to a consumer and further being locally stored by the consumer. The information in such a dynamic nutritional value table could be used by conditioning module 500 in the preparation of the nutritional substance, and/or used by consumption module 600, so as to allow the ultimate consumer the ability to select the most desirable nutritional substance which meets their needs, and/or to track information regarding nutritional substances consumed.

Information about changes in nutritional, organoleptic, and/or aesthetic values of nutritional substances, or ΔN, is particularly useful in the conditioning module 500 of the present invention, as it allows knowing, or estimating, the pre-conditioning state of the nutritional, organoleptic, and/or aesthetic values of the nutritional substance, including the changes in nutritional, organoleptic, and/or aesthetic values occurring during local storage of the nutritional substance, and further allows for estimation of a ΔN associated with proposed conditioning parameters. The conditioning module 500 can therefore create conditioning parameters, such as by modifying existing or baseline conditioning parameters, to deliver desired nutritional, organoleptic, and/or aesthetic values after conditioning. The pre-conditioning state of the nutritional, organoleptic, and/or aesthetic value of a nutritional substance is not tracked or provided to the consumer by existing conditioners, nor is the ΔN expected from a proposed conditioning tracked or provided to the consumer either before or after conditioning. However, using information provided by information module 100 from creation module 200, preservation module 300, transformation module 400, and consumer feedback and updates related to ΔN, preferably obtained through or provided by local storage environments, local storage containers, and local storage coupons according to the present invention, and/or information measured or generated by conditioning module 500 prior to conditioning, and/or consumer input provided through the conditioning module 500 prior to conditioning, conditioning module 500 could provide the consumer with adaptively developed conditioning parameters responsive to the current ΔN of the nutritional substance and the consumer's input, and the estimated or expected ΔN that will result from the adaptive conditioning parameters, and the corresponding residual nutritional, organoleptic, or aesthetic value.

In a further embodiment, the conditioner is provided with various sensors which can be used to sense attributes of a nutritional substance prior to conditioning, wherein the sensed attribute values can be used in determining a current ΔN or corresponding residual nutritional, organoleptic, or aesthetic value of the nutritional substance. In yet a further embodiment, some or all of the various sensors can be used to sense attributes of the nutritional substance during conditioning, so as to determine intra-conditioning ΔN information regarding the nutritional substance during its conditioning. Such intra-conditioning ΔN information provides closed loop feedback to the conditioner's controller regarding the adaptive conditioning parameters being implemented. If the closed-loop feedback indicates that the adaptive conditioning parameters will achieve desired residual nutritional, organoleptic, and aesthetic values, the conditioner's controller will continue to implement the adaptive conditioning parameters. However, if the closed-loop feedback indicates that the adaptive conditioning parameters will not achieve desired residual nutritional, organoleptic, and aesthetic values, the conditioner's controller will modify the adaptive conditioning parameters and implement the modified adaptive conditioning parameters. In the same fashion, the sensors can continue to provide closed-loop feedback to indicate that currently implemented conditioning parameters will, or will not, achieve desired residual nutritional, organoleptic, and aesthetic values, and accordingly, the conditioner may continue to implement the current conditioning parameters, or modify the current conditioning parameters and implement the modified parameters.

An important benefit provided by local storage environments, local storage containers, and local storage coupons of the present invention is that consumer feedback and updates related to ΔN, such as observed or measured information of, or related to, a ΔN during local storage of the nutritional substance is obtained through, or provided by, the local storage environments, containers, and coupons. In this way consumer feedback and updates related to a ΔN during local storage of a nutritional substance can play a role in updating the dynamic nutritional value information about the nutritional substances consumers have purchased and placed in local storage, such as through modification of ΔN. Such information regarding the change to nutritional, organoleptic and/or aesthetic value of the nutritional substance, or ΔN, could be provided not only to a consumer through the consumption module 600 and conditioning module 500, but could also be provided to information module 100 for use by creation module 200, preservation module 300, transformation module 400, so as to track, and possibly improve nutritional substances throughout the entire nutritional substance supply system 10.

In a further embodiment, the local storage environments, local storage containers, scales, and local storage coupons are provided with various nutritional substance attribute sensors which can be used to sense attributes of a nutritional substance prior to local storage, wherein the sensed attribute data can be used in determining the nutritional substance content and an initial nutritional, organoleptic, or aesthetic value of the nutritional substance, such as when the nutritional substance is placed into the local storage environment or container. In yet a further embodiment, some or all of the various nutritional substance attribute sensors can be used to sense attributes of the nutritional substance during local storage, so as to determine intra-local storage ΔN information regarding the nutritional substance during its local storage. In a case wherein the local storage environment or container is provided with a controller which can modify the storage parameters, so as to modify the storage conditions, of the local storage environment or container, such intra-local storage ΔN information can provide closed loop feedback to the local storage controller regarding the currently implemented storage parameters. In this way, if the closed-loop feedback indicates that the currently implemented storage parameters will achieve desired rates of change in residual nutritional, organoleptic, and aesthetic values, the controller will continue to implement the currently implemented storage parameters. Such desired rates of change in residual nutritional, organoleptic, and aesthetic values may be predetermined, such as by the nutritional substance provider, may be determined by consumer input, such as provided through a consumer interface of the local storage environment, container, or coupon, or may be established in any known fashion. If the closed-loop feedback indicates that the currently implemented parameters will not achieve desired rates of change in residual nutritional, organoleptic, and aesthetic values, the controller will adaptively modify the storage parameters and implement the adaptively modified storage parameters. In the same fashion, the sensors can continue to provide closed-loop feedback to the controller regarding any current storage parameters, and depending upon whether the current storage parameters will, or will not, achieve desired rates of change in residual nutritional, organoleptic, and aesthetic values, the controller may continue to implement the current storage parameters, or adaptively modify the current storage parameters and implement the adaptively modified storage parameters.

In the embodiment above, the local storage environments, containers, scales, and coupons are provided with the ability to communicate the sensed attribute data with an alternate database that facilitates identification of the nutritional substance content and current nutritional, organoleptic, or aesthetic value. The alternate database consists of a massive library of nutritional substance attribute data, related to the visual appearance, taste, smell, texture, touch, chemical composition and any other known physical attributes, referenced to corresponding nutritional, organoleptic, and aesthetic states of known nutritional substances, and is herein referred to as the nutritional substance attribute library. The various nutritional substance attribute sensors may include, but are not limited to, sensors capable of measuring and collecting data regarding visual appearance, taste, smell, volatiles, texture, touch, sound, chemical composition, temperature, weight, volume, density, hardness, viscosity, surface tension, and any other known physical attribute of the nutritional substance. These may include, but are not limited to, optical sensors, spectrometers, biosensors, laser sensors, cameras, electric noses, microphones, olfactory sensors, surface topography measurement equipment, three dimensional measuring equipment, chemical assays, hardness measuring equipment, ultrasound equipment, impedance detectors, temperature measuring equipment, weight measurement equipment including scales, and any known sensor capable of providing data regarding a physical attribute of a nutritional substance. It is understood that such local storage environments, containers, and coupons may also be provided with a nutritional substance reader, such that they can interact with nutritional substances provided with, and without, dynamic information identifiers. The nutritional substance attribute library may be separate from a nutritional substance industry database, or is preferably part of the nutritional substance industry database. Further, the nutritional substance attribute library may be separate from a nutritional substance database, or may exist within the nutritional substance database. In a preferred embodiment, the nutritional substance attribute library coexists with the nutritional substance database, a recipe database, and a consumer database, within the nutritional substance industry database.

The information regarding nutritional substances provided by information module 100 to consumption module 600 can replace or complement existing information sources such as recipe books, food databases like www.epicurious.

com, and Epicurious apps. Through the use of specific information regarding a nutritional substance from information module 100, consumers can use consumption module 600 to select nutritional substances according to nutritional, organoleptic, and/or aesthetic values. This will further allow consumers to make informed decisions regarding nutritional substance additives, preservatives, genetic modifications, origins, traceability, and other nutritional substance attributes that may also be tracked through the information module 100. This information can be provided by consumption module 600 through personal computers, laptop computers, tablet computers, and/or smartphones. Software running on these devices can include dedicated computer programs, modules within general programs, and/or smartphone apps. An example of such a smartphone app regarding nutritional substances is the iOS ShopNoGMO from the Institute for Responsible Technology. This iPhone app allows consumers access to information regarding non-genetically modified organisms they may select. Additionally, consumption module 600 may provide information for the consumer to operate conditioning module 500 in such a manner as to optimize nutritional, organoleptic, and/or aesthetic values of a nutritional substance and/or component nutritional substances thereof, according to the consumer's needs or preference or according to target values established by the provider of the nutritional substance, such as the transformer, and/or minimize degradation of, preserve, or improve nutritional, organoleptic, and/or aesthetic value of a nutritional substance and/or component nutritional substances thereof.

Through the use of nutritional substance information available from information module 100 nutritional substance supply system 10 can track nutritional, organoleptic, and/or aesthetic value. Using this information, nutritional substances travelling through nutritional substance supply system 10 can be dynamically valued and priced according to nutritional, organoleptic, and/or aesthetic values. For example, nutritional substances with longer dynamic expiration dates (longer shelf life) may be more highly valued than nutritional substances with shorter expiration dates. Additionally, nutritional substances with higher nutritional, organoleptic, and/or aesthetic values may be more highly valued, not just by the consumer, but also by each entity within nutritional substance supply system 10. This is because each entity will want to start with a nutritional substance with higher nutritional, organoleptic, and/or aesthetic value before it performs its function and passes the nutritional substance along to the next entity. Therefore, both the starting nutritional, organoleptic, and/or aesthetic value and the $\Delta N$ associated with those values are important factors in determining or estimating an actual, or residual, nutritional, organoleptic, and/or aesthetic value of a nutritional substance, and accordingly are important factors in establishing dynamically valued and priced nutritional substances.

The use of appliances, local storage environments, local storage containers, scales, and local storage coupons according to the present invention makes information related to a $\Delta N$ of a locally stored nutritional substance available to information module 100, so that information available from information module 100 can enable a consumer, or any entity inside or outside the nutritional substance supply system 10, to track nutritional, organoleptic, and/or aesthetic value of the nutritional substance during its local storage or prior to consumption or conditioning. It is understood that such local storage includes local storage by any entity that prepares or otherwise conditions nutritional substances for consumption by a consumer, and could include the consumer's residence, a restaurant, a hospital, a sports arena, a vending machine, or any other known entity providing nutritional substances for consumption.

Additionally, the use of appliances that can display or calculate current $\Delta N$ information based on sensed attributes, including weight, allows a consumer to determine the current $\Delta N$ of a portion of the stored nutritional substance prior to conditioning or consumption. This ability may be incorporated into any appliance, or may be as a standalone scale or weight measurement apparatus, with a dynamic information identifier reader, or the ability wirelessly link with a consumer's smartphone. Additionally, the weight measurement device or sensors may be incorporated into ovens, smartovens, microwaves, refrigerators, or any other appliance.

During the period of implementation of the present inventions, there will be nutritional substances being marketed including those benefiting from the tracking of dynamic nutritional information such as $\Delta N$, also referred to herein as information-enabled nutritional substances, and nutritional substances which do not benefit from the tracking of dynamic nutritional information such as $\Delta N$, which are not information enabled and are referred to herein as dumb nutritional substances. Information-enabled nutritional substances would be available in virtual internet marketplaces, as well as traditional marketplaces. Because of information provided by information-enabled nutritional substances, entities within the nutritional substance supply system 10, including consumers, would be able to review and select information-enabled nutritional substances for purchase. It should be expected that, initially, the information-enabled nutritional substances would enjoy a higher market value and price than dumb nutritional substances. However, as information-enabled nutritional substances become more the norm, the cost savings from less waste due to degradation of information-enabled nutritional substances could lead to their price actually becoming less than dumb nutritional substances.

For example, the producer of a ready-to-eat dinner would prefer to use corn of a high nutritional, organoleptic, and/or aesthetic value in the production of its product, the ready-to-eat dinner, so as to produce a premium product of high nutritional, organoleptic, and/or aesthetic value. Depending upon the levels of the nutritional, organoleptic, and/or aesthetic values, the ready-to-eat dinner producer may be able to charge a premium price and/or differentiate its product from that of other producers. When selecting the corn to be used in the ready-to-eat dinner, the producer will seek corn of high nutritional, organoleptic, and/or aesthetic value from preservation module 300 that meets its requirements for nutritional, organoleptic, and/or aesthetic value. The packager/shipper of preservation module 300 would also be able to charge a premium for corn which has high nutritional, organoleptic, and/or aesthetic values. And finally, the packager/shipper of preservation module 300 will select corn of high nutritional, organoleptic, and/or aesthetic value from the grower of creation module 200, who will also be able to charge a premium for corn of high nutritional, organoleptic, and/or aesthetic values.

Further, the consumer of the ready-to-eat dinner may want to, or in the case of a restaurant, cafeteria, or other regulated eating establishment, may be required to, track the nutritional, organoleptic, and/or aesthetic value of the corn during the local storage of the ready-to-eat dinner. The local storage environments, local storage containers, and local storage coupons of the present invention enable such tracking by making information related to ΔN during local storage available to information module 100 for updating the dynamic nutritional, organoleptic, and aesthetic values of a nutritional substance.

The change to nutritional, organoleptic, and/or aesthetic value for a nutritional substance, or ΔN, tracked through nutritional substance supply system 10 through nutritional substance information from information module 100 can be preferably determined from measured information. However, some or all such nutritional substance ΔN information may be derived through measurements of environmental conditions of the nutritional substance as it travelled through nutritional substance supply system 10. Additionally, some or all of the nutritional substance ΔN information can be derived from ΔN data of other nutritional substances which have travelled through nutritional substance supply system 10. Nutritional substance ΔN information can also be derived from laboratory experiments performed on other nutritional substances, which may approximate conditions and/or processes to which the actual nutritional substance has been exposed. This information may be utilized to estimate ΔN for a present nutritional substance 520 prior to conditioning by determine the average ΔN for the nutritional substance 520 for a given conditioning protocol or for the passage of a certain amount of time. In some embodiments, this may include determining an average ΔN per unit weight of the nutritional substance 520. Then, when a consumer 540 or other end user selects a nutritional substance 520 for conditioning, the weight of the nutritional substance 520 may be detected or provided by a dynamic nutritional identifier, and the ΔN per unit weight may be multiplied by the sensed or provided weight of the nutritional substance 520. That way a total ΔN may be output that is assumed to result to the present nutritional substance 520 based on selected conditioning protocol. In other embodiments, the nutritional substance 520 testing will be with a pre-packaged food that is the same weight or mass in every package and so the ΔN will not vary by weight. In still other embodiments, the ΔN may be determined for a range of conditioning protocols, but not every possible conditioning (or transformation) protocol for a given nutritional substance 520. Accordingly, if the end user is able to select a range of preferences, the system may have to extrapolate between two or more prior data points to determine an estimated ΔN for the specific conditioning protocol selected for the nutritional substance 520. For example, if a consumer decides to cook 16 ounces of salmon, and decides to have it medium well, the oven may be set at 12 minutes at 350 degrees. However, the system may only have experimental delta N for 12 ounces of salmon at 310 degrees and 18 ounces of salmon at 360 degrees. Accordingly, the system may either provide a curve or correlation line between tested data points and associated ΔN s to determine the present ΔN for the specific conditioning or transformation protocol selected for the piece of salmon. In other embodiments, other suitable methods may be utilized using experimental data to estimate ΔN.

In some embodiments, in order for the system to determine an estimated ΔN, the system may have access to data relating to the percentage reduction in certain vitamins, water, fat content or other ΔN values for given conditioning protocols 610. Those ΔN values may then be applied to a specific nutritional substance 520 as an estimate for the ΔN. For example, if the percentage reduction for a given nutritional substance 520 is known, then the ΔN values that could be calculated for a given protocol could be recorded as percentages. If a specific nutritional substance 520 includes a dynamic information identifier that includes the weight of the nutritional substance 520, the percentages can be multiplied by an average starting nutritional content for a specific nutrient or the amount of that nutrient indicated by a dynamic information identifier to determine the amount of a specific nutrient after conditioning and the loss of that nutrient.

The prior ΔN values may be determined in a variety of ways including: experimentation with specific conditioning protocols 610 on nutritional substances 520. This would allow one to provide more accurate and specific measures of ΔN values for specific conditioning protocols 610. Additionally, if data for ΔN is recorded for variations of the conditioning protocol 610 then the system may be able to more easily extrapolate ΔN values to determine a modified ΔN value for a conditioning protocol 610 with only slight modifications (i.e. certain times extended or cycles removed or added) as described above.

Figure 15:
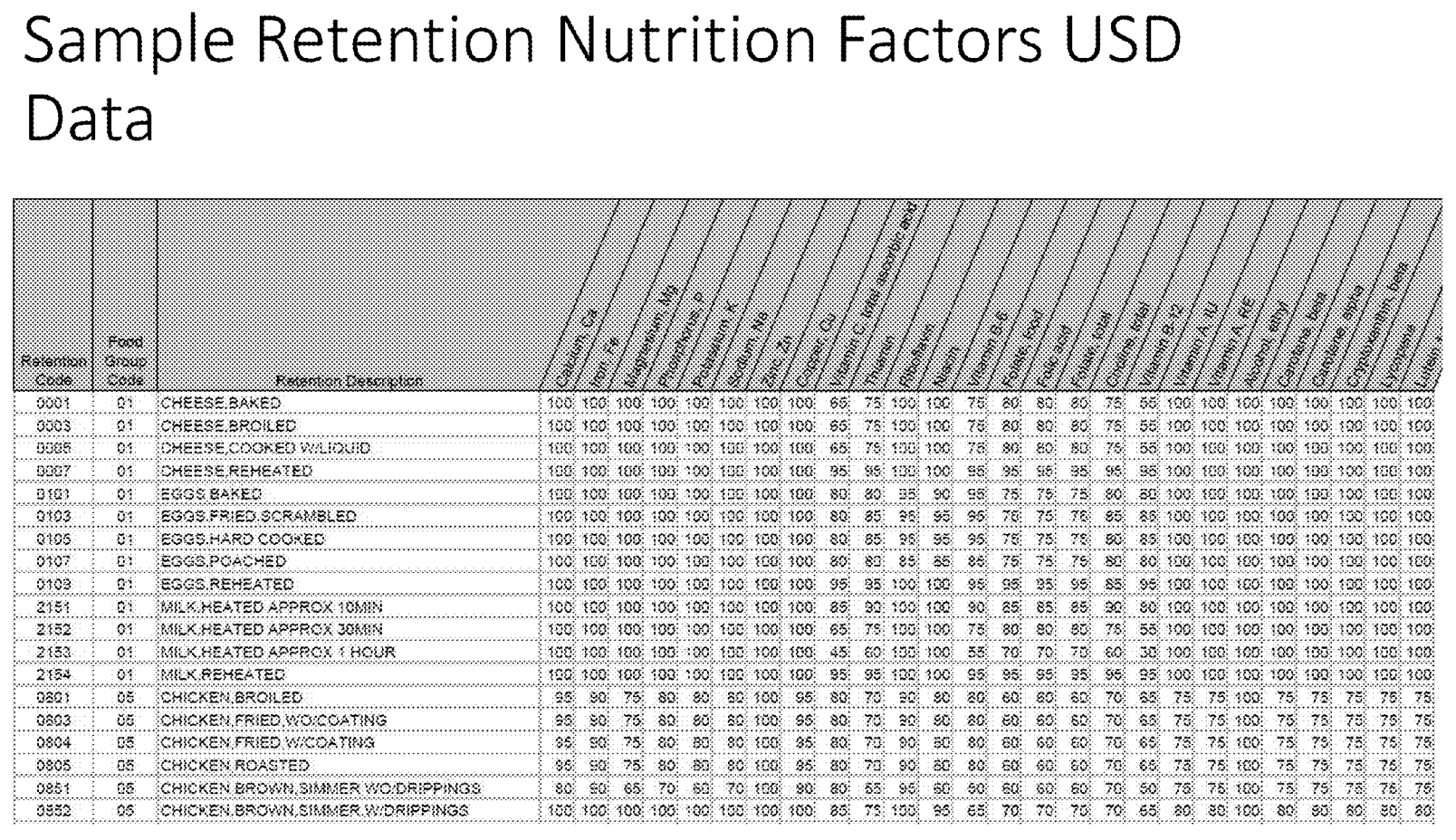

In other embodiments, prior ΔN values for similar nutritional substances 520 may be derived from the USDA's website, where tables of changes in nutritional content are presented. The USDA's values for changes in nutritional content are generally based on one recipe for each type of conditioning. For example, an example table from the USDA website is shown in FIG. 15. Specifically, FIG. 15 illustrates values of nutrients retained after cooking various nutritional substances 520 using a generalized conditioning protocol 610 (e.g., bake, broil, reheated, etc.). For example, nutritional retention values for cheese are displayed based on baking, broiling, cooking with liquid and reheating cheese. Across the columns, various nutrients are listed and the table displays the percentage retention of each nutrient based on, for example, a generic "BAKED" protocol 610.

Figure 16:
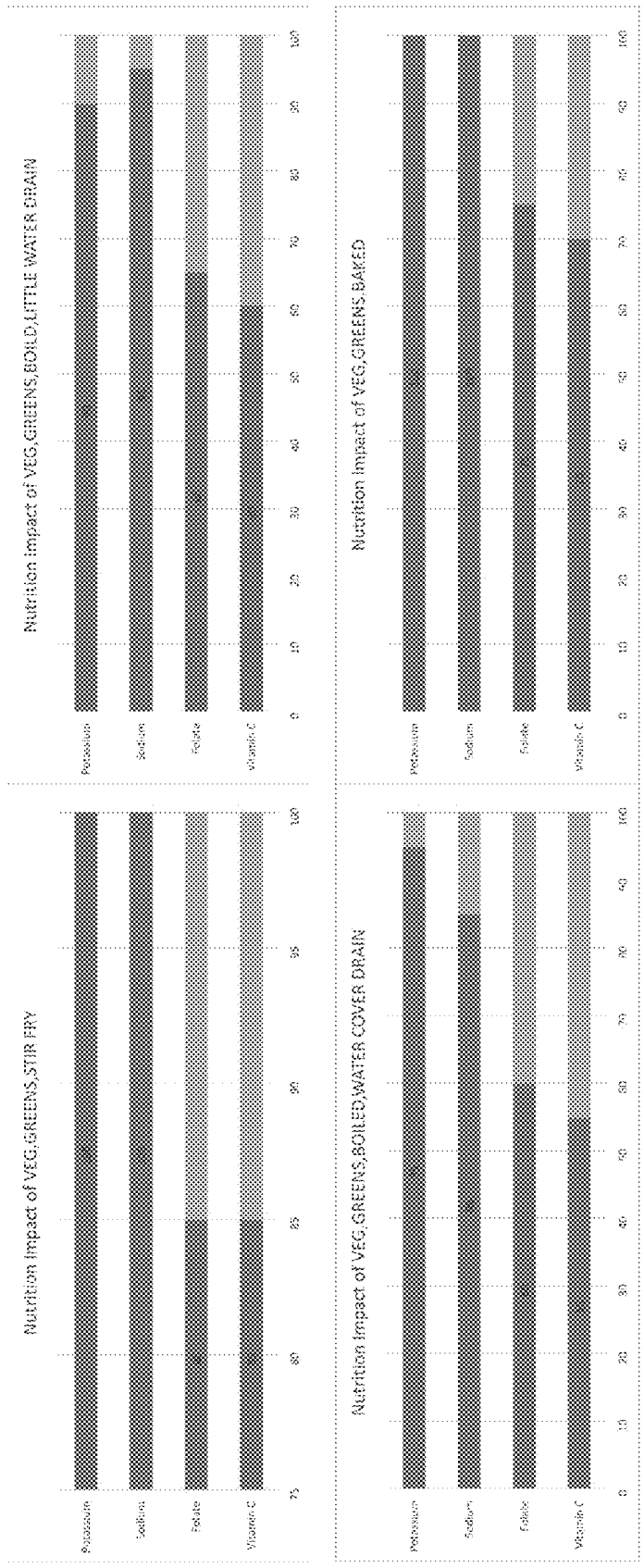
FIG. 16 shows bar graphs representing the nutritional retention values for various conditioning methods for vegetable stir fry based on data from the USDA.
Figure 17:
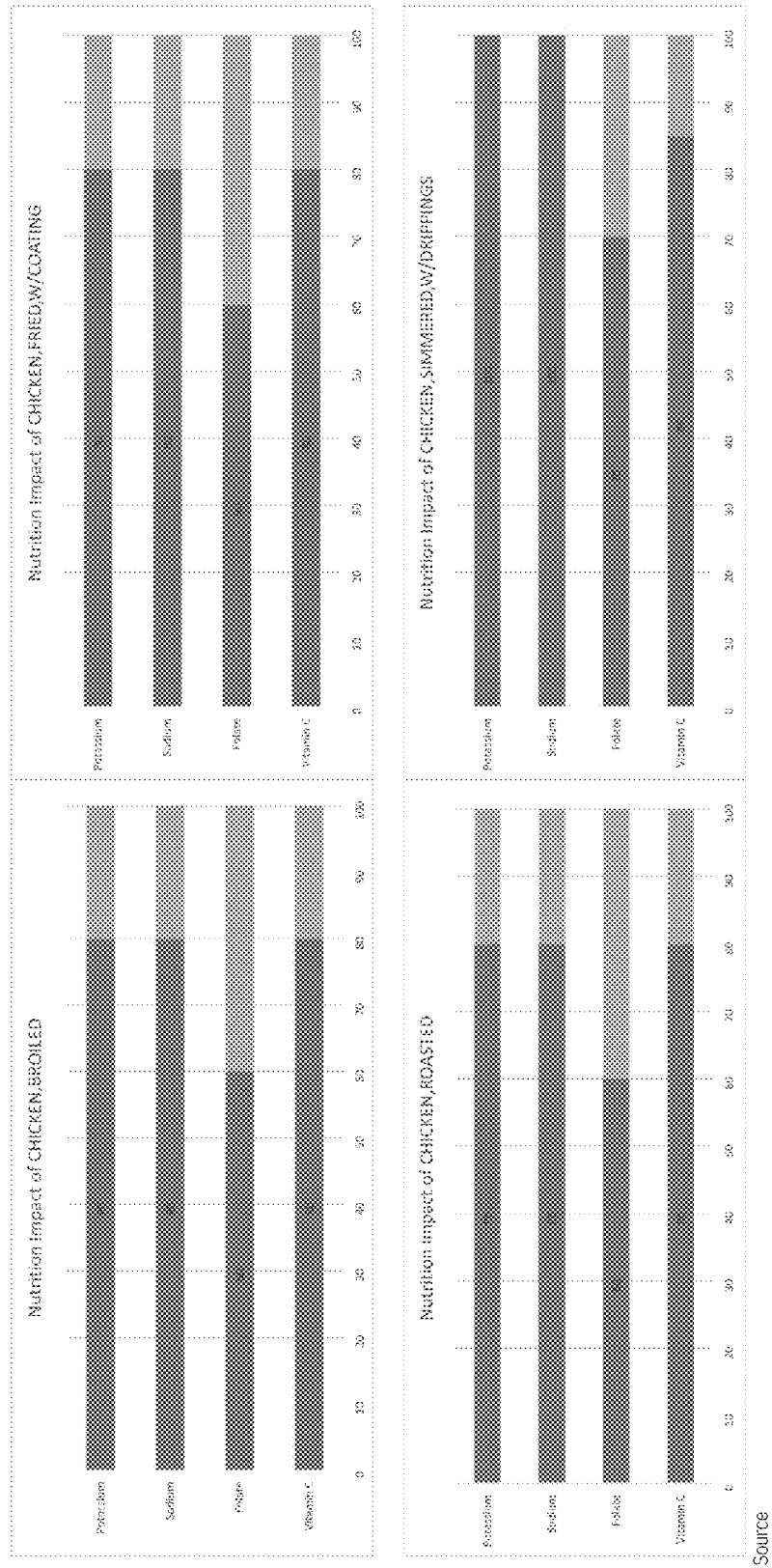
FIG. 17 shows bar graphs representing the nutritional retention values for various conditioning methods for chicken based on data from the USDA.

As further examples, FIGS. 16-17 illustrate bar graphs indicating the nutritional retention using various different conditioning protocols 610 for vegetable stir fry (FIG. 16) and chicken (FIG. 17). As can be seen from the figures, the retention profile for different types of cooking can vary widely between conditioning methods, and therefore displaying or allowing consumers choices in how to condition their food may be beneficial. For example, the vitamin C retention after cooking greens will vary from 56% if they are boiled, to 85% if they are stir fried. Accordingly, in that case, a consumer may be able to balance the cooking method they prefer for taste between the two, and whether vitamin retention is more important with respect to specific nutrients.

The USDA's generic protocols 610 are defined by the USDA and used to perform experiments to derive the values they publish for nutrient retention. The USDA accordingly utilizes a basic protocol for each of the baking, broiling, and other conditioning types mentioned, and tests various examples of the broad nutritional substance 520 category, (e.g. cheese) in order to determine an average for retention of certain nutrients. To calculate these data points, the USDA utilized equation (1) to calculate the percent retention:

$$\% \ TR = (N_c * G_c)/(N_r * G_r) * 100 \qquad (1)$$

where TR=true retention, $N_c$=nutrient content per gram of cooked food, $G_c$=grams of cooked food, $N_r$=nutrient content per g of raw food, and $G_r$=grams of food before cooking. This equation is then utilized by the USDA as detailed on its website, for example at http://www.ars.usda.gov/SP2UserFiles/Place/12354500/Data/SR26/sr26_doc.pdf as part of the National Nutrient Database for Standard Reference. Accordingly, these data points can be used as rough estimates for the ΔN experienced by specific nutritional substances 520 and specific conditioning protocols 610. In this embodiment, each specific conditioning protocol 610 that is stored in the database of the system would have to be linked or referenced to one of the basic conditioning protocols 610 for which the USDA has data. Accordingly, a prospective conditioning protocol 610 would be assumed to result in a ΔN associated with the general recipe it is linked to.

In further embodiments, to true retention, the percentage of weight retained after conditioning may also be calculated as yield percentage based on the following equation 2 from the USDA:

$$\text{Yield (\%)}=100\times(W_{ch}/W_{cr}) \qquad (2)$$

Where yield is the percentage of weight retained after conditioning, $W_{ch}$ is the weight of the cooked sample while hot, and $W_{cr}$ is the weight of the raw sample to be cooked. Accordingly, this is one example of the change in weight can be estimated for a specific nutritional substance 520 based on an average for that nutritional substance 520 by multiplying the average percent yield by the weight of the specific nutritional substance 520. For example, if a nutritional substance 520 is provided with a dynamic nutrition identifier that includes the weight of the substance 520, the weight of the substance may be multiplied by the percent yield calculated for a specific conditioning protocol 610 to determine an estimate for the reduction in weight that the nutritional substance 520 will experience after cooking. Accordingly, this value may be utilized in conjunction with the moisture/fat change values of equation 3 from the USDA to determine overall reduction in nutritional and other ΔN values:

$$\text{Moisture/Fat Change (\%)}=100\times((N_c{}^*E_c)-(N_r{}^*E_r))/W_{cr} \qquad (3)$$

where $N_c$ is the nutrient content of the cooked sample (lean or edible portion) (i.e. fat or moisture), $N_r$ is the nutrient content of the raw sample (lean or edible portion) (i.e. fat or moisture), $E_c$ is the edible portion of the cooked sample, $E_r$ is the edible portion of the raw sample, $W_{cr}$ is the weight of the cooked sample while hot, and $W_{cr}$ is the weight of the raw sample to be cooked. Accordingly, the moisture/fat change % can be determined through experimentation and can be used to determine an estimated moisture and/or fat reduction for a particular nutritional substance 520 based on a particular conditioning protocol 610. These equations are disclosed by the USDA and utilized to determine their experimental based averages for changes in nutritional values. Similar equations may be utilized to determine precise changes for specific nutritional substances (e.g. 3 year aged cheddar v. cheese) based specific conditioning protocols (bake for 3 minutes then steam v. bake). Sample data in connection with cooking yields is shown in FIG. 18.

Once these values are determined, these values could be displayed alongside choices for conditioning to allow a consumer to determine the optimal conditioning protocol based on their nutritional and taste preferences. As in the case with the USDA data, this specific experimental data may be referenced to the conditioning protocols in a database or using another system in order for the ΔN values to be properly accessed or associated with specific conditioning protocols 610 available to a user on a specific conditioner. In some embodiments, as disclosed herein, these estimated ΔN values may be utilized to derive conditioning protocols 610 to match to maximize or find local maximums for ΔN values based on indicated preferences for maximizing certain nutrients or taste preferences.

For example, laboratory experiments can be performed on bananas to determine effect on or change in nutritional, organoleptic, and/or aesthetic value, or ΔN, for a variety of environmental conditions bananas may be exposed to during packaging and shipment in preservation module 300. Using this experimental data, tables and/or algorithms could be developed which would predict the level of change of nutritional, organoleptic, and/or aesthetic values, or ΔN, for a particular banana based upon information collected regarding the environmental conditions to which the banana was exposed during its time in preservation module 300. While the ultimate goal for nutritional substance supply system 10 would be the actual measurement of nutritional, organoleptic, and/or aesthetic values to determine ΔN, use of derived nutritional, organoleptic, and/or aesthetic values from experimental data to determine ΔN would allow improved logistics planning because it provides the ability to prospectively estimate changes to nutritional, organoleptic, and/or aesthetic values, or ΔN, and because it allows more accurate tracking of changes to nutritional, organoleptic, and/or aesthetic values, or ΔN, while technology and systems are put in place to allow actual measurement.

Figure 3:
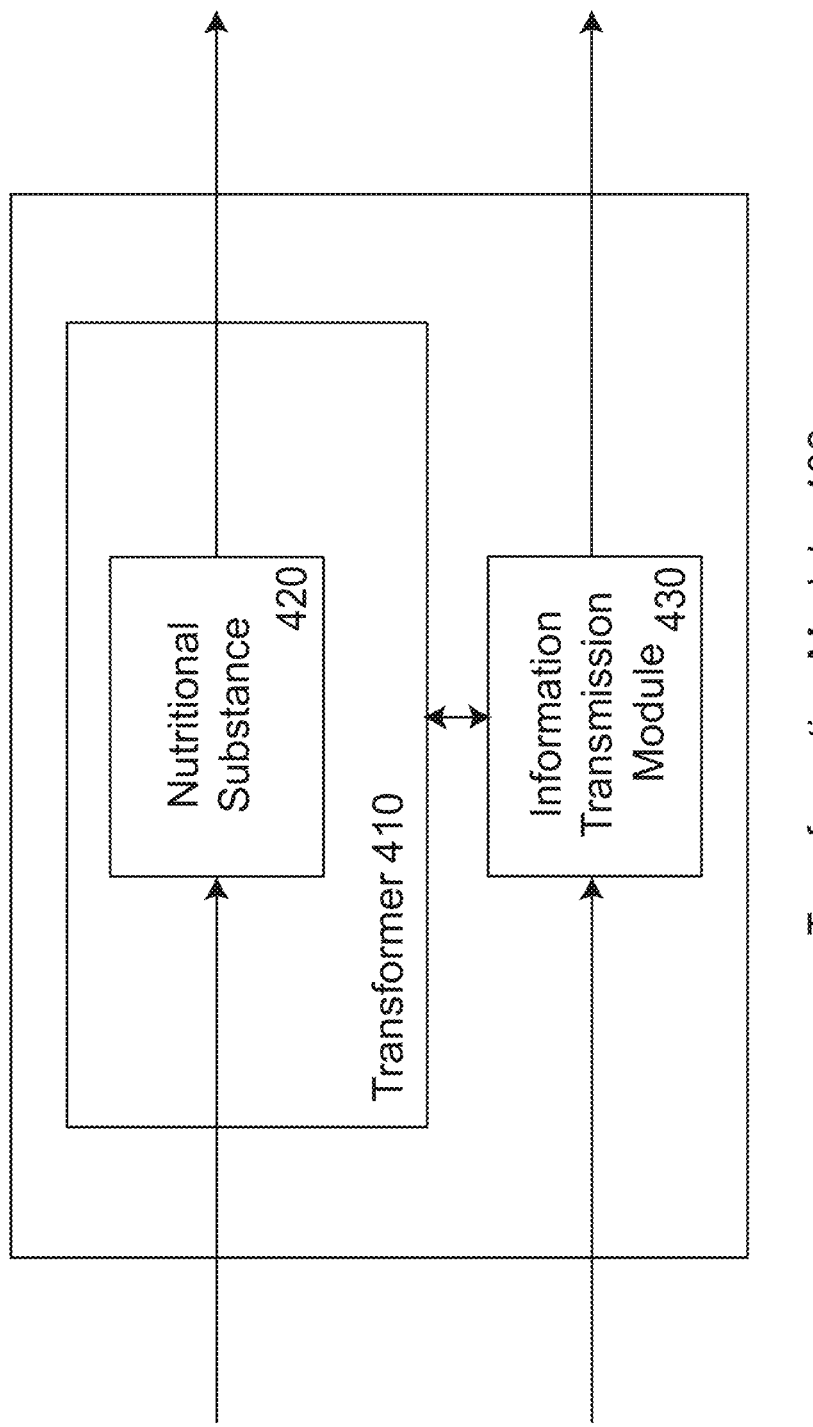
FIG. 3 shows a schematic functional block diagram of a transformation module according to the present invention.

FIG. 3 shows an embodiment of transformation module 400 of the present invention. Transformation module 400 includes transformer 410, which acts upon nutritional substance 420, and information transmission module 430. When transformer 410 receives a nutritional substance 420, information transmission module 430 also receives, or retrieves information about the particular nutritional substance 420 that is to be transformed. This information can include creation information, preservation information, packaging information, shipping information, and possibly previous transformation information. After nutritional substance 420 has been transformed by transformer 410, such information is passed along with the transformed nutritional substance 420 by the information transmission module 430.

For example, sweet corn that arrives for processing by transformer 410 has information associated with it, including the corn variety, where it was planted, when it was planted, when it was picked, the soil it was grown in, the water used for irrigation, and the fertilizers and pesticides that were used during its growth. There may also be information on nutritional and/or organoleptic and/or aesthetic values of the corn when it was preserved for shipment. This information may be stored in the labeling of the corn. However, it may be stored in a database maintained by the grower, shipper, or the nutritional substances industry, also referred to herein as a dynamic nutritional value database. Such information could be accessed by means of telecommunications systems, such as wireless telecommunication systems.

Additionally, the corn may have information associated with it regarding how it was preserved for shipment from the farm to transformation module 400. Such information may include historical information on the environment exterior the container it was shipped in, internal conditions of the container and actual information about the corn during the shipment. Additionally, if the preservation system acted upon such information in preserving the corn, information about the preservation measures may also be available. Such information may be stored in the preservation system. However, it may be stored in a database maintained by the grower, shipper, or the nutritional substances industry, also referred to herein as a dynamic nutritional value database. Such information could be accessed by means of telecommunications systems, such as wireless telecommunication systems.

In the example where the nutritional substance 420 is corn, transformer 410 removes the husk and the silk from the corn. It then separates the kernels from the cob, washes the kernels, and cooks them. Finally, transformer 410 packages the cooked corn in a can and labels the can. The label on the can may contain all the information provided to information transmission module 430. Preferably, this information is referenced by a dynamic encode or tag, herein referred to as a dynamic information identifier, which identifies the information regarding the corn in the can that is being transmitted by information transmission module 430.

In practice, information transmission module 430 would receive the information regarding the nutritional substance 420 from a database that is being used to track the corn during its journey from the farm to the consumer. When transformer 410 transforms nutritional substance 420, information transmission module 430 retrieves the appropriate information from the database and transmits it to another database. Alternatively, the information retrieved by transmission module 430 would be transmitted back to the original database, noting that the transformation had occurred. Preferably, the information regarding the corn retrieved by transmission module 430 would simply be appended with the information that the transformation had occurred. Such databases are individually and collectively referred to herein as a dynamic nutritional value database.

If the nutritional substance 420 can no longer be tracked by the reference information or dynamic information identifier that accompanied the nutritional substance from the creator, then new reference information or a new dynamic information identifier may be created. For example, if the corn is combined with lima beans in the transformer 410, to make succotash, then the information for each may be combined and assigned a new reference number or a new dynamic information identifier. Preferably, a new entry is created in the dynamic nutritional value database, with references to the information related to the corn and the information related to the lima beans.

Figure 4:
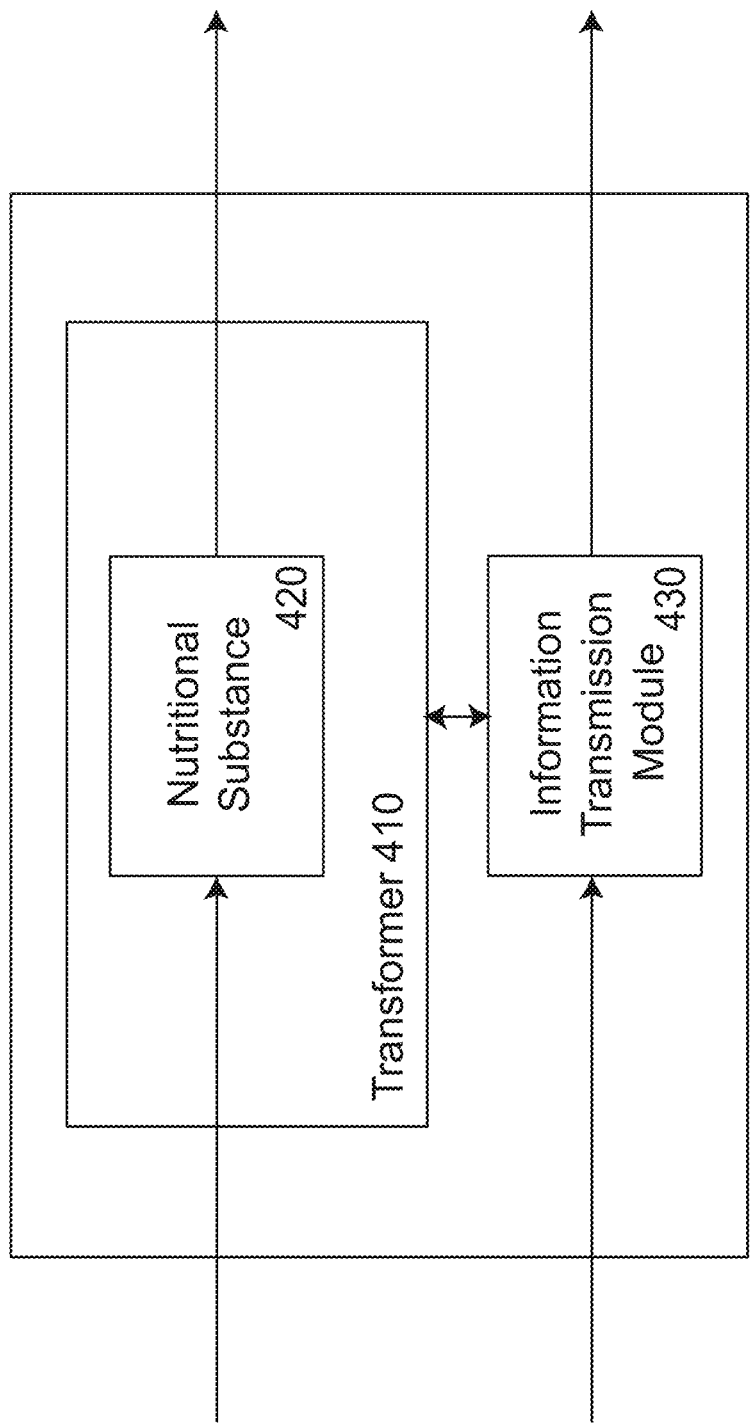
FIG. 4 shows a schematic functional block diagram of a transformation module according to the present invention.

FIG. 4 shows an embodiment of transformation module 400 of the present invention. Transformation module 400 includes transformer 410, which acts upon nutritional substance 420, and information transmission module 430. When transformer 410 receives a nutritional substance 420, information transmission module 430 also receives, or retrieves information about the particular nutritional substance 420 that is to be transformed. This information can include creation information, packaging information, shipping information, and possibly previous transformation information. After nutritional substance 420 has been transformed by transformer 410, such information is passed along with the transformed nutritional substance 420 by the information transmission module 430, along with specific information relating to the transformation done by transformer 410.

For example, sweet corn that arrives for processing by transformer 410 has information associated with it, including the corn variety, where it was planted, when it was planted, when it was picked, the soil it was grown in, the water used for irrigation, and the fertilizers and pesticides that were used during its growth. There may also be information on nutritional, organoleptic and aesthetic values of the corn when it was preserved for shipment. This information may be stored in the labeling of the corn. However, it may be stored in a dynamic nutritional value database maintained by the grower, shipper, or the nutritional substances industry. Such information could be accessed by telecommunications systems, such as wireless telecommunication systems.

Additionally, the corn may have information associated with it regarding how it was preserved for shipment from the farm to transformation module 400. Such information may include historical information on the environment exterior the container it was shipped in, internal conditions of the container and actual information about the corn during the shipment. Additionally, if the preservation system acted upon such information in preserving the corn, information about the preservation measures may also be available. Such information may be stored in the preservation system. However, it may be stored in a dynamic nutritional value database maintained by the grower, shipper, or the nutritional substances industry. Such information could be accessed by means of telecommunications systems, such as wireless telecommunication systems.

In the example where the nutritional substance 420 is corn, transformer 410 removes the husk and the silk from the corn. It then separates the kernels from the cob, washes the kernels, and cooks them. Finally, transformer 410 packages the cooked corn in a can and labels the can.

During this transformation of the nutritional substance 420 by transformer 410, information about the transformation can be captured by transformer 410 and sent to information transmission module 430. This information can include how the transformation was accomplished; including information on the transformer used, the recipe implemented by transformer 410, and the settings for transformer 410 when the transformation occurred. Additionally, any information created during the transformation by transformer 410 can be sent to the information transmission module 430. This could include measured information, such as the actual cooking temperature, length of time of each of the steps, or weight or volume measurements. Additionally, this information could include measured aesthetic, organoleptic and nutritional values.

The label on the can may contain all the information provided to information transmission module 430. Preferably, this information is referenced by a dynamic information identifier which identifies the information regarding the corn in the can that is being transmitted by information transmission module 430.

In practice, information transmission module 430 would receive the information regarding the nutritional substance 420 from a database that is being used to track the corn during its journey from the farm to the consumer. When transformer 410 transforms nutritional substance 420, information transmission module 430 retrieves the appropriate information from the database, appends it with the information from transformer 410 regarding the transformation, and transmits it to another database. Alternatively, such information would be transmitted back to the original database, including the transformation information. Preferably, the information regarding the corn would simply be appended with the information from transformer 410 about the transformation. Such databases are individually and collectively referred to herein as a dynamic nutritional value database If the nutritional substance 420 can no longer be tracked by the reference information or a dynamic information identifier that accompanied the nutritional substance from the creator, then new reference information or a new dynamic information identifier may be created. For example, if the corn is combined with lima beans in the transformer 410, to make succotash, then the information for each may be combined and assigned a new reference number or a new dynamic information identifier. Preferably, a new entry is created in the dynamic nutritional value database, with references to the information related to the corn and the information related to the lima beans.

Figure 5:
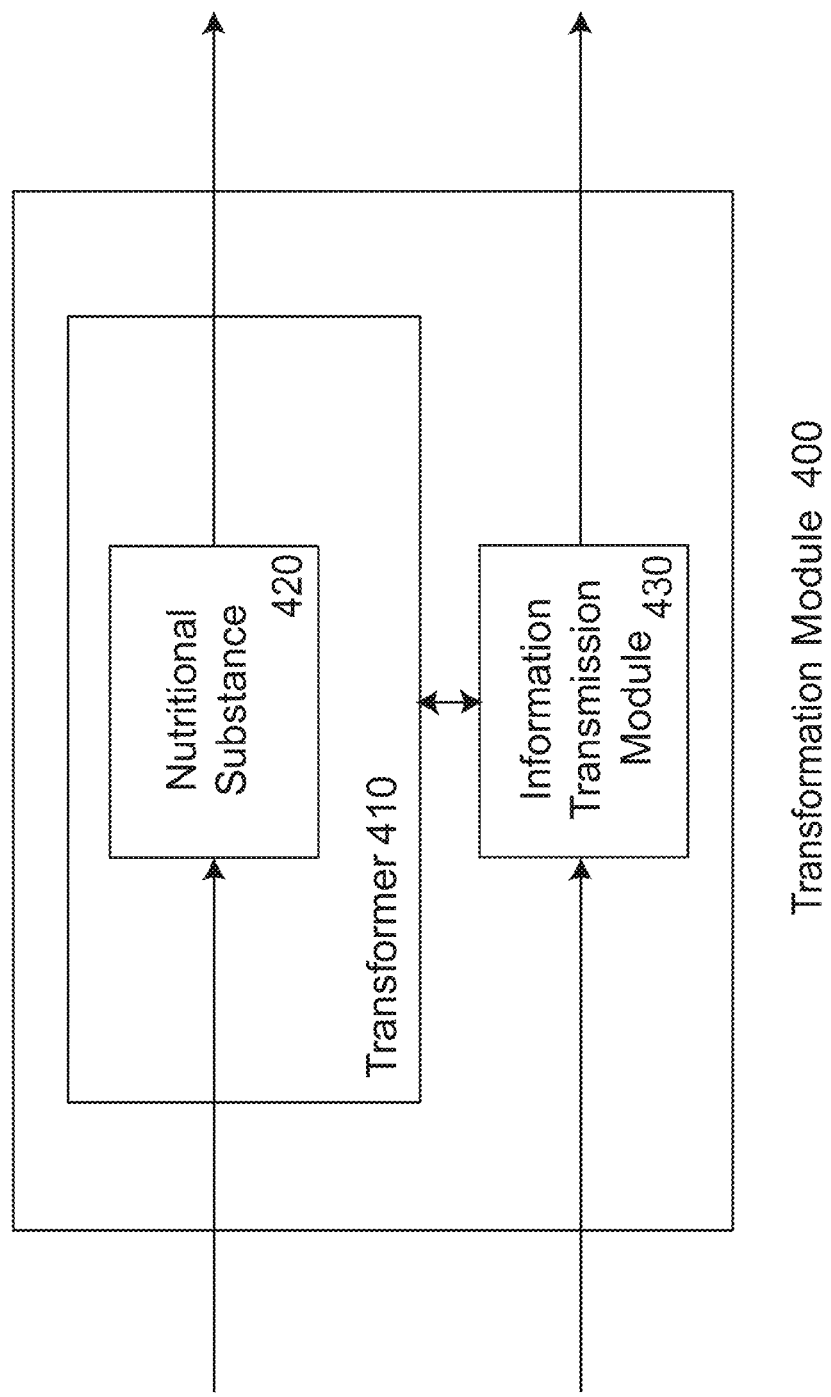
FIG. 5 shows a schematic functional block diagram of a transformation module according to the present invention.

FIG. 5 shows an embodiment of transformation module 400 of the present invention. Transformation module 400 includes transformer 410, which acts upon nutritional substance 420, and information transmission module 430. When transformer 410 receives a nutritional substance 420, information transmission module 430 also receives, or retrieves information about the particular nutritional substance 420 that is to be transformed. This information can include creation information, packaging information, shipping information, and possibly previous transformation information. This information is used by transformer 410 to dynamically modify the transformation, the process referred to herein as adaptive transformation. After nutritional substance 420 has been transformed by transformer 410, such information is passed along with the transformed nutritional substance 420 by the information transmission module 430, along with specific information relating to the adaptive transformation done by transformer 410.

For example, sweet corn that arrives for processing by transformer 410 has origination information associated with it, including the corn variety, where it was planted, when it was planted, when it was picked, the soil it was grown in, the water used for irrigation, and the fertilizers and pesticides that were used during its growth. There may also be source information on nutritional, organoleptic and aesthetic values of the corn when it was preserved for shipment. This information may be stored in the labeling of the corn. However, it may be stored in a dynamic nutritional value database maintained by the grower, shipper, or the nutritional substances industry. Such information could be accessed by telecommunications systems, such as wireless telecommunication systems.

Additionally, the corn may have information associated with it regarding how it was preserved for shipment from the farm to transformation module 400. Such information may include historical information on the environment exterior the container it was shipped in, internal conditions of the container and actual information about the corn during the shipment. Additionally, if the preservation system acted upon such information in preserving the corn, information about the preservation measures may also be available. Such information may be stored in the preservation system. However, it may be stored in a database maintained by the grower, shipper, or the nutritional substances industry, also referred to herein as a dynamic nutritional value database. Such information could be accessed by means of telecommunications systems, such as wireless telecommunication systems.

Any, or all, of this information can be provided to transformer 410 by information transmission module 430. Transformer 410 can dynamically modify its transformation of nutritional substance 420 in response to such information to adaptively transform the nutritional substance in order to preserver or improve or minimize the degradation of the nutritional, organoleptic and/or aesthetic values of nutritional substance 420.

In the example where the nutritional substance 420 is corn, transformer 410 removes the husk and the silk from the corn. It then separates the kernels from the cob, washes the kernels, and cooks them. In response to the information provided by information transmission module 430, transformer can dynamically modify the cooking temperature and time. For example, if transformer 410 receives information that indicates that the corn is low in certain desirable nutrients, it might lower the cooking temperature and time to preserve those nutrients, thus achieving a more desirable nutritional value related to those specific nutrients in the transformed nutritional substance. However, if transformer 410 receives information that indicates that the corn is high in tough starches, it might raise the cooking temperature and time to soften the corn, thus achieving a more desirable organoleptic value related to the texture of the transformed nutritional substance. Finally, transformer 410 packages the cooked corn in a can and labels the can.

Additionally, transformer 410 can modify its transformation of the nutritional substance in response to measured attributes of the particular nutritional substance 420 being transformed. For example, transformer 410 can measure the color of the corn to be processed, and in response make adjustment to the transformation to preserve or enhance the color of the transformed corn, thus achieving a more desirable aesthetic value related to the appearance of the transformed nutritional substance.

During this adaptive transformation of the nutritional substance 420 by transformer 410, information about the transformation can be captured by transformer 410 and sent to information transmission module 430. This information can include how the transformation was accomplished; including information on any dynamic transformation modifications in response to information about the particular nutritional substance to be transformed, the recipe implemented by transformer 410, and the settings for transformer 410 when the transformation occurred. Additionally, any information created during the transformation by transformer 410 can be sent to the information transmission module 430. This could include measured information, such as the actual cooking temperature, length of time of each of the steps. Additionally, this information could include measured organoleptic, aesthetic, and nutritional information, weight, and physical dimension.

The label on the packaging may contain all the information provided to information transmission module 430. Preferably, this information is referenced by a dynamic information identifier which identifies the information regarding the nutritional substance in the packaging that is being transmitted by information transmission module 430.

In practice, information transmission module 430 would utilize a dynamic information identifier provided with the nutritional substance to retrieve and receive the information regarding the nutritional substance 420 from a database that is being used to track the corn during its journey from the farm to the consumer. When transformer 410 transforms nutritional substance 420, information transmission module 430 retrieves the appropriate information from the database, appends it with the information from transformer 410 regarding the transformation, and transmits it to another database. Alternatively, such information would be transmitted back to the original database, including the transformation information. Preferably, the information regarding the corn would simply be appended with the information from transformer 410 about the transformation. Such databases are individually and collectively referred to herein as a dynamic nutritional value database.

If the nutritional substance 420 can no longer be tracked by the reference information or dynamic information identifier that accompanied the nutritional substance from the creator, then new reference information or a new dynamic information identifier may be created. For example, if the corn is combined with lima beans in the transformer 410, to make succotash, then the information for each may be combined and assigned a new reference number or a new dynamic information identifier. Preferably, a new entry is created in the dynamic nutritional value database, with references to the information related to the corn and the information related to the lima beans.

Figure 6:
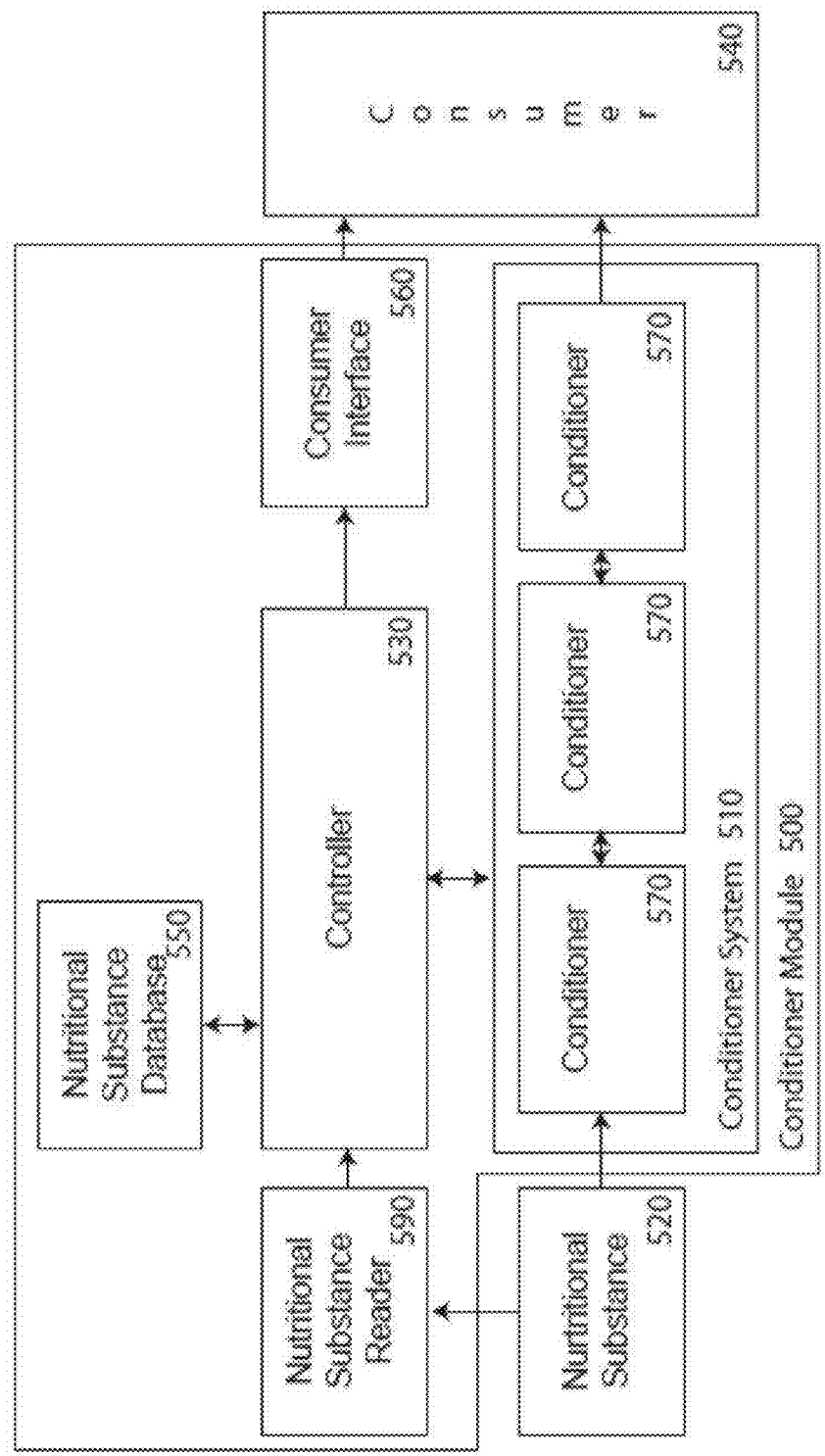
FIG. 6 shows a schematic functional block diagram of a conditioning module according to the present invention.

FIG. 6 shows an embodiment of conditioner module 500 of the present invention. Conditioner system 510 receives nutritional substance 520 for conditioning before it is delivered to consumer 540. Controller 530 is operably connected to conditioner system 510. In fact, controller 530 may be integrated within conditioner system 510, or provided as a separate device, shown in FIG. 3. Although FIG. 6 is directed to a conditioner module 500, conditioner system 510, with associated conditioners 570, it is understood that the conditioner module may be replaced by the preservation module 300, conditioner system 570 and conditioners 570 may be replaced by any appliance or local storage container, including a scale as disclosed herein to provide the functionality disclosed herein. This will provide the same features, including the nutritional substance reader 590, the controller 530, nutritional substance database 550, consumer interface 560, consumer 540, but in conjunction with other appliance, including scales, refrigerators, local storage environments, and others.

In an embodiment of the present invention, conditioner 570 is provided without controller 530, however it is provided in a format to be compatible with controller 530. Such a conditioner is also referred to herein as an information capable conditioner. In contrast, traditional conditioners, also referred to herein as dumb conditioners, are not information capable, are not compatible with controller 530, and accordingly will always be dumb conditioners. As information enabled nutritional substances and conditioning systems according to the present invention are increasingly available, dumb conditioners will become increasingly obsolete.

Information capable conditioners may be provided in a variety of configurations known to those skilled in the art, and the examples offered herein are for purposes of illustration and not intended to be limiting in any way. In one example of an information capable conditioner, it is provided with traditional functionality, that is, it will interact with nutritional substances in a traditional fashion, whether the nutritional substance is information enabled or not. However, the information capable conditioner is compatible with separately available controller 530, such that at any time during or after the manufacture and sale of the information capable conditioner, controller 530 may be coupled with the information capable conditioner to enable the full functionality and benefit of conditioner module 500. Information capable conditioners provide appliance manufacturers and consumers great flexibility, and will not become obsolete like dumb conditioners. In some embodiments, the information capable conditioner is referred to as a dynamic appliance. In some instances the dynamic appliance has the full functionality and benefit of controller 530 (sometimes referred to as an appliance controller) built into, collocated, or coupled to the dynamic appliance.

The coupling of controller 530 to the information capable conditioner may take any physical and/or communication format known to those skilled in the art. These may include, but are not limited to: an information capable conditioner provided with Bluetooth, or other wireless near-field communication capability, to communicate with a communication-compatible controller 530 which may be any of a completely separate unit, an externally attachable unit, and an internally placed unit; an information capable conditioner provided with a USB port, or other electronic communication capability, to communicate with a communication-compatible controller 530 which may be any of a completely separate unit, an externally attachable unit, and an internally placed unit; an information capable conditioner provided with a fiber optic port, or other optical communication capability, to communicate with a communication-compatible controller 530 which may be any of a completely separate unit, an externally attachable unit, and an internally placed unit; or an information capable conditioner provided with WiFi, or other wireless communication capability, to communicate with a WiFi compatible controller 530 which may be any of a completely separate unit, an externally attachable unit, and an internally placed unit. It is understood that the controller 530 may be provided with its own consumer interface, may communicate and be operated through the consumer interface provided with the information capable conditioner, or a combination of both.

When conditioner system 510 receives nutritional substance 520 for conditioning, nutritional substance reader 590, sometimes referred to as appliance reader in the context of a dynamic appliance, either receives information regarding nutritional substance 520 and provides it to controller 530, which is the case if the nutritional substance 520 contains a label which includes the information about nutritional substance 520, and/or the nutritional substance reader 590 receives reference information allowing retrieval of the information and provides it to controller 530, which is the case if the nutritional substance 520 is associated with, or provided with a dynamic information identifier. In the case where nutritional substance 520 contains a label which includes the desired information about nutritional substance 520, nutritional substance reader 590 reads this information, provides it to controller 530, which makes it available to consumer 540 by means of consumer interface 560.

For example, if nutritional substance 520 is a ready-to-eat frozen dinner which needs to be heated by conditioner system 510, nutritional substance reader 590 would read a label on nutritional substance 520, thereby receiving the information regarding nutritional substance 520, and then provide the information to controller 530. This information could include creation information as to the creation of the various components which constitute the ready-to-eat dinner. This information could include information about where and how the corn in the ready-to-eat dinner was grown, including the corn seed used, where it was planted, how it was planted, how it was irrigated, when it was picked, and information on fertilizers and pesticides used during its growth. Additionally, this information could include the cattle lineage, health, immunization, dietary supplements that were fed to the cattle that were slaughtered to obtain the beef in the ready-to-eat dinner.

The information from a label on nutritional substance 520 could also include information on how the components were preserved for shipment from the farm or slaughterhouse on their path to the nutritional substance transformer who prepared the ready-to-eat dinner. Additional information could include how the nutritional substance transformer transformed the components into the ready-to-eat dinner, such as recipe used, additives to the dinner, and actual measured conditions during the transformation into the ready-to-eat dinner.

While such information could be stored on a label located on the packaging for nutritional substance 520 so as to be read by nutritional substance reader 590, provided to controller 530, and provided to consumer interface 560 for display to consumer 540, preferably, the label on the nutritional substance package includes reference information, such as a dynamic information identifier, which is read by nutritional substance reader 590 and provided to controller 530 that allows controller 530 to retrieve the information about nutritional substance 520 from nutritional substance database 550. Further, linking consumer feedback and updates regarding observed or measured changes in the nutritional, organoleptic, and/or aesthetic values of nutritional substances would provide for virtually real time updates of ΔN information from the actual consumer.

Nutritional substance database 550 could be a database maintained by the transformer of nutritional substance 520 for access by consumers of such nutritional substance 520 to track or estimate changes in the nutritional, organoleptic, and/or aesthetic values of those nutritional substances, as well as any other information about the nutritional substance that can be tracked, including but not limited to the examples previously described. However, preferably, nutritional substance database 550 is a database maintained by the nutritional substance industry for all such information regarding nutritional substances grown, raised, preserved, transformed, conditioned and consumed by consumer 540, in which case it is the database contained within information module 100 and also referred to herein as a dynamic nutritional value database.

It is important to note that while FIGS. 6-9 of various embodiments of the present invention show nutritional substance database 550 as part of the conditioner module 500, they are in no way limited to this interpretation. It is understood that this convention is only one way of illustrating the inventions described herein, and it is further understood that this is in no way limiting to the scope of the present invention. The same is understood for recipe database 555, consumer database 580, and nutritional substance industry database 558.

In an alternate embodiment of the present invention, controller 530, in addition to providing information regarding nutritional substance 520 to consumer 540, also receives information from conditioner system 510 on how nutritional substance 520 was conditioned. Additionally, conditioner system 510 may also measure or sense information about nutritional substance 520 before or during its conditioning by conditioner system 510, and provide such information to controller 530, so that such information could also be provided to consumer 540, via consumer interface 560. Such information may be sensed by attribute sensors providing information related to ΔN of the nutritional substance to be utilized by the controller to confirm that conditioning parameters currently being implemented will achieve desired residual nutritional, organoleptic, or aesthetic values, and if it is determined that they will not, such information may be used to adaptively modify the conditioning parameters in order to achieve desired residual nutritional, organoleptic, or aesthetic values. Further, the controller 530 can receive information from the consumer via consumer interface 560 regarding observed or measured changes in the nutritional, organoleptic, and/or aesthetic values of nutritional substances before or after conditioning, to provide virtually real time updates of ΔN information from the actual consumer, for use by the controller and/or transmission to the nutritional substance database 550.

In a preferred embodiment of the present invention, controller 530 organizes and correlates the information it receives regarding nutritional substance 520 from the various sources of such information, including nutritional substance database 550 and conditioner system 510, and presents such information through consumer interface 560 to consumer 540 in a manner useful to consumer 540. For example, such information may be provided in a manner that assists consumer 540 in understanding how nutritional substance 520 meets consumer's 540 nutritional needs. It could organize information regarding nutritional substance 520 to track consumer's 540 weight loss program. Controller 530 could have access to, or maintain, information regarding consumer 540, so as to track and assist consumer 540 in meeting their specific nutritional needs.

In another embodiment of the present invention conditioner system 510 could be a plurality of conditioner devices or dynamic appliances which can be selectively operated by controller 530 to prepare nutritional substance 520. Conditioner system 510 can be either a single conditioning device, such as a microwave oven, toaster oven, conventional oven, toaster, blender, steamer, stovetop, or human cook. Conditioner system 510 may be a plurality of conditioners 570. In the case where a plurality of conditioners 570 comprise conditioner system 510, nutritional substance 520 may be manually or automatically transferred between conditioners 570 for eventual transfer to consumer 540.

Nutritional substance reader 590 may be an automatic reader such as a barcode reader or RFID sensor which receives information from nutritional substance 520 or a reference code from nutritional substance 520, such as a dynamic information identifier associated with, or provided with the nutritional substance 520, and provides this information to controller 530. Nutritional substance reader 590 might also be a manual entry system where the reference code, such as a dynamic information identifier associated with, or provided with the nutritional substance 520, is manually entered into nutritional substance reader 590 for use by controller 530, or may alternatively be manually entered into consumer interface 560 for use by controller 530.

In other embodiments, the consumer may enter information regarding the nutritional substance 520, including information identifying the nutritional substance 520. This may be manually through a user interface on the conditioner or other appliance, a mobile phone wirelessly linked to the appliance or other methods as disclosed herein. This allows the controller 530 to identify and access a database 550 with information regarding types or categories of nutritional substances 520. That way, if the nutritional substance 520 is not provided with an identifier, the consumer can provide the necessary information to sufficiently identify the nutritional substance 520. Accordingly, various sensors may then sense various attributes of a the nutritional substance 520 to complement the information entered manually by the consumer, to provide further specific information on the nutritional substance 520 that may be used to optimize ΔN information provided to the user, optimize conditioning sequences or protocols performed on the nutritional substance 520 or optimize the conditioning protocols or recipes retrieved as options for performance on the nutritional substance 520. For example, the consumer may enter in a category such as salmon. Then, a weight sensor in connection with a conditioner could sense the mass or amount of salmon, and optionally, color or visual sensors could detect whether the salmon is wild salmon (reddish) or farm raised (light pink). In addition, various sensor arrays may be able to detect VOCs or volatile organic compounds that could determine the level of spoliation, or how fresh the fish is. This information taken from sensors could be utilized to derive or to tailor a conditioning protocol to the specific nutritional substance 520, including its weight, age, and other characteristics. In other embodiments, this information could be utilized to select an optimal conditioning protocol from a recipe database 555. For example, the cooking time and process may be modified for a salmon slab depending on its weight. Additionally, certain types of salmon may have more or less fat and therefore, optimal cooking times and temperatures will vary accordingly. If the information database contains data on different weights and types of salmon, and the sensors can detect this information, the conditioning sequence or protocol can be optimized to account for the sensed attributes.

Nutritional substance database 550 could be a flat database, relational database or, preferably, a multi-dimensional database. Nutritional substance database 550 could be local but, preferably, it would be located remotely, such as on the internet, and accessed via a telecommunication system, such as a wireless telecommunication system. Controller 530 can be implemented using a computing device, such as a microcontroller, micro-processor, personal computer, or tablet computer. Controller 530 could be integrated to include nutritional substance reader 590, consumer interface 560, and/or nutritional substance database 550. Additionally, controller 530 may be integrated in conditioner system 510, including integration into conditioner 570.

In addition, nutritional substance reader 590 may be an optical nutritional substance identifier or sensor that optically determines the identity of the nutritional substance 520, and/or certain physical attributes of the nutritional substance 520 by evaluation of data output by sensors that optically sense the nutritional substance 520. For example, an optical sensor may be utilized that captures light or other radiation reflected or transmitted through the nutritional substance 520. Then, the system could evaluate the optical data output by the sensor to determine certain characteristics of the nutritional substance. For example, the optical data may be utilized to determine the color, intensity, shape, radius of curvature, texture, fiber size, and other attributes. These attributes may then be used to classify the nutritional substance 520, for example by identifying the nutritional substance as an apple, red delicious, red delicious from Washington, orange, navel orange, tangelo, or blood orange, carrot, steak, or filet mignon. This identification information may then be utilized to access information, including nutritional and ΔN information, regarding the nutritional substance 520 in the nutritional substance database 550 as described herein with respect to the nutritional substance reader 590. Thus, the optical sensor or reader may be utilized to identify the nutritional substance 520 in place of utilizing a dynamic information identifier on the nutritional substance 520. Various products are available that are capable of using optical technology to visually identify produce, and various other items. For example, an automated optical fruit recognition system developed by Fraunhofer is capable of detecting and identifying various produce optically as described by an article titled "Automated Fruit Recognition" available at http://www.isob.fraunhofer.de/servlet/is/33328/which is incorporated by reference herein in its entirety. Additionally, an optical object recognition system is disclosed in U.S. Pat. No. 6,310,964 that is described as capable of detecting identity and size of produce and is incorporated herein by reference in its entirety.

It is important to note that while FIGS. 6-9 of various embodiments of the present invention show nutritional substance database 550 as part of the conditioner module 500, they are in no way limited to this interpretation. It is understood that this convention is only one way of illustrating the inventions described herein, and it is further understood that this is in no way limiting to the scope of the present invention. The same is understood for recipe database 555, consumer database 580, and nutritional substance industry database 558. For example, any of nutritional substance database 550, recipe database 555, consumer database 580, and nutritional substance industry database 558 can be contained within information module 100 or within conditioner module 500.

Consumer interface 560 can be implemented as a display device mounted on controller 530, conditioner system 510, or conditioner 570. However, consumer interface 560 is preferably a tablet computer, personal computer, personal assistant, or smart phone, running appropriate software, such as an app.

While conditioner module 500 can be located in the consumer's home, conditioner module 500 may be located at a restaurant or other food service establishment for use in preparing nutritional substances 520 for consumers who patronize such an establishment. Additionally, conditioner module 500 could be located at a nutritional substance seller such as a grocery store or health food store for preparation of nutritional substances 520 purchased by consumers at such an establishment. It could be foreseen that conditioner modules 500 could become standalone businesses where consumers select nutritional substances for preparation at the establishment or removal from the establishment for consumption elsewhere.

Figure 7:
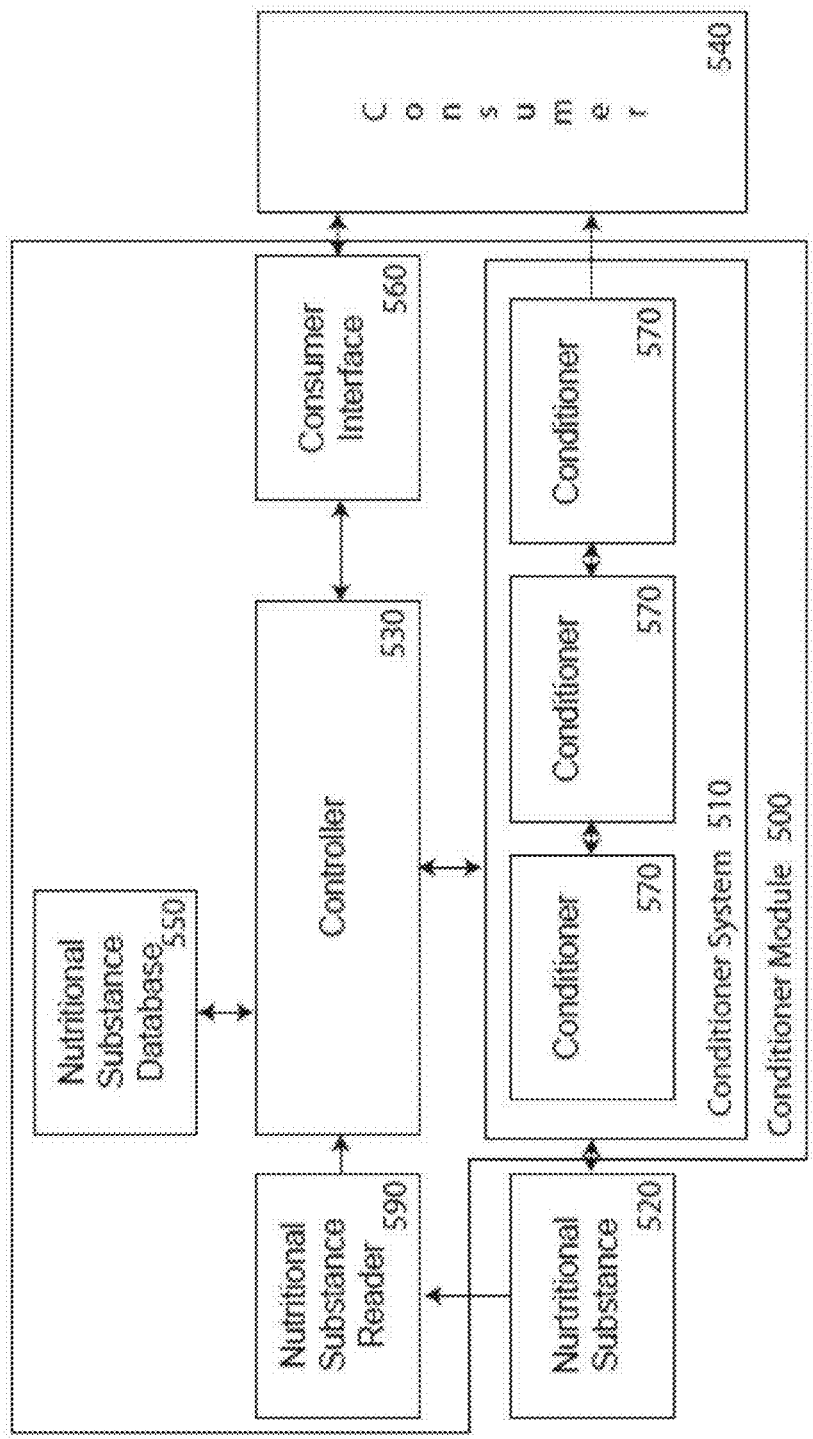
FIG. 7 shows a schematic functional block diagram of a conditioning module according to the present invention.

FIG. 7 shows an embodiment of conditioning module 500 of the present invention. Conditioner system 510 receives nutritional substance 520 for conditioning before it is delivered to consumer 540. Controller 530 is operably connected to conditioner system 510. In fact, controller 530 may be integrated within conditioner system 510, although in FIG. 7, it is shown as a separate device. When conditioner system 510 receives nutritional substance 520 for conditioning, nutritional substance reader 590 either receives information regarding nutritional substance 520 and provides it to controller 530, which is the case if the nutritional substance 520 contains a label which includes the information about nutritional substance 520, and/or the nutritional substance reader 590 receives reference information, such as a dynamic information identifier, and provides it to controller 530, allowing retrieval of the information about nutritional substance 520 from nutritional substance database 550, which is the case when the nutritional substance is associated with, or provided with, a dynamic information identifier. In the case where nutritional substance 520 contains a label which includes information about nutritional substance 520, nutritional substance reader 590 reads this information, provides it to controller 530 and makes it available to consumer 540 by means of consumer interface 560.

In another embodiment, conditioner may also detect certain attributes of nutritional substance 520, through nutritional substance attribute sensors 591. Nutritional substance attribute sensors 591 may be a variety of sensors as disclosed herein, including: (1) weight, (2) a visible light camera, (3) and infrared camera, (3) ambient moisture, (4) ambient temperature, (5) a wireless probe or (6) a spectrometer sensor. The information from the sensors may be provided to controller 530 in addition to or instead of the information provided by nutritional substance reader 590. For example, in some embodiments, the consumer 540 will input information regarding the nutritional substance 520, which may be for example, an identification of the nutritional substance 520, or the general type of nutritional substance 520. Accordingly, the nutritional substance attribute sensors 591 may detect additional information regarding the nutritional substance 520, that may be transferred to the controller 530, including weight, color, surface temperature, probe temperature, ambient temperature once the substance 520 is deposited in the conditioner 570. Data regarding these attributers output from the sensors 591, may be utilized to provide additional information regarding the nutritional substance 520 to the controller 530.

In an embodiment of the present invention, conditioner system 510 comprises conditioner 570. Conditioner 570 is a conditioning apparatus which can perform a number of operations on nutritional substance 520, separately and/or at the same time. For example, conditioner 570 could be a combination microwave oven, convection oven, grill, and conventional oven. Controller 530 could operate conditioner 570 to execute a sequence of conditioning cycles on nutritional substance 520 to complete its conditioning.

For example, if nutritional substance 520 is a whole frozen turkey to be prepared for dinner, consumer 540 would place the turkey in conditioner 570, the combination cooking unit suggested above. Controller 530 would receive and/or create a protocol of conditioning cycles. Such a protocol could be read by nutritional substance reader 590 from a label on nutritional substance 520. Alternately, a protocol of conditioning cycles could be obtained from nutritional substance database 550 through reference information, such as a dynamic information identifier, obtained by nutritional substance reader 590 from nutritional substance 520. For example, a label on the turkey, could be read by nutritional substance reader 590, providing reference information for the turkey, such as a dynamic information identifier, which controller 530 uses to obtain a conditioning protocol for the turkey from nutritional substance database 550.

Additionally, various conditioning protocols stored in nutritional substance database 550 may contain data or be mapped to information regarding certain attributes that are sensed by nutritional substance attribute sensors 591. In other embodiments, these may be maintained in a certain recipe database 555. These data may be utilized to modify conditioning protocols based on attribute data sensed by the sensors 591 and provided to controller 530. Accordingly, the controller 530 could modify or adapt a selected conditioning protocol to be optimized based on certain data sensed by the sensors 591. For example, if a nutritional substance protocol called for a certain surface temperature, or a cooking a nutritional substance 520 at a specific surface temperature sensed by an infrared temperature sensor for a predetermined time, various attribute sensors may modify the recipe or protocol. For instance, if an infrared sensor 591 initially determined that the starting temperature of the nutritional substance 520 was higher than expected or the average recipe is based on, then the target surface temperature may be lowered or raised accordingly, or the total cooking time may be altered, and therefore altering the conditioning protocol. In another example, a weight sensor 591 may determine that the weight of a substance 50 is higher than the average for which a selected conditioning protocol is based on. Accordingly, the target surface temperature may be raised or lowered, or the time for conditioning may be extended or shortened appropriately to optimize the conditioning protocol.

Nutritional substance database 550 may contain information regarding optimal modifications to recipes or conditioning protocols based on various the quantities of various sensed attributes. For example, the database 550 may contain protocol data based on various weights of the same nutritional substance 520. Accordingly, the sensors 591 could then detect the weight of a nutritional substance 520, a conditioning protocol could be retrieved from the database 550, and then the protocol could be modified based on further data, potentially also from the database 550 by the controller 530. For instance, the database 550 may contain equations for calculating optical cooking temperature and/or duration based on the weight of a nutritional substance 520. This could be using various data points and extrapolating between the points for optimal cooking times and/or temperatures, or could be based on a curve fit to certain examples of that specific type of nutritional substance 520 or more general categories of that nutritional substance 520. For example, if a recipe for cooking fish is 2 minutes at 350 per ounce, the controller 530 may vary the recipe appropriately based on a sensed weight of a piece of fish. Additionally, the starting temperature of the fish may affect the total cooking time, and the recipe may be modified accordingly. In other embodiments, the database 550 may contain information regarding various starting temperatures for fish, meat or other nutritional substances 520, and rearrange the entire protocol based on the starting temperature. This may also be applied using, moisture, elevation of conditioner 570, location, ambient humidity, color of nutritional substance 520 (could indicate fat content, spoliation, ripeness, type of nutritional substance 520, etc.) and other attributes sensed by sensors 591. In other embodiments, the consumer 540 may provide input regarding desired options, or based potential $\Delta N$ factors that may be optimized including nutrition, taste, texture, and other factors.

Additionally, in some embodiments, the conditioner 570 may be a combination conditioner 570 that includes the capability to bake, broil, convention cook, microwave, rotate the nutritional substance 520 on a turntable, or perform other conditioning options. These different conditioners may be utilized simultaneously, serially, alone, or in other various combinations to maximize certain $\Delta N$ factors or attributes, or consumer preferences for conditioning the nutritional substance 520.

Accordingly, the database 550 may contain various data points or other indications of the combination of conditioning types that may be utilized to optimally condition a nutritional substance 520 based on the chosen criteria. For example, if a weight sensor 591 detects that a piece of fish weights more than an average piece of fish or a fish sample a conditioning protocol in the database 550 is based on, the controller 530 may elect to condition the fish first by utilizing the microwave to cook the fish through the fastest, so as not to overcook the outside using a convention or other non-microwave cooking option.

An example of such a conditioning protocol for a frozen turkey could be to operate conditioner 570, the combination cooking unit, in the following fashion. In some embodiments, the conditioner 570 may sense the weight, temperature and other attributes of the turkey using a weight measurement sensor, and determine the $\Delta N$ values that would result from different potential conditioning protocols based on information stored in the nutritional substance database 550. This information stored in the nutritional substance database 550, may include the $\Delta N$ values that result from different conditioning protocols based on the weight of the nutritional substance, time, and other conditioning parameters (e.g. cooking temperature). The database may also be easily updatable to allow new $\Delta N$ values to be substituted in based on additional testing or analysis. In these embodiments, the consumer may be presented with various conditioning options and allowed to select the desired conditioning option that results in the desired $\Delta N$ value. Once the consumer selected the conditioning option, the controller 530 may, for example, first instruct conditioner 570 to use the microwave function of the combination cooking unit to defrost the turkey according to the conditioning protocol obtained for the turkey from nutritional substance database 550 and possibly according to information provided by conditioner 570, such as the weight of the turkey obtained from a weight measurement sensor within conditioner 570, information regarding the defrosting process as measured by conditioner 570, or values related to ΔN provided by nutritional attribute sensors before or during defrosting. Following defrosting of the turkey, controller 530 next instructs the combination cooking unit to operate as a convection oven to cook the turkey, according to the conditioning protocol obtained for the turkey from nutritional substance database 550 and the weight of the turkey, for a sufficient length of time so as to ensure that the turkey reaches the proper internal temperature to meet safety requirements, and to maximize organoleptic and/or nutritional properties based on the ΔN and conditioning protocol selected by the consumer and/or determined by the controller 530. Alternatively, or additionally, the conditioning protocol obtained for the turkey from nutritional substance database 550 may depend upon a direct measurement of the internal temperature of the turkey, the weight of the turkey, or a combination of measured temperature and time and weight, or values related to ΔN provided by nutritional attribute sensors before or during conditioning. Following the convection oven cooking of the turkey, controller 530 could instruct the combination cooking unit to grill the turkey, according to the conditioning protocol obtained for the turkey from nutritional substance database 550, for a sufficient period of time to create a desirable golden and crispy skin, which could be based on a modification to a recipe based on sensed attributes of the turkey, including weight, color, moisture and starting temperature. Alternatively, or additionally, the conditioning protocol obtained for the turkey from nutritional substance database 550 may depend upon a direct measurement by a nutritional attribute sensor to measure a ΔN, such as an optical sensor to sense external aesthetic values of the turkey such as color, change of color, texture, or change of texture, temperature, or a weight measurement sensor to sense the weight of the turkey. Alternatively, or additionally, the conditioning protocol obtained for the turkey from nutritional substance database 550 may depend upon a direct measurement by an infrared sensor of the surface temperature of the turkey, or a combination time, measured aesthetic values, weight, and/or measured surface temperature and/or measured ΔN information. Finally, controller 530 could instruct the combination cooking unit to use all three cooking functions at the same time to prepare the turkey for optimal consumption according to the conditioning protocol obtained for the turkey from nutritional substance database 550.

Alternatively, conditioner system 510 could be composed of a plurality of conditioners 570. While an automated system for moving a nutritional substance between such conditioners would be optimal, conditioner system 510 could be operated manually by consumer 540 from instructions provided by the controller 530 to consumer interface 560. In this embodiment, controller 530 could provide consumer 540 with instructions as to where to move the turkey after each step in the conditioning protocol. In this example, controller 530 instructs consumer 540 through consumer interface 560 to first place the frozen turkey in conditioner 570, a microwave oven. Controller 530 instructs the microwave oven to defrost the turkey based on information possibly provided by nutritional substance reader 590, nutritional substance database 550 and/or conditioner 570. Upon completion of defrosting by the microwave oven, controller 530 could instruct consumer 540 through interface 560 to move the defrosted turkey from the microwave oven to another conditioner 570, a convection oven. Controller 530 would operate the convection oven to cook the turkey for a sufficient length of time so as to ensure that the turkey reaches the proper internal temperature to meet safety requirements, and to maximize organoleptic and/or nutritional properties. Finally, following the cooking cycle in the convection oven, controller 530 could instruct consumer 540 through consumer interface 560 to move the turkey from the convection oven to another conditioner 570, a grill. Controller 530 would operate the grill so as to grill the turkey for a sufficient period of time to create a desirable golden and crispy skin. In these embodiments, the consumer 540 may be instructed to place the turkey on an electronic scale to determine the weight of the turkey in between each step, so the conditioning system 510 may record the change in weight of the turkey. The electronic scale may be in electronic communication with the system 510 to allow the weight information to be transferred throughout the system and utilized to calculate an updated ΔN. The change in weight may then be used by the controller 530 to further refine or determine the ΔN from conditioning the turkey and to provide the consumer 540 with updates regarding the ΔN. This may be an alternative to having a weight sensor or scale in each of the conditioners.

Alternatively, conditioner system 510 could be composed of a plurality of conditioners 570; and a consumer 540 (which would include any individuals preparing the turkey for consumption), fulfilling additional conditioner roles, as will be explained. While an automated system for moving a nutritional substance between such conditioners would be optimal, conditioner system 510 could be operated manually by consumer 540 from instructions provided by a consumer interface 560, which in this case could be a handheld device such as a cellular phone, tablet computer, PDA, or any other device useful for communicating with nutritional substance database 550 and the consumer 540. The handheld device additionally fulfills the role of nutritional substance reader 590 and controller 530. For example, the consumer 540 can utilize a camera function of the handheld device to read a barcode, or QR code, on or associated with the turkey, wherein the code provides a dynamic information identifier. The handheld device can then use the dynamic information identifier to retrieve information regarding the turkey from nutritional substance database 550. In this example, consumer 540 utilizes the handheld device to read a barcode (or any other readable code) on the turkey, the barcode containing a dynamic information identifier associated with information regarding the turkey within the nutritional substance database 550. The consumer 540 uses the handheld device to retrieve and review a conditioning protocol from nutritional substance database 550, and is accordingly instructed as to where to move the turkey for each step in the conditioning protocol and further instructed on the conditioning parameters required for each step of the conditioning protocol. In this example, consumer 540 retrieves and reviews a conditioning protocol from nutritional substance database 550 using the handheld device and is instructed to first place the frozen turkey in conditioner 570, a microwave oven, and further instructed on conditioning parameters for the microwave oven to defrost the turkey. Consumer 540 is instructed that upon completion of defrosting by the microwave oven, the turkey is to be moved to another conditioner 570, a convection oven. Consumer 540 is further instructed on conditioning parameters for the convection oven to cook the turkey for a sufficient length of time so as to ensure that the turkey reaches the proper internal temperature to meet safety requirements, and to maximize organoleptic and/or nutritional properties. Finally, consumer 540 is instructed that upon completion of cooking by the convection oven, the turkey is to be moved to another conditioner 570, a grill, and further instructed on conditioning parameters for the grill so as to grill the turkey for a sufficient period of time to create a desirable golden and crispy skin.

In the case where conditioner system 510 is a plurality of conditioners 570, it would also be possible for controller 530 to manage conditioners 570 within conditioner system 510 so as to produce a complete meal. For example, controller 530 could select conditioning protocols which would maximize the use of each conditioner 570. For example, in a meal comprising a turkey, home baked bread, and acorn squash, controller 530 could stage and operate the microwave oven, convection oven, and grill to minimize preparation time for the meal by determining which item should be cooked in which conditioner 570, in which order, to maximize usage of each conditioner 570 in conditioning system 510. In this example, while the turkey is being defrosted in the microwave oven, controller 530 could instruct consumer 540 through interface 560 to place the bread dough in the convection oven and the acorn squash on the grill. Following the defrosting of the turkey, when the turkey is moved to the convection oven, which finished baking the bread, the bread could be moved to the grill for browning, and the acorn squash could be moved to microwave oven to keep warm until the entire meal is ready.

For example, if nutritional substance 520 is a ready-to-eat frozen dinner which needs to be heated by conditioner system 510, nutritional substance reader 590 would read a label on nutritional substance 520, thereby receiving information regarding nutritional substance 520, and then provide the information to controller 530. This information could include creation information as to the creation of the various components which constitute the ready-to-eat dinner. This information could include information about where and how the corn in the ready-to-eat dinner was grown, including the corn seed used, where it was planted, how it was planted, how it was irrigated, when it was picked, and information on fertilizers and pesticides used during its growth. Additionally, this information could include the cattle lineage, health, immunization, dietary supplements that were fed to the cattle that were slaughtered to obtain the beef in the ready-to-eat dinner.

The information from a label on nutritional substance 520 could also include information on how the components were preserved for shipment from the farm or slaughterhouse on their path to the nutritional substance transformer who prepared the ready-to-eat dinner. Additional information could include how the nutritional substance transformer transformed the components into the ready-to-eat dinner, such as recipe used, additives to the dinner, and actual measured conditions during the transformation into the ready-to-eat dinner.

While such information could be stored on a label located on the packaging for nutritional substance 520 so as to be read by nutritional substance reader 590, provided to controller 530, and provided to consumer interface 560 for display to consumer 540, preferably, the label on the nutritional substance package includes reference information, such as a dynamic information identifier, which is read by nutritional substance reader 590 and provided to controller 530 that allows controller 530 to retrieve the information about nutritional substance 520 from nutritional substance database 550. Further, linking consumer feedback and updates regarding observed or measured changes in the nutritional, organoleptic, and/or aesthetic values of nutritional substances would provide for virtually real time updates of $\Delta N$ information from the actual consumer.

Nutritional substance database 550 could be a database maintained by the transformer of nutritional substance 520 for access by consumers of such nutritional substance 520 to track, estimate, or predict changes in the nutritional, organoleptic, and/or aesthetic values of those nutritional substances, including those based on weight and conditioning protocols and other factors, as well as any other information about the nutritional substance that can be tracked, including but not limited the weight of the substances, previous conditioning of the substances and the other examples previously described. However, preferably, nutritional substance database 550 is a database within information module 100 that is maintained by the nutritional substance industry for all such information regarding nutritional substances grown, raised, preserved, transformed, conditioned and consumed by consumer 540, in which case it is the database contained within information module 100 and also referred to herein as a dynamic nutritional value database.

Nutritional substance database 550 may contain information regarding optimal modifications to recipes or conditioning protocols based on various the quantities of various sensed attributes. For example, the database 550 may contain protocol data based on various weights of the same nutritional substance 520. Accordingly, the sensors 591 could then detect the weight of a nutritional substance 520, a conditioning protocol could be retrieved from the database 550, and then the protocol could be modified based on further data, potentially also from the database 550 by the controller 530. For instance, the database may contain equations for calculating optical cooking temperature and/or duration based on the weight of a nutritional substance 520. This could be using various data points and extrapolating between the points for optimal cooking times and/or temperatures, or could be based on a curve fit to certain examples of that specific type of nutritional substance 520 or more general categories of that nutritional substance 520. For example, if a recipe for cooking fish is 2 minutes at 350 per ounce, the controller 530 may vary the recipe appropriately based on a sensed weight of a piece of fish. Additionally, the starting temperature of the fish may affect the total cooking time, and the recipe may be modified accordingly. In other embodiments, the database 550 may contain information regarding various starting temperatures for fish, meat or other nutritional substances 520, and rearrange the entire protocol based on the starting temperature. This may also be applied using, moisture, elevation of conditioner 570, location, ambient humidity, color of nutritional substance 520 (could indicate fat content, spoliation, ripeness, type of nutritional substance 520, etc.) and other attributes sensed by sensors 591. In other embodiments, the consumer 540 may provide input regarding desired options, or based potential $\Delta N$ factors that may be optimized including nutrition, taste, texture, and other factors.

In an alternate embodiment of the present invention, controller 530, in addition to providing information regarding nutritional substance 520 to consumer 540, also receives information from conditioner system 510 on how nutritional substance 520 was conditioned. Additionally, conditioner system 510 may also measure or sense information about nutritional substance 520 before or during its conditioning by conditioner system 510, and provide such information to controller 530, including the weight of the substance 520, so that such information could also be provided to consumer 540, via consumer interface 560. Such information may be sensed by attribute sensors providing information related to ΔN of the nutritional substance to be utilized by the controller to confirm that conditioning parameters currently being implemented will achieve desired residual nutritional, organoleptic, or aesthetic values, and if it is determined that they will not, such information may be used to adaptively modify the conditioning parameters in order to achieve desired residual nutritional, organoleptic, or aesthetic values.

In a preferred embodiment of the present invention, controller 530 organizes and correlates the information it receives regarding nutritional substance 520 from the various sources of such information, including nutritional substance database 550 and conditioner system 510, and presents such information through consumer interface 560 to consumer 540 in a manner useful to consumer 540. For example, such information may be provided in a manner that assists consumer 540 in understanding how nutritional substance 520 meets consumer's 540 nutritional needs before or after conditioning, or how it meets the consumer's needs based on various proposed conditioning parameters. This may include how the nutritional substance's 520 current weight and ΔN will be affected by proposed conditioning parameters. It could organize information regarding nutritional substance 520 to track consumer's 540 weight loss program. Controller 530 could have access to, or maintain, information regarding consumer 540, so as to track and assist consumer 540 in meeting their specific nutritional needs.

In another embodiment of the present invention conditioner system 510 could be a plurality of conditioner devices or dynamic appliances which can be selectively operated by controller 530 to prepare nutritional substance 520. Conditioner system 510 can be either a single conditioning device, such as a microwave oven, toaster oven, conventional oven, toaster, blender, steamer, stovetop, or human cook. Conditioner system 510 may be a plurality of conditioners 570. In the case where a plurality of conditioners 570 comprise conditioner system 510, nutritional substance 520 may be manually or automatically transferred between conditioners 570 for eventual transfer to consumer 540.

Nutritional substance reader 590 may be an automatic reader such as a barcode reader or RFID sensor which receives information from nutritional substance 520 or a reference code from nutritional substance 520, such as a dynamic information identifier, and provides this information to controller 530. Nutritional substance reader 590 might also be a manual entry system where the reference code, such as a dynamic information identifier associated with, or provided with the nutritional substance 520, is manually entered into nutritional substance reader 590 for controller 530.

Nutritional substance database 550 could be a flat database, relational database or, preferably, a multi-dimensional database. Nutritional substance database 550 could be local but, preferably, it would be located remotely, such as on the internet, and accessed via a telecommunication system, such as a wireless telecommunication system. Controller 530 can be implemented using a computing device, such as a microcontroller, micro-processor, personal computer, or tablet computer. Controller 530 could be integrated to include nutritional substance reader 590, consumer interface 560, and/or nutritional substance database 550. Additionally, controller 530 may be integrated in conditioner system 510, including integration into conditioner 570.

It is important to note that while FIGS. 6-9 of various embodiments of the present invention show nutritional substance database 550 as part of the conditioner module 500, they are in no way limited to this interpretation. It is understood that this convention is only one way of illustrating the inventions described herein, and it is further understood that this is in no way limiting to the scope of the present invention. The same is understood for recipe database 555, consumer database 580, and nutritional substance industry database 558. For example, any of nutritional substance database 550, recipe database 555, consumer database 580, and nutritional substance industry database 558 can be contained within information module 100 or within conditioner module 500.

Consumer interface 560 can be implemented as a display device mounted on controller 530, conditioner system 510, or conditioner 570. However, consumer interface 560 is preferably a tablet computer, personal computer, personal assistant, or smart phone, running appropriate software, such as an app.

While conditioner module 500 can be located in the consumer's home, conditioner module 500 may be located at a restaurant or other food service establishment for use in preparing nutritional substances 520 for consumers who patronize such an establishment. Additionally, conditioner module 500 could be located at a nutritional substance seller such as a grocery store or health food store for preparation of nutritional substances 520 purchased by consumers at such an establishment. It could be foreseen that conditioner modules 500 could become standalone businesses where consumers select nutritional substances for preparation at the establishment or removal from the establishment for consumption elsewhere.

Additionally, controller 530 uses nutritional substance information retrieved by nutritional substance reader 590 from nutritional substance 520, or retrieved from nutritional substance database 550 using reference information obtained by nutritional substance reader 590 from nutritional substance 520, to dynamically modify the operation of conditioner system 510 to maintain organoleptic and nutritional properties of nutritional substance 520. For example, if the nutritional substance 520 is a ready-to-eat dinner, controller 530 could modify the instructions to conditioner system 530 in response to information regarding a ΔN of the corn used in the ready-to-eat dinner such that a temperature and cooking duration can be modified to affect the residual nutritional, organoleptic, and aesthetic value of the corn.

In an embodiment, the label on nutritional substance 520 could contain the conditioning instructions for nutritional substance 520, or a reference, such as a dynamic information identifier, to such conditioning instructions in nutritional substance database 550. In operation, this would allow controller 530 to obtain information about nutritional substance 520 on how to dynamically operate conditioner system 510 to condition nutritional substance 520, without consumer intervention. Additionally, conditioning instructions for nutritional substance 520 could be provided for a variety of different conditioner systems 510, or conditioners 570, and controller could select the proper conditioning instructions.

In an embodiment, nutritional substance reader 590 and/or conditioner system 510 measures or senses information about a current nutritional, organoleptic, and aesthetic value of nutritional substance 520, such as with nutritional substance attribute sensors, and provides such information to controller 530 to allow controller 530 to dynamically modify operation of conditioner system 510 including by modifying a conditioning protocol based on previously recorded data regarding conditioning of the nutritional substance 520 at various quantities of the sensed attribute. This may include sensing a weight of the nutritional substance 520, and the conditioner system 510 may be dynamically controlled based on feedback from the weight measurement sensors incorporated or in communication with the conditioner system 510. In other embodiments, a separate scale or appliance with a weight measurement sensor may be provided that allows a consumer to weigh the nutritional substance 520 periodically, before, or after conditioning. The separate scale or appliance may include a nutritional substance reader 590, or may be integrated with the conditioning system 510 and not require a separate reader 590, and rather the information regarding the nutritional substance 520 originally detected by the reader 590 for the system 510 may be automatically associated with the nutritional substance 520 placed on the scale.

For example, a conditioner may also detect certain attributes of nutritional substance 520 through nutritional substance attribute sensors 591. Nutritional substance attribute sensors 591 may be a variety of sensors as disclosed herein, including: (1) weight, (2) a visible light camera, (3) and infrared camera, (3) ambient moisture, (4) ambient temperature, (5) a wireless probe or (6) a spectrometer sensor. The information from the sensors may be provided to controller 530 in addition to or instead of the information provided by nutritional substance reader 590. For example, in some embodiments, the consumer 540 will input information regarding the nutritional substance 520, which may be for example, an identification of the nutritional substance 520, or the general type of nutritional substance 520. Accordingly, the nutritional substance attribute sensors 591 may detect additional information regarding the nutritional substance 520, that may be transferred to the controller 530, including weight, color, surface temperature, probe temperature, ambient temperature once the substance 520 is deposited in the conditioner 570. Data regarding these attributers output from the sensors 591, may be utilized to provide additional information regarding the nutritional substance 520 to the controller 530.

Additionally, various conditioning protocols stored in nutritional substance database 550 may contain data regarding certain attributes that are sensed by nutritional substance attribute sensors 591. These data may be utilized to modify conditioning protocols based on attribute data sensed by the sensors 591 and provided to controller 530. Accordingly, the controller 530 could modify or adapt a selected conditioning protocol to be optimized based on certain data sensed by the sensors 591. For example, if a nutritional substance protocol called for a certain surface temperature, or a cooking a nutritional substance 520 at a specific surface temperature sensed by an infrared temperature sensor for a predetermined time, various attribute sensors may modify the recipe or protocol. For instance, if an infrared sensor 591 initially determined that the starting temperature of the nutritional substance 520 was higher than expected or the average starting temperature a recipe or data set is based on, then the target surface temperature may be lowered or raised accordingly, or the total cooking time may be altered, and therefore altering the conditioning protocol. In another example, a weight sensor 591 may determine that the weight of a substance 50 is higher than the average for which a selected conditioning protocol data set is based on. Accordingly, the target surface temperature may be raised or lowered, or the time for conditioning may be extended or shortened appropriately to optimize the conditioning protocol.

In an additional embodiment of the present invention, consumer 540 provides information regarding their needs and/or desires with regard to the nutritional substance 520 to consumer interface 560. Consumer interface 560 provides this information to controller 530 so as to allow controller 530 to dynamically modify conditioning parameters used by conditioner system 510 in the conditioning of nutritional substance 520, or to request from nutritional substance database 550 dynamically modified conditioning parameters to be used by conditioner system 510 in the conditioning of nutritional substance 520, responsive to the consumer provided information. Consumer's 540 needs and/or desires could include nutritional parameters, taste parameters, aesthetic parameters. For example, consumer 540 may have needs for certain nutrients which are present in nutritional substance 520 prior to conditioning. Controller 530 could modify operation of conditioner system 510 so as to preserve such nutrients. For example, conditioner system 500 can cook the nutritional substance at a lower temperature and/or for a shorter duration so as to minimize nutrient loss. The consumer's 540 needs and/or desires may be related to particular nutritional, organoleptic, an/or aesthetic values, and may additionally be related to other nutritional substance attributes that are retrievable through the nutritional substance database 550 using a dynamic information identifier, such as nutritional substance additives, preservatives, genetic modifications, origins, potential conditioning parameters, and traceability. Further, the consumer's needs and/or desires could be part of a consumer profile provided to the controller 530 through the consumer interface 560 or otherwise available to controller 530. The consumer's needs and/or desires could be exclusionary in nature, for example no products of animal origin, no peanuts or peanut-derived products, no farm raised products, no pork products, or no imported products. In these cases, the nutritional substance database 550 could provide information that would prevent the consumer from preparing and/or consuming products that the consumer cannot, should not, or prefers not to consume.

The consumer's 540 organoleptic and/or aesthetic desires could include how rare or well done they prefer a particular nutritional substance to be prepared. For example, consumer 540 may prefer his vegetables to be crisp or pasta to be prepared al dente. With such information provided by consumer 540 to controller 530 through consumer interface 560, controller 530 can dynamically modify operation of conditioner system 510 responsive to the consumer information and provide a nutritional substance 520 according to the consumer's desires. In addition, the consumer may input certain known or consumer estimated attributes of the nutritional substance 520 in place of them being detected using an information substance reader 590 or attribute sensors 591 when the sensors and/or reader are not available.

In the preferred embodiment of the present invention, controller 530 receives information regarding the history of nutritional substance 520, current information on nutritional substance 520 (e.g. weight), and consumer 540 needs and/or desires, and dynamically modifies operation of conditioner system 510 responsive to the information so as to provide a nutritional substance according to the consumer's needs and/or desires. For example, if nutritional substance 520 is a steak, controller 530 would receive reference information regarding the steak, nutritional substance 520, from nutritional substance reader 590, from attribute sensors 591, including optionally from a weight measurement sensor to determine the weight of the steak. Controller 530 would use this reference information to obtain information about the steak from nutritional substance database 550, including using the weight to determine more precise $\Delta N$ and other organoleptic, nutritional, and aesthetic properties of the steak. Controller 530 could also receive current information about the steak from nutritional substance reader 590 and/or conditioner 510. Additionally, controller 530 could receive consumer 540 preferences from consumer interface 560. Then, the controller 530 may determine potential organoleptic, nutritional, and aesthetic values that may result from various conditioning options for the steak including the associated ΔN values that may result from each of the conditioning options. Next the consumer may enter which of the conditioning options they desire in consumer interface 560. The controller 530 could then modify an existing, or develop a new conditioning protocol to condition the steak to the consumer's preference based on various sensed attributes of the steak, including for example, the weight and color of the steak. For example, in one embodiment, a color sensor may be able to determine the leanness of a steak and implement an optimal condition regime based on the fat content, starting temperature, and weight of the steak. Finally, controller 530 could receive information from conditioner system 510 during the conditioning of the steak, nutritional substance 520. Responsive to some or all of such information, controller 530 would dynamically modify the cooking and/or recipe chosen or adapted for the steak to preserve, optimize, or enhance organoleptic, nutritional, and aesthetic properties to meet consumer 540 needs and/or the desired organoleptic, nutritional, and aesthetic properties or ΔN based on the condition option entered by the consumer. For example, the steak could be cooked slowly to preserve iron levels within the meat, and also cooked to well-done to meet consumer's 540 taste or cooked in another fashion to overall minimize ΔN.

Figure 8:
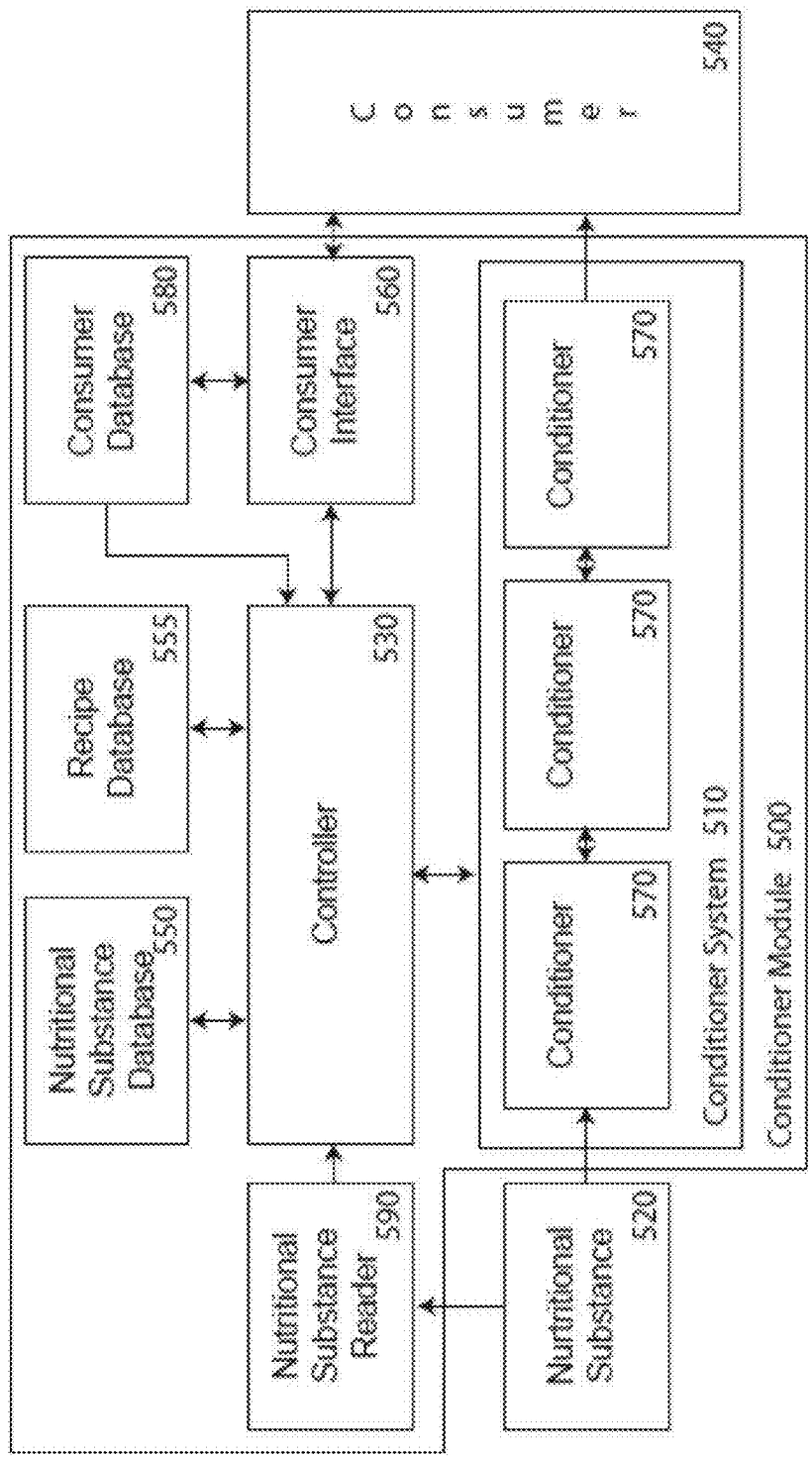
FIG. 8 shows a schematic functional block diagram of a conditioning module according to the present invention.

FIG. 8 shows an embodiment of conditioning module 500 of the present invention. Conditioner system 510 receives nutritional substance 520 for conditioning before it is delivered to consumer 540. Controller 530 is operably connected to conditioner system 510. In fact, controller 530 may be integrated within conditioner system 510, although in FIG. 8, it is shown as a separate device. When conditioner system 510 receives nutritional substance 520 for conditioning, nutritional substance reader 590 either receives information regarding nutritional substance 520 and provides it to controller 530, which is the case if the nutritional substance 520 contains a label which includes the information about nutritional substance 520, and/or the nutritional substance reader 590 receives reference information, such as a dynamic information identifier, and provides it to controller 530, allowing retrieval of the information about nutritional substance 520 from nutritional substance database 550, which is the case when the nutritional substance is associated with, or provided with, a dynamic information identifier. In the case where nutritional substance 520 contains a label which includes information about nutritional substance 520, nutritional substance reader 590 reads this information, provides it to controller 530 and makes it available to consumer 540 by means of consumer interface 560.

In an embodiment of the present invention, conditioner system 510 comprises conditioner 570. Conditioner 570 is a conditioning apparatus which can perform a number of operations on nutritional substance 520, separately and/or at the same time. For example, conditioner 570 could be a combination microwave oven, convection oven, grill, and conventional oven. Controller 530 could operate conditioner 570 to execute a sequence of conditioning cycles on nutritional substance 520 to complete its conditioning.

For example, if nutritional substance 520 is a whole frozen turkey to be prepared for dinner, consumer 540 would place the turkey in conditioner 570, the combination cooking unit suggested above. Controller 530 would receive and/or create a protocol of conditioning cycles. Such a protocol could be read by nutritional substance reader 590 from a label on nutritional substance 520. Alternately, a protocol of conditioning cycles could be obtained from nutritional substance database 550 through reference information such as a dynamic information identifier, obtained by nutritional substance reader 590 from nutritional substance 520. For example, a label on the turkey could be read by nutritional substance reader 590, providing reference information for the turkey, such as a dynamic information identifier, which controller 530 uses to obtain an adaptive conditioning protocol or several options for adaptive conditioning protocols that result in different ΔN values, for the turkey from nutritional substance database 550. The adaptive conditioning protocol obtained is at least partially responsive to ΔN information in the nutritional substance database 550 referenced to the dynamic information identifier.

An example of such a conditioning protocol for a frozen turkey could be to operate conditioner 570, the combination cooking unit in the following fashion. First, controller 530 instructs conditioner 570 to use the microwave function of the combination cooking unit to defrost the turkey according to the conditioning protocol obtained for the turkey from nutritional substance database 550 or selected by the consumer after presented with various conditioning options that are predicted to result in associated ΔN values, and possibly according to information provided by conditioner 570, such as information from attribute sensors regarding the weight, volume, and/or temperature of the turkey, regarding the defrosting process as measured by attribute sensors, or information related to ΔN values provided by attribute sensors before or during defrosting. Information regarding the weight of the turkey could be provided by a weight measurement sensor in the conditioner 570, or it could be a separate appliance or a standalone scale for example that is integrated or separate from conditioning system 510. Additionally, an infrared sensor 591 may detect the surface temperature of the turkey and/or a temperature probe may be placed in the turkey for another level of granularity of information and feedback on the state and varying temperatures of the turkey. Following defrosting of the turkey, controller 530 next instructs the combination cooking unit to operate as a convection oven to cook the turkey, according to the conditioning protocol obtained for the turkey from nutritional substance database 550 and modified by the feedback from the attribute sensors 591 and/or input from the consumer 540, for a sufficient length of time so as to ensure that the turkey reaches the proper internal temperature to meet safety requirements, and to maximize organoleptic and/or nutritional properties or meet the desired ΔN or other requirements entered by the consumer 540. Alternatively, or additionally, the conditioning protocol obtained for the turkey from nutritional substance database 550 may depend upon a direct measurement of the internal temperature of the turkey, or a combination of measured temperature and time, or information related to ΔN values provided by attribute sensors before or during conditioning, including the weight of the turkey, color of the turkey, moisture or humidity, the ambient pressure (i.e. elevation of the conditioner), and other sensed attributes. Following the convection oven cooking of the turkey, controller 530 could instruct the combination cooking unit to grill the turkey, according to the conditioning protocol obtained and/or adapted for the turkey from nutritional substance database 550, for a sufficient period of time to create a desirable golden and crispy skin. Alternatively, or additionally, the conditioning protocol obtained for the turkey from nutritional substance database 550 may depend upon a direct measurement by attribute sensors of a $\Delta N$ value, such as an optical sensor to sense external aesthetic values of the turkey such as color, change of color, texture, or change of texture, temperature, humidity, or other attributes. In other embodiments, a scale or weight measurement sensor in the conditioner 570 may measure the weight of the turkey, and the conditioning protocol may be depend on the direct measurement of the weight and modified during conditioning as the weight of the turkey changes. Alternatively, or additionally, the conditioning protocol obtained for the turkey from nutritional substance database 550 may depend upon a direct measurement by an infrared sensor of the surface temperature of the turkey, or a combination of time, measured aesthetic values, and/or measured surface temperature and/or measured $\Delta N$ information. Finally, controller 530 could instruct the combination cooking unit to use all three cooking functions at the same time to prepare the turkey for optimal consumption according to the conditioning protocol obtained for the turkey from nutritional substance database 550 or entered by the consumer in response to the presentation of different conditioning options and resultant $\Delta N$ values.

Alternatively, conditioner system 510 could be composed of a plurality of conditioners 570. While an automated system for moving a nutritional substance between such conditioners would be optimal, conditioner system 510 could be operated manually by consumer 540 from instructions regarding an adaptive conditioning protocol provided by the controller 530 to consumer interface 560. In this embodiment, controller 530 could provide consumer 540 with instructions as to where to move the turkey after each step in the adaptive conditioning protocol. In this example, controller 530 instructs consumer 540 through consumer interface 560 to first place the frozen turkey in conditioner 570, a microwave oven. Controller 530 instructs the microwave oven to defrost the turkey based on information possibly provided by nutritional substance reader 590, nutritional substance database 550 and/or attribute sensors of the conditioner 570, including weight sensors. Upon completion of defrosting by the microwave oven, controller 530 could instruct consumer 540 through interface 560 to move the defrosted turkey from the microwave oven to another conditioner 570, a convection oven. Controller 530 would operate the convection oven to cook the turkey for a sufficient length of time so as to ensure that the turkey reaches the proper internal temperature to meet safety requirements, and to maximize organoleptic and/or nutritional properties. Finally, following the cooking cycle in the convection oven, controller 530 could instruct consumer 540 through consumer interface 560 to move the turkey from the convection oven to another conditioner 570, a grill. Controller 530 would operate the grill so as to grill the turkey for a sufficient period of time to create a desirable golden and crispy skin.

Alternatively, conditioner system 510 could be composed of a plurality of conditioners 570; and a consumer 540 (which would include any individuals preparing the turkey for consumption), fulfilling additional conditioner roles, as will be explained. While an automated system for moving a nutritional substance between such conditioners would be optimal, conditioner system 510 could be operated manually by consumer 540 from instructions regarding an adaptive conditioning protocol provided by a consumer interface 560, which in this case could be a handheld device such as a cellular phone, smartphone, tablet computer, PDA, or any other device useful for communicating with nutritional substance database 550 and the consumer 540. The handheld device additionally fulfills the roll of nutritional substance reader 590 and controller 530. For example, the consumer 540 can utilize a camera function of the handheld device to read a barcode, or QR code, on or associated with the turkey, wherein the code provides a dynamic information identifier. The handheld device can then use the dynamic information identifier to retrieve information regarding the turkey from nutritional substance database 550. In this example, consumer 540 utilizes the handheld device to read a barcode (or any other readable code) on the turkey, the barcode containing a dynamic information identifier associated with information regarding the turkey within the nutritional substance database 550, including $\Delta N$ information referenced to the dynamic information identifier. The consumer 540 uses the handheld device to retrieve and review an adaptive conditioning protocol from nutritional substance database 550, and is accordingly instructed as to where to move the turkey for each step in the adaptive conditioning protocol and further instructed on the corresponding conditioning parameters required for each step of the adaptive conditioning protocol. The consumer 540 may also be provided various conditioning protocols that result in various $\Delta N$ amounts and are displayed to the consumer. In this example, the consumer 540 may then select one of the adaptive conditioning protocols presented to the consumer 540 from nutritional substance database 550 using the handheld device and will then be instructed to first place the frozen turkey in conditioner 570, a microwave oven, and further instructed on the adaptive conditioning parameters for the microwave oven to defrost the turkey. For a particular protocol, consumer 540 may be instructed that upon completion of defrosting by the microwave oven, the turkey is to be moved to another conditioner 570, a convection oven. Consumer 540 is further instructed on the adaptive conditioning parameters for the convection oven to cook the turkey for a sufficient length of time so as to ensure that the turkey reaches the proper internal temperature to meet safety requirements, and to maximize organoleptic and/or nutritional properties. Finally, consumer 540 is instructed that upon completion of cooking by the convection oven, the turkey is to be moved to another conditioner 570, a grill, and further instructed on the adaptive conditioning parameters for the grill so as to grill the turkey for a sufficient period of time to create a desirable golden and crispy skin.

In the case where conditioner system 510 is a plurality of conditioners 570, it would also be possible for controller 530 to manage conditioners 570 within conditioner system 510 so as to produce a complete meal, and optionally a complete meal that minimizes certain $\Delta N$ values. For example, controller 530 could select conditioning protocols which would maximize the use of each conditioner 570. For example, in a meal comprising a turkey, home baked bread, and acorn squash, controller 530 could stage and operate the microwave oven, convection oven, and grill to minimize preparation time for the meal by determining which item should be cooked in which conditioner 570, in which order, to maximize usage of each conditioner 570 in conditioning system 510. In this example, while the turkey is being defrosted in the microwave oven, controller 530 could instruct consumer 540 through interface 560 to place the bread dough in the convection oven and the acorn squash on the grill. Following the defrosting of the turkey, when the turkey is moved to the convection oven, which finished baking the bread, the bread could be moved to the grill for browning, and the acorn squash could be moved to microwave oven to keep warm, until the entire meal is ready.

For example, if nutritional substance 520 is a ready-to-eat frozen dinner which needs to be heated by conditioner system 510, nutritional substance reader 590 would read a label on nutritional substance 520 thereby receiving information regarding nutritional substance 520, and then provide the information to controller 530. This information could include creation information as to the creation of the various components which constitute the ready-to-eat dinner. This information could include information about where and how the corn in the ready-to-eat dinner was grown, including the corn seed used, where it was planted, how it was planted, how it was irrigated, when it was picked, and information on fertilizers and pesticides used during its growth. Additionally, this information could include the cattle lineage, health, immunization, dietary supplements that were fed to the cattle that were slaughtered to obtain the beef in the ready-to-eat dinner.

The information from a label on nutritional substance 520 could also include information on how the components were preserved for shipment from the farm or slaughterhouse on their path to the nutritional substance transformer who prepared the ready-to-eat dinner. Additional information could include how the nutritional substance transformer transformed the components into the ready-to-eat dinner, such as recipe used, additives to the dinner, and actual measured conditions during the transformation into the ready-to-eat dinner. For example, the information from the label may also contain contingent information to be utilized to optimize a recipe based on various attribute sensors. For example, the label may contain information regarding optimal cooking times and temperatures based on the starting temperature of the read-to-eat frozen dinner as various consumers may set their freezers or refrigerators at different temperatures.

While such information could be stored on a label located on the packaging for nutritional substance 520 so as to be read by nutritional substance reader 590, provided to controller 530, and provided to consumer interface 560 for display to consumer 540, preferably, the label on the nutritional substance package includes reference information, such as a dynamic information identifier, which is read by nutritional substance reader 590 and provided to controller 530 that allows controller 530 to retrieve the information about nutritional substance 520 from nutritional substance database 550, including $\Delta N$ information referenced to the dynamic information identifier. Further, linking consumer feedback and updates regarding observed or measured changes in the nutritional, organoleptic, weight, and/or aesthetic values of nutritional substances would provide for virtually real time updates of $\Delta N$ information from the actual consumer.

Nutritional substance database 550 could be a database maintained by the transformer of nutritional substance 520 for access by consumers of such nutritional substance 520 to track or estimate changes in the nutritional, organoleptic, and/or aesthetic values of those nutritional substances, as well as any other information about the nutritional substance that can be tracked, including but not limited to the examples previously described. However, preferably, nutritional substance database 550 is a database within information module 100 that is maintained by the nutritional substance industry for all such information regarding nutritional substances grown, raised, preserved, transformed, conditioned and consumed by consumer 540, in which case it is the database contained within information module 100 and also referred to herein as a dynamic nutritional value database. The nutritional substance database 550 may contain information regarding $\Delta N$ information for various conditioning protocols applied to specific nutritional substances 520. These $\Delta N$ values may be modified based on a sensed weight of a nutritional substance 520 or other sensed characteristics by nutritional attribute sensors 591, and accordingly utilized to provide precise $\Delta N$ information to a consumer 540 regarding the particular nutritional substance 520 a consumer may consume or plan on conditioning. Additionally, the conditioning protocols may be easily updatable to allow for various changes to the protocols as described herein, and $\Delta N$ information associated with the conditioning protocols may also be updated. Accordingly, the nutritional substance database 550 may be a dynamic database that allows for continually updating and improving the data, so that consumer or end users may have the most current information available or conditioners that access the database 550 may utilize the most current $\Delta N$ information allowing the conditioning protocols to be optimized.

In an alternate embodiment of the present invention, controller 530, in addition to providing information regarding nutritional substance 520 to consumer 540, also receives information from conditioner system 510 on how nutritional substance 520 was conditioned. Attribute sensors of conditioner system 510 may measure or sense information about nutritional substance 520 before or during its conditioning by conditioner system 510, including information related to a nutritional, organoleptic, weight, or aesthetic value of the nutritional substance, or a $\Delta N$, and provide such information to controller 530, so that such information could also be provided to consumer 540, via consumer interface 560. Such sensed information may further be required and utilized by an adaptive conditioning protocol.

In a preferred embodiment of the present invention, controller 530 organizes and correlates the information it receives regarding nutritional substance 520 from the various sources of such information, including nutritional substance database 550 and attribute sensors of the conditioner system 510, and presents such information through consumer interface 560 to consumer 540 in a manner useful to consumer 540. For example, such information may be provided in a manner that assists consumer 540 in understanding how nutritional substance 520 meets consumer's 540 nutritional needs before or after conditioning, or how it meets the consumer's needs based on various proposed conditioning parameters. Thus, in one example, the conditioner system may sense an initial weight of the nutritional substance 520, and determine an initial $\Delta N$ value prior to conditioning the food based on the weight of the substance and the information in the nutritional substance database 550. Then, the consumer 540 could be presented with various conditioning options, and $\Delta N$ values associated with each option so a consumer 540 may determine what is the optimal conditioning method based on their needs. After the consumer 540 selects a conditioning option, and the conditioner 570 conditions the nutritional substance 520, the controller 530 may determine the final nutritional value or $\Delta N$ value of the nutritional substance based on the weight, temperature, color, conditioning protocol and reference information in the nutritional substance database 550. Thus, the consumer 540 can track the precise amount of nutrition ingested during the meal. Accordingly, the controller 530 could organize this information regarding nutritional substance 520 to track consumer's 540 weight loss program. Controller 530 could have access to, or maintain, information regarding consumer 540, so as to track and assist consumer 540 in meeting their specific nutritional needs and potentially suggest optimal weights of nutritional substance 540 and/or conditioning protocols to meet a consumer's 540 goals.

In another embodiment of the present invention conditioner system 510 could be a plurality of conditioner devices which can be selectively operated by controller 530 to prepare nutritional substance 520. Conditioner system 510 can be either a single conditioning device, such as a microwave oven, toaster oven, conventional oven, toaster, blender, steamer, stovetop, or human cook. Conditioner system 510 may be a plurality of conditioners 570. In the case where a plurality of conditioners 570 comprises conditioner system 510, nutritional substance 520 may be manually or automatically transferred between conditioners 570 for eventual transfer to consumer 540.

Nutritional substance reader 590 may be an automatic reader such as a barcode reader, QR code reader, or RFID sensor which receives information from nutritional substance 520 or a reference code from nutritional substance 520, such as a dynamic information identifier, and provides this information to controller 530. Nutritional substance reader 590 might also be a manual entry system where the reference code, such as a dynamic information identifier associated with, or provided with the nutritional substance 520 is manually entered into nutritional substance reader 590 for controller 530.

Nutritional substance database 550 could be a flat database, relational database or, preferably, a multi-dimensional database. Nutritional substance database 550 could be local but, preferably, it would be located remotely, such as on the internet, and accessed via a telecommunication system, such as a wireless telecommunication system. Controller 530 can be implemented using a computing device, such as a microcontroller, micro-processor, personal computer, or tablet computer. Controller 530 could be integrated to include nutritional substance reader 590, consumer interface 560, and/or nutritional substance database 550. Additionally, controller 530 may be integrated in conditioner system 510, including integration into conditioner 570.

It is important to note that while FIGS. 6-9 of various embodiments of the present invention show nutritional substance database 550 as part of the conditioner module 500, they are in no way limited to this interpretation. It is understood that this convention is only one way of illustrating the inventions described herein, and it is further understood that this is in no way limiting to the scope of the present invention. The same is understood for recipe database 555, consumer database 580, and nutritional substance industry database 558. For example, any of nutritional substance database 550, recipe database 555, consumer database 580, and nutritional substance industry database 558 can be contained within information module 100 or within conditioner module 500.

Consumer interface 560 can be implemented as a display device mounted on controller 530, conditioner system 510, or conditioner 570. However, consumer interface 560 is preferably a tablet computer, personal computer, personal assistant, or smartphone, running appropriate software, such as an application.

While conditioner module 500 can be located in the consumer's home, conditioner module 500 may be located at a restaurant or other food service establishment for use in preparing nutritional substances 520 for consumers who patronize such an establishment. Additionally, conditioner module 500 could be located at a nutritional substance seller such as a grocery store or health food store for preparation of nutritional substances 520 purchased by consumers at such an establishment. It could be foreseen that conditioner modules 500 could become standalone businesses where consumers select nutritional substances for preparation at the establishment or removal from the establishment for consumption elsewhere.

Additionally, controller 530 uses nutritional substance information retrieved by nutritional substance reader 590 from nutritional substance 520, or retrieved from nutritional substance database 550 using reference information obtained by nutritional substance reader 590 from nutritional substance 520, to dynamically modify the operation of conditioner system 510 to maintain nutritional, organoleptic, and aesthetic properties of nutritional substance 520. For example, if the nutritional substance 520 is a ready-to-eat dinner, controller 530 could modify the instructions to conditioner system 530 in response to source and $\Delta N$ information regarding corn used in the ready-to-eat dinner such that a temperature and cooking duration can be modified to affect the nutritional, organoleptic, or aesthetic properties of the corn. Further, the dynamically modified conditioning parameters, also referred to herein as adaptive conditioning parameters, may be directly intended to optimize a nutritional, organoleptic, or aesthetic property of the corn targeted by the transformer of the ready-to-eat dinner during transformation.

In an embodiment of the present invention, the label on nutritional substance 520 could contain the conditioning instructions for nutritional substance 520, or a reference, such as a dynamic information identifier, to such conditioning instructions in nutritional substance database 550. The conditioning instructions in such a database may include easily modifiable or replaceable instructions to allow the instructions to be updated but accessed using the same dynamic information identifier. In some embodiments, the label on the nutritional substance 520 could contain a variety of conditioning instructions and an associated $\Delta N$ value by weight of the nutritional substance 520 for each conditioning option. This may also include various contingent conditioning instructions, including weight based, or temperature based conditioning instructions as described herein. In operation, this would allow controller 530 to obtain information about nutritional substance 520 on how to dynamically operate conditioner system 510 to condition nutritional substance 520, without consumer intervention based on the weight of the nutritional substance 520 as determined by a weight sensor or scale integrated with the conditioner 570 or separately connected to the conditioning system 100 as a standalone appliance. Additionally, adaptive conditioning instructions for nutritional substance 520 could be provided for a variety of different conditioner systems 510, or conditioners 570, and controller could select the proper adaptive conditioning instructions, based on, for example, a desired $\Delta N$ value and the weight of the nutritional substance 520. The dynamic operation of conditioner system 510 may be directly intended to optimize a nutritional, organoleptic, or aesthetic property of the nutritional substance targeted by the transformer of the nutritional substance during transformation. In such a case, the operation of conditioner system 510 is according to adaptive conditioning parameters determined by the transformer and responsive to the transformer's knowledge of post transformation residual nutritional, organoleptic, or aesthetic values. The transformer's knowledge of post transformation residual nutritional, organoleptic, or aesthetic values is preferably determined by measurements made during or at completion of transformation, such as data obtained from nutritional substance attribute sensors, including weight sensors.

Adaptive control is the control method used by a controller adapts to a controlled system with parameters which vary or are initially uncertain. In the context of the present disclosure, adaptive control is provided by an adaptive nutritional substance conditioning system responsive to information regarding a nutritional or organoleptic value, including the weight of the substance 520, hydration of the substance 520, or other sensed attributes, before and during conditioning. In an exemplary embodiment the adaptive nutritional substance conditioning system includes a dynamic information identifier associated with a nutritional substance by a provider of the nutritional substance and referenced to a nutritional or organoleptic value determined prior to conditioning. An attribute sensor is provided for sensing information related to the nutritional or organoleptic value during conditioning, which may include a weight sensor or scale. The weight sensor or scale may be integrated with the conditioner 570, to allow the continuous sensing of the weight of the nutritional substance 520 during conditioning. Various other attribute sensors may be included, including (1) weight, (2) a visible light camera, (3) and infrared camera, (3) ambient moisture, (4) ambient temperature, (5) a wireless probe or (6) a spectrometer sensor. A reader reads the dynamic information identifier and retrieves adaptive conditioning parameters referenced to the dynamic information identifier. A controller is provided and configured to provide adaptive conditioning parameters responsive to the nutritional or organoleptic value determined prior to conditioning, the information sensed during conditioning, for maintaining a target post conditioning residual nutritional or organoleptic value. In another exemplary embodiment an adaptive nutritional substance conditioning system includes an attribute sensor for obtaining information related to a nutritional or organoleptic value prior to conditioning and during conditioning. A database is provided comprising historical attribute information for known nutritional substances at known nutritional or organoleptic values. The system also includes a controller configured to provide adaptive conditioning parameters responsive to sensing information obtained prior to conditioning, sensing information obtained during conditioning, and a desired target for the nutritional or organoleptic value following conditioning. The system and database may be a dynamic database that contains dynamic conditioning protocols and associated target nutritional or organoleptic values that may be changed or modified as further testing or consumer feedback determines that certain optimal values are more beneficial.

In an embodiment, information for the adaptive conditioning of a nutritional substance, responsive to a post transformation residual nutritional, organoleptic, or aesthetic value of the nutritional substance or component nutritional substances thereof, as measured by the transformer, is provided by the transformer with the nutritional substance. Such adaptive conditioning information may be provided in any known manner, to be directly read by a reader of the conditioning module, including, but not limited to a dedicated part of a conditioning appliance, a smartphone, or a consumer. Labeling or tags provided with the nutritional substance, such as, but not limited to, QR codes, RFID tags, or written language instructions, could directly communicate the adaptive conditioning information to a reader of the conditioning module, such as an optical scanner, a RFID reader, or a consumer, respectively. Such adaptive conditioning information would comprise one or more adaptive conditioning sequences responsive to the post transformation residual nutritional, organoleptic, or aesthetic value and further responsive to, and unique to, one or more target post conditioning residual nutritional, organoleptic, or aesthetic values, including the weight of the nutritional substance 520. The one or more target post conditioning residual values are predetermined by the transformer and communicated to the consumer as options, such as through written language instructions provided with the nutritional substance, or through a consumer interface of the conditioning module, including, but not limited to, the screen of a conditioning appliance or smartphone. The post adaptive conditioning residual values of a transformed nutritional substance may be determined by the transformer in any known fashion, including, but not limited to, knowledge of a post transformation nutritional, organoleptic, or aesthetic value and estimation of a ΔN associated with specific adaptive conditioning sequences based on historical data regarding ΔNs, knowledge of a post transformation nutritional, organoleptic, or aesthetic value and calculation of a ΔN associated with specific adaptive conditioning sequences based on algorithms developed using historical data regarding ΔNs, or by measurement of the post conditioning residual value after conditioning by specific adaptive conditioning sequences, such as in the transformer's test kitchen or laboratory. Upon selection of the desired option, the corresponding adaptive conditioning sequence can be provided to the controller of the conditioning module. The adaptive conditioning sequence can be entered into the controller of the conditioning appliance manually by the consumer, or might be entered directly by the reader of the conditioning appliance, or by a smartphone communicating in a wired or wireless fashion with the conditioning appliance.

In another embodiment, such adaptive conditioning information may be provided by reference to a unique identifier provided with the nutritional substance, wherein the unique identifier may be read by a reader of the conditioning module, including, but not limited to a dedicated part of a conditioning appliance or a smartphone. Labeling or tags provided with the nutritional substance, such as, but not limited to, QR codes, RFID tags, or written language instructions, could communicate the unique identifier referenced to the adaptive conditioning information to a reader of the conditioning module, such as an optical scanner for scanning a QR code or a RFID reader for scanning a RFID tag. The unique identifier could then be used to retrieve the adaptive conditioning information referenced to it from an adaptive conditioning database. This database may be updatable to allow for additional adaptive conditioning protocols to be added, and/or new information regarding the protocols to be associated with them as described herein. Such a database might be an independent database maintained by the transformer of the nutritional substance or maintained by the nutritional substance industry, and may further be part of the nutritional substance industry database 558 or a part of any database within the nutritional substance industry database 558. The adaptive conditioning information would comprise one or more adaptive conditioning sequences responsive to the post transformation residual nutritional, organoleptic, or aesthetic value and further responsive to, and unique to, one or more target post conditioning residual nutritional, organoleptic, weight, or aesthetic values. The one or more target post conditioning residual values are predetermined by the transformer and communicated to the consumer as options, such as through a consumer interface of the conditioning module, including, but not limited to, the screen of a conditioning appliance or smartphone. The post adaptive conditioning residual values of a transformed nutritional substance may be determined by the transformer in any known fashion, including, but not limited to, knowledge of a post transformation nutritional, organoleptic, or aesthetic value and estimation of a ΔN associated with specific adaptive conditioning sequences based on historical data regarding ΔNs, knowledge of a post transformation nutritional, organoleptic, or aesthetic value and calculation of a ΔN associated with specific adaptive conditioning sequences based on algorithms developed using historical data regarding ΔNs, or by measurement of the post conditioning residual value after conditioning by specific adaptive conditioning sequences, such as in the transformer's test kitchen or laboratory. Upon selection of the desired option, the corresponding adaptive conditioning sequence can be provided to the controller of the conditioning module. The adaptive conditioning sequence can be entered into the controller of the conditioning appliance manually by the consumer, or might be entered directly by the reader of the conditioning appliance, or by a smartphone communicating in a wired or wireless fashion with the conditioning appliance.

Regardless of whether the adaptive conditioning information is provided directly by the nutritional substance or provided by reference to a unique identifier provided with the nutritional substance, the conditioning appliance may be provided with nutritional substance attribute sensors and the adaptive conditioning sequence may require feedback from some or all of the attribute sensors, in which case the nutritional substance is adaptively conditioned responsive to post transformation nutritional, organoleptic, or aesthetic values determined by the transformer, target post conditioning nutritional, organoleptic, or aesthetic values determined by the transformer and selected by the consumer, and feedback from nutritional substance attribute sensors provided before or during conditioning. Such conditioning appliances and adaptive conditioning sequences may be particularly effective in achieving the same desired post conditioning results from different conditioning appliances, different conditioning appliance model numbers, and conditioning appliances from different manufacturers.

In an embodiment of the present invention, nutritional substance reader 590 and/or attribute sensors of conditioner system 510 measure or sense information about the current state of nutritional substance 520, particularly about a nutritional, weight, organoleptic, or aesthetic value, and provides such information to controller 530 before or during conditioning to allow controller 530 to dynamically modify operation of conditioner system 510.

In an additional embodiment of the present invention, consumer 540 provides information regarding their needs and/or desires with regard to the nutritional substance 520 to consumer interface 560. Consumer interface 560 provides this information to controller 530 so as to allow controller 530 to dynamically modify conditioning parameters used by conditioner system 510 in the conditioning of nutritional substance 520, or to request from nutritional substance database 550 dynamically modified conditioning parameters to be used by conditioner system 510 in the conditioning of nutritional substance 520. These parameters provided by the consumer 540 may be saved in a local memory or may be added to a consumer 540 profile in the nutritional substance database 550. Consumer's 540 needs and/or desires could include nutritional parameters, taste parameters, aesthetic parameters. For example, consumer 540 may have needs for certain nutrients which are present in nutritional substance 520 prior to conditioning. Controller 530 could modify operation of conditioner system 510 so as to preserve such nutrients based, for example, on the weight, temperature, or color of the substance. For example, conditioner system 500 can cook the nutritional substance at a lower temperature and/or for a shorter duration so as to minimize nutrient loss, and depending on the overall weight, starting temperature, of the substance may target a specific quantity of a certain nutrient. The consumer's 540 needs and/or desires may be related to particular nutritional, organoleptic, an/or aesthetic values, and may additionally be related to other nutritional substance attributes that are retrievable through the nutritional substance database 550 using a dynamic information identifier, such as nutritional substance additives, preservatives, genetic modifications, origins, and traceability. Further, the consumer's needs and/or desires could be part of a consumer profile provided to the controller 530 through the consumer interface 560 or otherwise available to controller 530. The consumer's needs and/or desires could be exclusionary in nature, for example no products of animal origin, no peanuts or peanut-derived products, no farm raised products, no pork products, no horsemeat products, or no imported products. In these cases, the nutritional substance database 550 could provide information that would prevent the consumer from preparing and/or consuming products that the consumer cannot, should not, or prefers not to consume.

The consumer's 540 nutritional, organoleptic or aesthetic desires could include how rare or well done they prefer a particular nutritional substance to be prepared. For example, consumer 540 may prefer his vegetables to be crisp or pasta to be prepared al dente. With such information provided by consumer 540 to controller 530 through consumer interface 560, controller 530 can dynamically modify operation of conditioner system 510 responsive to the consumer information and provide a nutritional substance according to the consumer's desires.

In an embodiment of the present invention, controller 530 receives information regarding the history of nutritional substance 520, current information on nutritional substance 520, including information regarding a ΔN and weight, and consumer 540 needs or desires, and dynamically modifies operation of conditioner system 510 responsive to the information so as to provide a nutritional substance according to the consumer's needs or desires. For example, if nutritional substance 520 is a steak, controller 530 would receive reference information, such as a dynamic information identifier, regarding the steak, nutritional substance 520, from nutritional substance reader 590, and determine the weight of the steak, using a scale or other weight sensor. Controller 530 would use this reference information to obtain information about the steak from nutritional substance database 550, including information regarding a ΔN and modify the ΔN value based on the weight detected. Controller 530 could also receive current information about the steak from nutritional substance reader 590 or from other attribute sensors of the conditioner 510. Additionally, controller 530 could receive consumer 540 preferences from consumer interface 560. Finally, controller 530 could receive information from attribute sensors of the conditioner system 510 during the conditioning of the steak, nutritional substance 520, including the weight of the steak. Using some or all of such information, controller 530 would dynamically modify the cooking of the steak to preserve, optimize, or enhance organoleptic, nutritional, and aesthetic properties to meet the consumer's 540 needs. For example, the steak could be cooked slowly to preserve iron levels within the meat, and also cooked to well-done to meet consumer's 540 taste.

In a further embodiment, the consumer may provide experience input, such as through consumer interface 560, regarding his experience and satisfaction with the adaptively conditioned nutritional substance. Such experience input may be stored by controller 530, so that it can be utilized in the future for possible further modification of conditioning parameters for similar nutritional substance. In this way, the controller learns how to adapt, or not adapt, conditioning parameters responsive to the consumer's experience input. For example, the consumer input through the consumer interface of a toaster oven when placing a piece of fish into the toaster oven may be that he desires the fish to be rare after conditioning. After conditioning, the consumer may provide his experience input regarding the conditioned fish through the consumer interface, such as by selecting a description of the conditioned fish from a screen providing the options of "under cooked", "rare", "medium", and "well done". If the consumer selected "under cooked", the toaster oven controller could further modify future conditioning parameters for fish to provide longer exposure to heat. If the consumer selected "rare", the controller would not further modify future conditioning parameters for fish. If the consumer selected "medium", the controller could adapt future conditioning parameters for fish to provide less exposure to heat. If the consumer selected "well done", the controller could adapt future conditioning parameters for fish to provide reduced heat and duration of exposure to heat.

Conditioner system 510 can prepare a nutritional substance for consumer 540 which contains a plurality of nutritional substances 520. Conditioner module 500 includes recipe database 555 which is operably connected to controller 530. Recipe database 555 can be part of nutritional substance database 550, or it can be a stand-alone database . . . . While recipe database 555 can be located locally, it is preferably accessible to many conditioner modules 500 through a telecommunications system such as the internet, including wireless telecommunications systems. Accordingly, the recipe database 555 may be contained at a remote server within a center where the recipes can be modified and updated.

In some embodiments, recipe database 555 will contain a database of dynamic recipes or dynamic conditioning protocols that may be modified or replaced. This will allow the recipes to be updated as improvements are made to the recipes or recipes are developed for a particular nutritional substance 520. Accordingly, a manufacturer of food items using the disclosed system would be able to update recipes 555 without printing new labels or reconfiguring electronic tags that store cooking instructions. Accordingly, end users with conditioners 520 that access the recipe database 555 with dynamic recipes will be provided the latest and best available recipes.

The recipe database 555 that has dynamic conditioning protocols or recipes may be indexed in any appropriate fashion and may have a variety of organizational hierarchies and associations. For example, the database may contain certain conditioning protocols that are associated with or linked to certain specific nutritional substances 520. In some embodiments, the nutritional substance 520 will be associated with a dynamic information identifier which may be linked to at least one or a plurality of dynamic conditioning protocols in the recipe database 555. Accordingly, as new nutritional substances 520 are added to the database 555, they may be associated with existing dynamic information identifiers or associated with a new dynamic information identifier. Thus, the conditioning protocols associated with a specific dynamic information identifier may be modified or changed or added to without altering the dynamic information identifier. This will allow the conditioning protocols to be updated or added with minimal cost and disruption to the system. As new dynamic information identifiers are added to the system, they may also be easily associated with existing conditioning protocols to allow for easy adding of new nutritional substances 520 to the system that are similar to existing nutritional substances in recipe database 555.

Dynamic recipes or conditioning protocols may be conditioning protocols that that are updated including by modifying or replacing information in the recipe database 555. Various aspects of the dynamic recipes or conditioning protocols may be updated including total cooking time, target temperatures, or any other factors that may be controlled with a conditioning protocol as disclosed herein. In some embodiments, the dynamic conditioning protocol may be to cook a nutritional substance at a certain temperature for a certain amount of time. In other embodiments, the dynamic conditioning protocols may include other instructions, including a variable or stepped cooking, a curve of temperature versus time for the oven, controls of other aspects of a conditioner 520. Additionally, the dynamic conditioning protocols may include information regarding the type of conditioner 520 employed for usage, or include references to multiple conditioners 520. For example, a recipe for cooking salmon may vary based on whether it is being cooked by a conventional convection oven, a microwave oven, others. In other embodiments, separate conditioning protocols may be utilized for separate conditioners 520. For example, each conditioner may have a different set of dynamic conditioning protocols. These may be stored in the same recipe database 555 or in different recipe databases 555.

In some embodiments, recipes may contain various options that require consumer input 620 once a certain conditioning protocol has been selected. Accordingly, the recipe may contain options or conditional parameters that are implemented based on consumer input. These parameters may be a level of cooking (e.g., well done, medium rare) for meat, crispiness for crust or other nutritional, organoleptic, or aesthetic values. In other embodiments, the consumer 540 may even be presented with various ranges or scales in which a consumer 540 can select a preference over a continuum, for example the range of doneness for meat to fine tune their preference. The associated dynamic conditioning protocol in such an embodiment than may include dynamic ranges and preference indications or requirements that a consumer provide feedback on the doneness.

An example of a dynamic recipe for cooking, wild salmon may include various instructions for a smart oven or other conditioner 570 that includes both convention and microwave elements. The dynamic recipe may first require input of whether the salmon is frozen or chilled. Accordingly, the dynamic recipe may include a thawing out step that is triggered or implemented if consumer input 620 indicates that the salmon is frozen. Additionally, the system may require the salmon to be microwaved first for a brief amount of time to cook the inside, and this may include a microwave execution instruction at a specific intensity for a given amount of time. The recipe may then specify that after the microwaving stage is complete, that a convention oven heating element be initiated at a certain output or temperature for a second time span. In other embodiments, alternating conditioning types, or a variable temperature or intensity scheme may be utilized for the recipe. Additionally, the amount of doneness may also be selected by the consumer.

The dynamic recipe may be a hierarchy of different recipes that may be selected depending on input from the system or a consumer 620 or both. For instance, several recipes may be linked in a tree based on system and consumer input, or the system and consumer input 620 may modify the appropriate portions of the recipe. As one example, the first input may be data indicating the type of conditioner that is requesting the recipe, including either: (1) a convection oven, a (2) microwave oven, (3) or a combination smart oven, or (4) other conditioner types. For each of these types of conditioner 620, there may be a different conditioning protocol linked in the hierarchy that provides instructions to control the specified conditioner 520. Then, the hierarchy may include different types of recipes for a certain type of food. For example, for a piece of chicken there may be the choice of simple backed chicken, chicken parmesan or other recipes. For recipes like chicken parmesan, there may be parts of the recipe that indicate when, for example, cheese should be added and to modify the temperature to optimize the melting and texture of the cheese. After choosing the type of recipe, an end user may also fine tune how they would like the recipe executed. In some embodiments, the recipe or conditioning protocol may include ranges for the temperature and time periods that may result in various nutritional, organoleptic or aesthetic values after conditioning. For example, the temperature may be raised or lowered for certain stages or time periods or raised or lowered overall in order to change the crispiness of chicken skin. Accordingly, these variables may be conditionally built into the recipe to allow for user input 620. The recipe itself may be made of any suitable data structure and variables. In some embodiments, the data structure is constructed to allow for easy modification or replacement of certain portions. The recipe data may also be encrypted as it is sent over networks.

The dynamic recipe may also be updatable or able to replace certain portions in order to account for modifications to the recipe. For example, if testing shows that the organoleptic, aesthetic, or nutritional value is enhanced by a hotter but shorter conditioning period, the cooking temperature and/or time may be modified. In embodiments in which the main recipe comprises multiple recipes in a hierarchy or a recipe with contingent instructions, only certain sub recipes may be updated or contingent portions of the recipe may be updated. In other embodiments, the modification may incorporate a new subordinate recipe in the hierarchy or add a new contingent portion of the recipe that requires consumer input 620. For example, if it is a recipe for backing chicken, perhaps experimental cooking has found that the chicken is better cooked for a very hot final short temperature to obtain crispy skin and the current temperature is too low. There may be a module connected with the database that would receive input from a user interface or automated input that updated the temperature and or time for the final cook. The new temperature data point could then be substitute in the recipe and various sub-portions of the dynamic recipe in the recipe database 555.

The system may also include a conditioner module 500 or controller 530 that retrieves a dynamic conditioning protocol over a port, interface or some kind of input and implements it by controlling the conditioner 570. As described throughout, a conditioner module 500, a conditioner 570, or other components may include a nutritional substance reader 590 that reads a label or other identifying information from the nutritional substance 520 in order to identify the nutritional substance 520. That identity information detected from the nutritional substance 520 or label may then be transmitted to the controller 530, for instance by sending to a port which may be received by a module 500 in which the controller 530 may be incorporated. The controller 530 may then send or reincorporate the data into a request packet(s) sent out of a port or interface over a network to a servers or other computing platforms that host a recipe database 555 and/or a nutritional substance database 550 in order to retrieve or request an appropriate conditioning protocol to be sent back to the same port and/or IP address of the sender or in some embodiments a different address. In some embodiments, the controller 530 may also append information to the packet of information identifying the type or specific conditioner 570 utilized in the requesting system. Accordingly, this may include information regarding what types and the capabilities or specific identity of the conditioner to allow the recipe to be modified or selected to match the conditioner. For example, if the conditioner 570 is a microwave, the conditioning protocol selected would be one that only includes microwave instructions. Additionally, the conditioning protocol selected must be compatible with the particular microwave, as it may have certain settings or pre-set radiation levels that the recipe can only utilize. Accordingly, once a remote server that hosts the database 555 receives the packet, the server will access and send the appropriate dynamic conditioning protocol(s) to the module 500 and/or controller 530. In some embodiments, the server may host several databases and the packet sent may include identifying information specific to the food and/or associated conditioner that allow the server to route the packet to the appropriate database or to request data from the appropriate database.

The recipe information sent over the network back to the module 500 or controller 530 may include instructions directly executable by the controller 530 or module 500 which in turn controls the conditioner 570 or may require a translation module to prepare instructions that are executable directly by the conditioner 570. In some embodiments, these instructions received by the module 500 and/or controller 530 may include an ability to display options for a consumer 540 prior to receiving consumer input 620. This may include displaying the contingent portions of the dynamic conditioning protocol and/or displaying the alternative conditioning options available. For example, various types of recipes and conditioning protocols could be displayed, (e.g. chicken marsala, baked chicken, chicken parmesan) and various ranges or preferences for each type of recipe could be displayed (well done, crispy skin, juicy, etc.). Accordingly, the end user could then enter input regarding their preference for recipe and any specifics required. Once the user input 620 is received, the controller 530 could then process and synthesize the recipe, any information derived from either the recipe database 555 and/or the nutritional substance database 550 and compile or synthesize the data into an executable instruction set that the conditioner 570 may then execute.

In some embodiments the recipe or conditioning protocol may be modifiable in real time via feedback from nutritional substance attributes sensors 591 as disclosed herein or may be modifiable based on consumer modifications during cooking. This may include new or other consumer input 620.

Controller 530 is also preferably connected to consumer database 580. Consumer database 580 may be additionally connected to consumer interface 560. Consumer database 580 could include consumer's 540 organoleptic and nutritional needs, and consumer 540 preferences, and could be in the form of a consumer profile custom tailored to an individual consumer or selected from a menu of consumer profiles. Consumer database 580 may receive input regarding consumer 540 from consumer 540, but could also include information supplied by consumer's 540 medical records, exercise records for the consumer's gym, and other information sources. Consumer database 580 could include information regarding regulatory actions and/or manufacturer warnings or recalls of nutritional substances which may be obtained, have been obtained, or may be prepared or consumed by the consumer. Additionally, consumer database 580 could include information regarding consumer's 540 preferences provided by controller 530 for previous nutritional substance 520 conditionings, and may further include consumer experience input regarding his experience and satisfaction with previously conditioned nutritional substances. Consumer database 580 could include consumer preferences from external sources such as restaurants and grocery stores where consumer 540 purchases nutritional substances 520. Finally, consumer database 580 could include information from consumer module 600, in FIG. 1.

Consumer database 580 could be a local database maintained by controller 530 or consumer interface 560. Preferably, consumer database 580 is part of a nutritional substance industry database containing such information regarding a plurality of consumers 540.

For example, controller 530 can operate to select the necessary ingredients, nutritional substance 520, to prepare a meal. In this case, nutritional substance 520 could be a plurality of nutritional substances 520. In operation, consumer 540 could select a dinner menu using consumer interface 560. Additionally, consumer 540 could select a specific recipe from recipe database 555 or could select a recipe source within database 555, such as low salt meals or recipes by a certain well-known chef. Controller 530 could prepare a shopping list for consumer 540 through consumer interface 560. Alternatively, controller 530 could transmit a shopping list to a nutritional substance 520 supplier such as a grocery store, so consumer 540 could pick up such items already selected or could have such items delivered.

Alternatively, if instructed by consumer 540 to utilize nutritional substances on hand, which have been logged into controller 530 through nutritional substance reader 590, controller 530 could modify or suggest a recipe that used only nutritional substances 520 available to conditioner module 500. For example, if consumer 540 instructs conditioner module 500 through conditioner interface 560 that consumer 540 would like Italian food in the style of a well-known Italian chef, controller 530 would utilize information in its various databases to prepare such a meal. In this case, controller 530 would match its inventory of available nutritional substances with recipes from the well-known Italian chef in recipe database 555 and find available recipes. Controller 530 could select a recipe that optimized consumer's 540 needs and preferences and prepare a meal using conditioner system 510. Alternatively, controller 530 could present various options to consumer 540 using consumer interface 560, highlighting features of each available meal from the standpoint of consumer's 540 nutritional needs and/or preferences. In another embodiment, nutritional substances 520 available to conditioner module 500 may additionally, or alternatively, comprise nutritional substances which have been logged into local storage environments, containers, and coupons in proximity to the conditioner system 510, such as through nutritional substance readers associated with the local storage environments, containers, and coupons.

Figure 9:
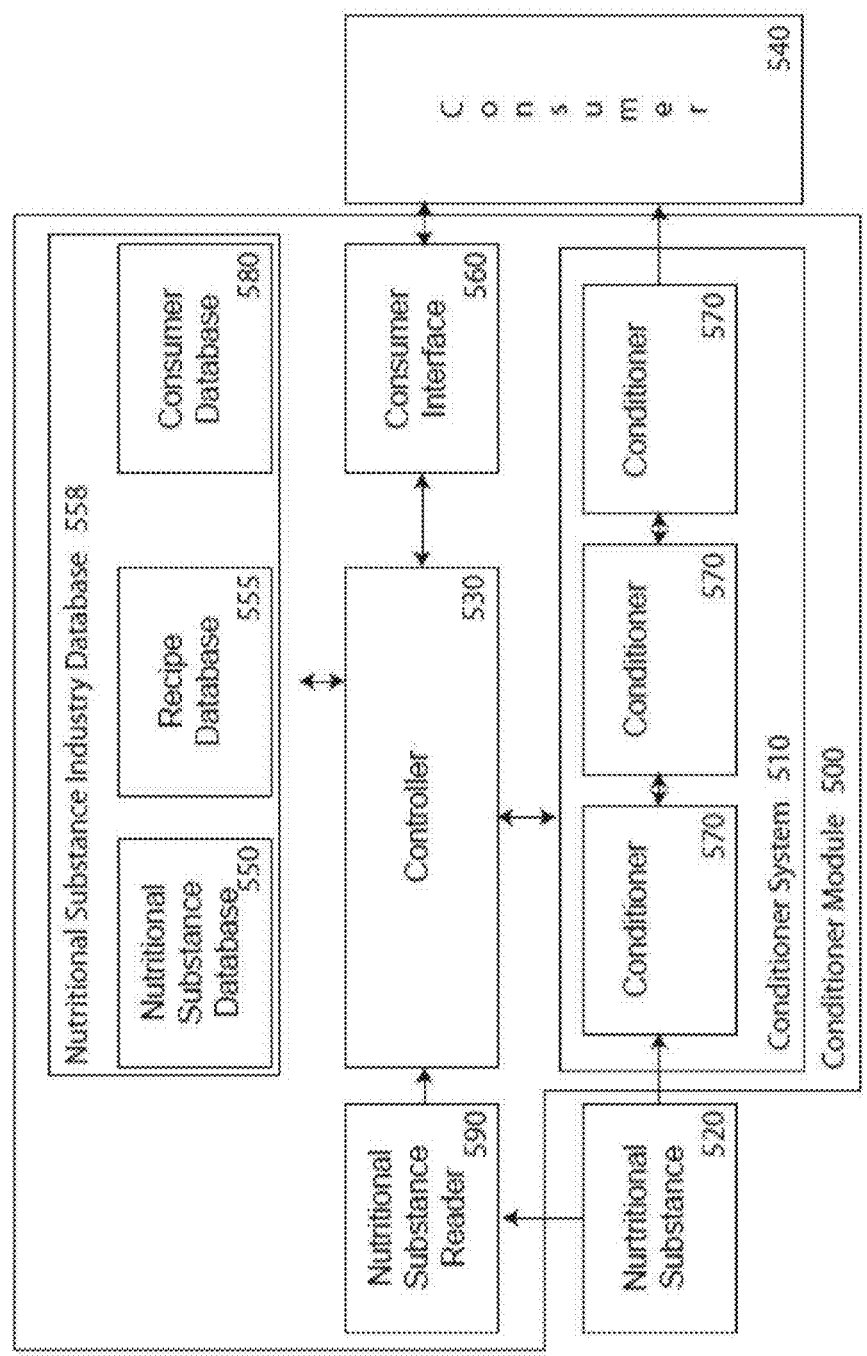
FIG. 9 shows a schematic functional block diagram of a conditioning module according to the present invention.

In FIG. 9, nutritional substance database 550, recipe database 555, and consumer database 580 are part of nutritional substance industry database 558. Controller 530 would communicate with nutritional substance industry database 558 through a communication system such as the internet, and preferably a telecommunications system such as wireless telecommunications. In such an arrangement, controller 530 could even verify that local supermarkets have the items in stock, retrieve and transmit a route to get to the supermarket from the consumer's current location, and further retrieve and transmit a route to follow within the supermarket to efficiently obtain the items.

It is important to note that while FIGS. 6-9 of various embodiments of the present invention show nutritional substance database 550 as part of the conditioner module 500, they are in no way limited to this interpretation. It is understood that this convention is only one way of illustrating the inventions described herein, and it is further understood that this is in no way limiting to the scope of the present invention. The same is understood for recipe database 555, consumer database 580, and nutritional substance industry database 558. For example, any of nutritional substance database 550, recipe database 555, consumer database 580, and nutritional substance industry database 558 can be contained within information module 100 or within conditioner module 500.

In an embodiment of the present invention, a consumer wishing to condition a nutritional substance using a conditioning appliance according to the present invention can determine, and knowingly affect, the true residual nutritional, organoleptic, or aesthetic value of the nutritional substance after he puts it in the conditioning appliance. To do so, the consumer would scan a dynamic information identifier provided with the nutritional substance using a scanner provided with, or associated with, the conditioning appliance. This enables the conditioning appliance's controller to retrieve, from the nutritional substance industry database, information related to changes in nutritional, organoleptic, or aesthetic values ($\Delta N$ information) referenced to the dynamic information identifier. Thereafter, the conditioning appliance controller can request and receive input from the consumer by providing options for the consumer to choose from through a consumer interface, also referred to herein as a dynamic nutritional substance menu panel, which may be a panel, screen, keyboard, or any known type of user interface. The dynamic nutritional substance menu panel provides the consumer with the ability to input the desired end results for the residual nutritional, organoleptic, or aesthetic value that will remain after conditioning, such as by choosing among different possible end results offered by the dynamic nutritional substance menu panel. The controller then creates, or retrieves from the nutritional substance industry database, adaptive conditioning parameters that are responsive to: the $\Delta N$ information retrieved from the nutritional substance industry database using the dynamic information identifier; and the consumer input obtained through the dynamic nutritional substance menu panel. As described herein, the database may contain recipes or adaptive conditioning protocols that have various parameters that are associated with various $\Delta N$ values. This allows a controller 530 to create a specialized recipe optimized to the consumer's desired $\Delta N$ values. In other embodiments, the adaptive conditioning parameters or recipe may first be retrieved from a nutritional substance industry database. Then the parameters may indicate the consumer feedback or preferences are required as input consumer feedback, including the $\Delta N$ values. It is understood that in the case of conditioning appliances provided with nutritional substance attribute sensors, the adaptive conditioning parameters may further be responsive to information provided by the attribute sensors before or during conditioning, including the weight of the nutritional substance 520. It is also understood that in the case of conditioning appliances provided with the ability to obtain experience input from a consumer, the adaptive conditioning parameters may further be responsive to information provided by the consumer regarding a previous consumption of a similar nutritional substance. These adaptive conditioning parameters, also referred to herein as an adaptive preparation sequence, are then communicated to the consumer for implementation through the dynamic nutritional substance menu panel, or alternatively, automatically implemented by the controller.

For example, the consumer 540 is ready to prepare a macaroni and cheese entrée using a combination microwave, convection, and grill oven, according to the present invention. Further, the consumer wants to serve the entrée as soon as possible. The consumer first uses the combination oven's scanner to scan the dynamic information identifier provided with the macaroni and cheese entrée. The dynamic information identifier may be an optically readable label, an RFID tag, or any other known format compatible with the combination oven's scanner, attached to, or incorporated into, the nutritional substance or its packaging. The combination oven controller then retrieves the $\Delta N$ information referenced to the dynamic information identifier from the nutritional substance industry database. The conditioning appliance's controller additionally requests input from the consumer regarding the desired residual nutritional, organoleptic, or aesthetic value of the macaroni and cheese entrée following conditioning, by providing options for the consumer to choose from through its dynamic nutritional substance menu panel. It is understood that these options may be presented in any known fashion, and while particular presentation forms will be discussed herein, they are in no way limiting. In this example, the dynamic nutritional substance menu panel presents options for the consumer to choose from in a format similar to the options provided by routing and navigation applications (i.e. "shortest distance", "shortest time", "least freeway travel", and so forth). For instance, the options provided by the dynamic nutritional substance menu panel may be "fastest preparation time", "highest nutritional value", and "crispy topping" (corresponding to highest organoleptic value for texture). The consumer can find out more detailed information regarding the residual nutritional, organoleptic, and aesthetic values that will result from a particular option by selecting that option, whereupon the dynamic nutritional substance menu panel will provide a summary of the corresponding residual nutritional, organoleptic, and aesthetic values, also referred to herein as a nutritional substance residual value table. The dynamic nutritional substance menu panel may further provide other useful information, such as, but not limited to, the corresponding amount of conditioning time required to achieve the selected option. If the consumer determines that he is not pleased with his selection based upon the more detailed information provided through the dynamic nutritional substance menu panel, particularly the information in the nutritional substance residual value table, he can return to the previous screen and choose another option. The consumer can continue to select options, review the more detailed information in the corresponding nutritional substance residual value table, as well as the other useful information provided, until he determines that an option meets his requirements. Upon determining that an option meets his needs, particularly needs related to the information about residual nutritional, organoleptic, and aesthetic values summarized by the nutritional substance residual value table, the consumer proceeds with the option using the dynamic nutritional substance menu panel, such as by selecting "proceed". The conditioning appliance controller then implements the adaptive preparation sequence, that is, the adaptive conditioning parameters that are responsive to: the $\Delta N$ information it has retrieved from the nutritional substance industry database using the dynamic information identifier provided with the macaroni and cheese entrée; and the consumer input obtained through the dynamic nutritional substance menu panel. The adaptive preparation sequence assures that the consumer will be provided with a conditioned macaroni and cheese entrée that meets his needs, particularly his needs related to residual nutritional, organoleptic, and aesthetic values of the conditioned entrée.

In one example of the present invention, the consumer wishing to prepare the macaroni and cheese entrée selects the "fastest preparation time" option on the dynamic nutritional substance menu panel, as he needs to eat as soon as possible. The dynamic nutritional substance menu panel then provides the consumer with a nutritional substance residual value table showing the residual nutritional, organoleptic, and aesthetic values that will result from adaptively conditioning the macaroni and cheese entrée with the corresponding adaptive preparation sequence, and additionally provides the amount of time required to do so. The consumer determines from the nutritional substance residual value table that one of the entrée's residual nutritional values, for the purpose of this example, its complex carbohydrate content, will be 20% of its starting value. It is understood that the nutritional substance residual value table may provide any number of individual residual nutritional values, such as residual protein content, residual folic acid content, and so forth, and that those provided for the purpose of this example are in no way limiting. It is also understood that residual nutritional value may be provided as an aggregated value based on several independent residual nutritional values. The consumer may additionally determine from the nutritional substance residual value table that the entrée's residual organoleptic value for the crispness of its topping after conditioning, will be 10%, where 0% represents not at all crisp and 100% represents very crisp. It is understood that the nutritional substance residual value table may provide any number of individual residual organoleptic values, such as a rating to determine if the macaroni will be aldente, a rating for overall moistness of the casserole, and so forth, and that those provided for the purpose of this example are in no way limiting. It is also understood that residual organoleptic value may be provided as an aggregated value based on several independent residual organoleptic values. The consumer also determines from the dynamic nutritional substance menu panel that the conditioning will take only 10 minutes. Today, preparation time is the most important criteria to the consumer, so he proceeds by placing the macaroni and cheese entrée into the combination oven, closing its door, and selecting the "proceed" option on the dynamic nutritional substance menu panel. The combination oven can now instruct the consumer through its dynamic nutritional substance menu panel on the various settings and time requirements to adaptively condition the macaroni and cheese entrée according to the adaptive preparation sequence. Alternatively, the combination oven's controller can automatically implement the adaptive preparation sequence, so that the consumer is free to do other things while the entrée is adaptively conditioned. If the combination microwave, convection, and grill oven is provided with nutritional substance attribute sensors, for instance weight measurement sensors, temperature sensors, humidity sensors, or color sensors, the adaptive conditioning parameters might further be modified responsive to information provided by the attribute sensors before or during conditioning. For example, if weight sensors are provided, the adaptive conditioning parameters may be modified to target a specific quantity of a nutrient based on the known quantity of this nutrition retrieved from the nutritional substance database by weight and the dissipation by weight for different conditioning protocols.

Figure 13A:
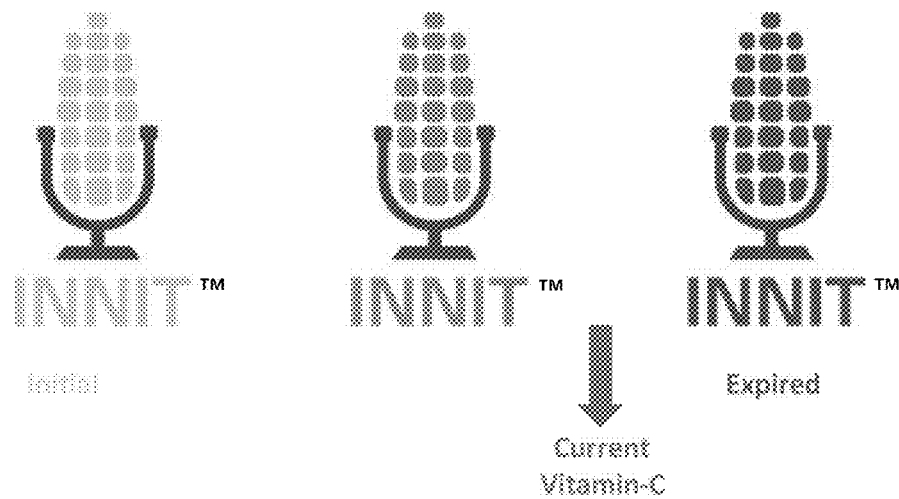
FIGS. 13a and 13b show formats according to the present invention by which a $\Delta N$, and related residual and initial nutritional, organoleptic, and aesthetic values, may be expressed.
Figure 13B:
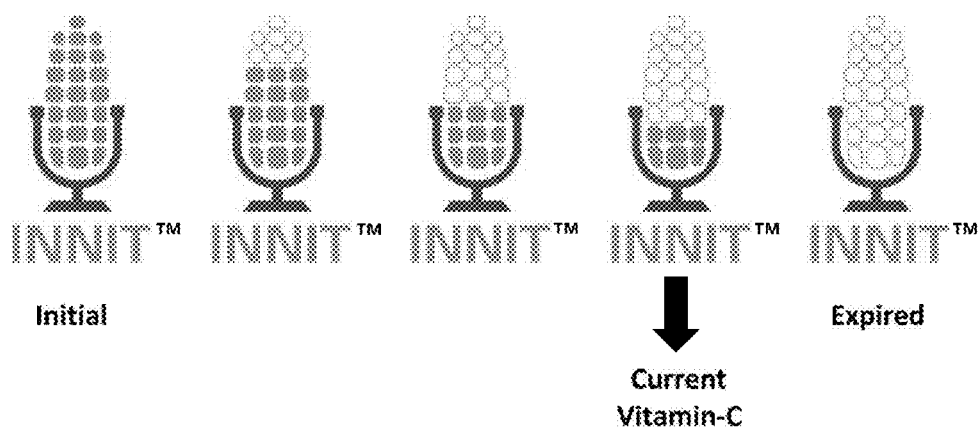

FIGS. 13a and 13b show formats according to the present invention by which a ΔN, and related residual and initial nutritional, organoleptic, and aesthetic values, may be expressed. The ear of corn shown on a microphone stand and labeled "INNIT" in FIGS. 13a and 13b represents a nutritional, organoleptic, or aesthetic value associated with a nutritional substance. While any object may be chosen to represent a nutritional, organoleptic, or aesthetic value, in a preferred embodiment, the chosen object corresponds to a logo, symbol, mascot, or other object associated with a Brand. Such a Brand might be associated with a nutritional substance information system according to the present inventions, a Measurement, Inspection, Engineering, Regulatory, Certification, or other Standard, or any other Brand associated with the nutritional substance and information industry. The object chosen to represent a nutritional, organoleptic, or aesthetic value is also referred to herein as a ΔN meter. In the following examples, the ΔN meter is the ear of corn shown on a microphone stand and labeled "INNIT" shown in FIGS. 13a and 13b, and corresponds to the logo of the provider of a nutritional substance information system according to the present inventions.

In FIG. 13a, a ΔN meter according to the present invention communicates various items regarding a nutritional value, for instance Vitamin-C value, in a corresponding nutritional substance, for instance, a carton of orange juice provided with a dynamic information identifier. A consumer desiring information regarding Vitamin-C values of the orange juice can use his smartphone to scan the dynamic information identifier and determine the desired information. In this example, the information is presented to the consumer on the screen of his smartphone in the form of the ΔN meter shown in FIG. 13a. The ΔN meter of this example communicates symbolically through color, and color changes, the initial Vitamin-C value, the current Vitamin-C value, and an expired Vitamin-C value. The values may be shown as relative values without units of measure, as shown, or may further be provided with actual units of measure. In this example, the consumer is provided with a conceptual indicator regarding how much the Vitamin-C value has degraded relative to its initial value and where its current Vitamin-C value is relative to the expiration value of the Vitamin-C.

In FIG. 13b, a ΔN meter according to the present invention communicates various items regarding a nutritional value, for instance Vitamin-C value, in a corresponding nutritional substance, for instance, a carton of orange juice provided with a dynamic information identifier. A consumer desiring information regarding Vitamin-C levels of the orange juice can use his smartphone to scan the dynamic information identifier and determine the desired information. In this example, the information is presented to the consumer on the screen of his smartphone in the form of the ΔN meter shown in FIG. 13b. The ΔN meter of this example communicates symbolically through percent fill-level, and percent fill-level changes, the initial Vitamin-C value, the current Vitamin-C value, and an expired Vitamin-C value. The values may be shown as relative values without units of measure, as shown, or may further be provided with actual units of measure. In this example, the consumer is provided with a conceptual indicator regarding how much the Vitamin-C value has degraded relative to its initial value and where its current Vitamin-C value is relative to the expiration value of the Vitamin-C.

It is understood that ΔN meters may take many forms and communicate various messages regarding a ΔN value or a residual nutritional, organoleptic, and/or aesthetic value of nutritional substances, and the examples provided above are for illustrative purposes and not intended to be limiting in any way. It is further understood that ΔN meters may be utilized to communicate ΔN values and residual nutritional, organoleptic, and/or aesthetic values determined or estimated in any fashion. In preferred embodiments, the ΔN value or the residual nutritional, organoleptic, and/or aesthetic value are determined utilizing the nutritional substance information systems disclosed herein, including systems utilizing dynamic information identifiers and corresponding nutritional substance database, systems utilizing nutritional attribute sensors and corresponding nutritional substance attribute library, or a combination of both.

On another day, the same consumer is again going to prepare another one of the same macaroni and cheese entrées in his combination oven. He remembers that the last time he did, he was impressed with the speed of preparation, but wished it would have had higher residual complex carbohydrate values and also wished it had a more crispy topping. Today he has no time constraints, and is more interested in the residual nutritional, organoleptic, and aesthetic values that can be achieved. He scans the dynamic information identifier with the scanner on his combination oven. The oven's controller retrieves ΔN information referenced to the dynamic information identifier from the nutritional substance industry database and additionally requests input from the consumer regarding the desired residual nutritional, organoleptic, or aesthetic value of the macaroni and cheese entrée following conditioning, by providing options for the consumer to choose from through its dynamic nutritional substance menu panel. The options are "fastest preparation time", "highest nutritional value", and "crispy topping". The consumer selects the "highest nutritional value" option from the dynamic nutritional substance menu panel, as he wants to eat a healthy meal. The dynamic nutritional substance menu panel then provides the consumer with a nutritional substance residual value table showing the residual nutritional, organoleptic, and aesthetic values that will result from adaptively conditioning the macaroni and cheese entrée with the corresponding adaptive preparation sequence, and additionally provides the amount of time required to do so. The consumer determines from the nutritional substance residual value table that one of the entrée's residual nutritional values, for the purpose of this example, its complex carbohydrate content, will be 80% of its starting value. It is understood that the nutritional substance residual value table may provide any number of individual residual nutritional values, such as residual protein content, residual folic acid content, and so forth, and that those provided for the purpose of this example are in no way limiting. It is also understood that residual nutritional value may be provided as an aggregated value based on several independent residual nutritional values. The consumer may also be interested in the absolute value of carbohydrates rather than the percentage decrease and accordingly a weight sensor or scale may be used to determine the weight of the nutritional substance, from which the actual nutritional content and prospective change from conditioning may be calculated. The consumer may additionally determine from the nutritional substance residual value table that the entrée's residual organoleptic value for the crispness of its topping after conditioning, will be 30%, where 0% represents not at all crisp and 100% represents very crisp. It is understood that the nutritional substance residual value table may provide any number of individual residual organoleptic values, such as a rating to determine if the macaroni will be aldente, a rating for overall moistness of the casserole, and so forth, and that those provided for the purpose of this example are in no way limiting. It is also understood that residual organoleptic value may be provided as an aggregated value based on several independent residual organoleptic values. The consumer also determines from the dynamic nutritional substance menu panel that the conditioning will take 40 minutes. Today, residual nutritional value is the most important criteria to the consumer, so he proceeds by placing the macaroni and cheese entrée into the combination oven, closing its door, and selecting the "proceed" option on the dynamic nutritional substance menu panel. The combination oven can now instruct the consumer through its dynamic nutritional substance menu panel on the various settings and time requirements to adaptively condition the macaroni and cheese entrée according to the corresponding adaptive preparation sequence. Alternatively, the combination oven's controller can automatically implement the adaptive preparation sequence, so that the consumer is free to do other things while the entrée is adaptively conditioned. If the combination microwave, convection, and grill oven is provided with nutritional substance attribute sensors, such as weight sensors, the adaptive conditioning parameters might further be modified responsive to information provided by the attribute sensors before or during conditioning. In this example, the adaptive preparation sequence requires mostly the application of convection heat with a minute of grill at the end of the sequence to cause a small amount of crispness in the topping without burning the cheese exposed to the grill.

On yet another day, the same consumer is again going to prepare another one of the same macaroni and cheese entrées in his combination oven. He remembers that the last time he did, he was impressed with the high residual nutritional value of the entrée, but wondered if he could achieve a still more crispy topping while achieving acceptable residual nutritional value. Today he has no time constraints, and is more interested in the residual nutritional, organoleptic, and aesthetic values that can be achieved. He scans the dynamic information identifier with the scanner on his combination oven. The oven's controller retrieves ΔN information referenced to the dynamic information identifier from the nutritional substance industry database and additionally requests input from the consumer regarding the desired residual nutritional, organoleptic, or aesthetic value of the macaroni and cheese entrée following conditioning, by providing options for the consumer to choose from through a consumer interface, also referred to herein as a dynamic nutritional substance menu panel. The options are "fastest preparation time", "highest nutritional value", and "crispy topping". The consumer selects the "crispy topping" option from the dynamic nutritional substance menu panel, as he initially wants to find out what the residual nutritional value will be if he prepares the entrée according to his organoleptic preference for a crispy topping. The dynamic nutritional substance menu panel then provides the consumer with a nutritional substance residual value table showing the residual nutritional, organoleptic, and aesthetic values that will result from adaptively conditioning the macaroni and cheese entrée with the corresponding adaptive preparation sequence, and additionally provides the amount of time required to do so. On this day, the amount of macaroni and cheese detected by a weight sensor of the conditioning system 510 is less than on the other day, and the prospective nutritional, organoleptic, and aesthetic values that will result from the proposed adaptive conditioning protocols that will be displayed on the dynamic nutritional substance panel will be modified accordingly. The consumer determines from the nutritional substance residual value table that one of the entrée's residual nutritional values, for the purpose of this example, its complex carbohydrate content, will be 75% of its starting value. It is understood that the nutritional substance residual value table may provide any number of individual residual nutritional values, such as residual protein content, residual folic acid content, and so forth, and that those provided for the purpose of this example are in no way limiting. It is also understood that residual nutritional value may be provided as an aggregated value based on several independent residual nutritional values. The consumer may additionally determine from the nutritional substance residual value table that the entrée's residual organoleptic value for the crispness of its topping after conditioning, will be 97%, where 0% represents not at all crisp and 100% represents very crisp. It is understood that the nutritional substance residual value table may provide any number of individual residual organoleptic values, such as a rating to determine if the macaroni will be aldente, a rating for overall moistness of the casserole, and so forth, and that those provided for the purpose of this example are in no way limiting. It is also understood that residual organoleptic value may be provided as an aggregated value based on several independent residual organoleptic values. The consumer also determines from the dynamic nutritional substance menu panel that the conditioning will take 90 minutes. Today, the residual organoleptic value related to the topping crispness is the most important criteria to the consumer, and he has verified that he makes only a small sacrifice in the residual nutritional value to achieve this, so he proceeds by placing the macaroni and cheese entrée into the combination oven, closing its door, and selecting the "proceed" option on the dynamic nutritional substance menu panel. The combination oven can now instruct the consumer through its dynamic nutritional substance menu panel on the various settings and time requirements to adaptively condition the macaroni and cheese entrée according to the corresponding adaptive preparation sequence. Alternatively, the combination oven's controller can automatically implement the adaptive preparation sequence, so that the consumer is free to do other things while the entrée is adaptively conditioned. If the combination microwave, convection, and grill oven is provided with nutritional substance attribute sensors, the adaptive conditioning parameters might further be modified responsive to information provided by the attribute sensors before or during conditioning. In this example, the adaptive preparation sequence requires mostly the application of low convection heat with 3 intervals of 1 minute of grill at the end of the sequence to cause a significant amount of crispness in the topping.

In a further example, the combination microwave, convection, and grill oven in the used to condition the macaroni and cheese entrée is provided with the ability to obtain experience input from the consumer. In this case, the adaptive conditioning parameters may further be responsive to information provided by the consumer regarding previous consumption of macaroni and cheese entrees prepared by the combination oven. For instance, in the past, the consumer's input regarding the desired texture of macaroni in a macaroni and cheese, or possible other pasta entrees, may have been "al dente", however his corresponding experience input indicated that the pasta was "overcooked". The controller of the combination oven can modify the current adaptive conditioning parameters responsive to the previous consumer experience input regarding macaroni and cheese.

Figure 12:
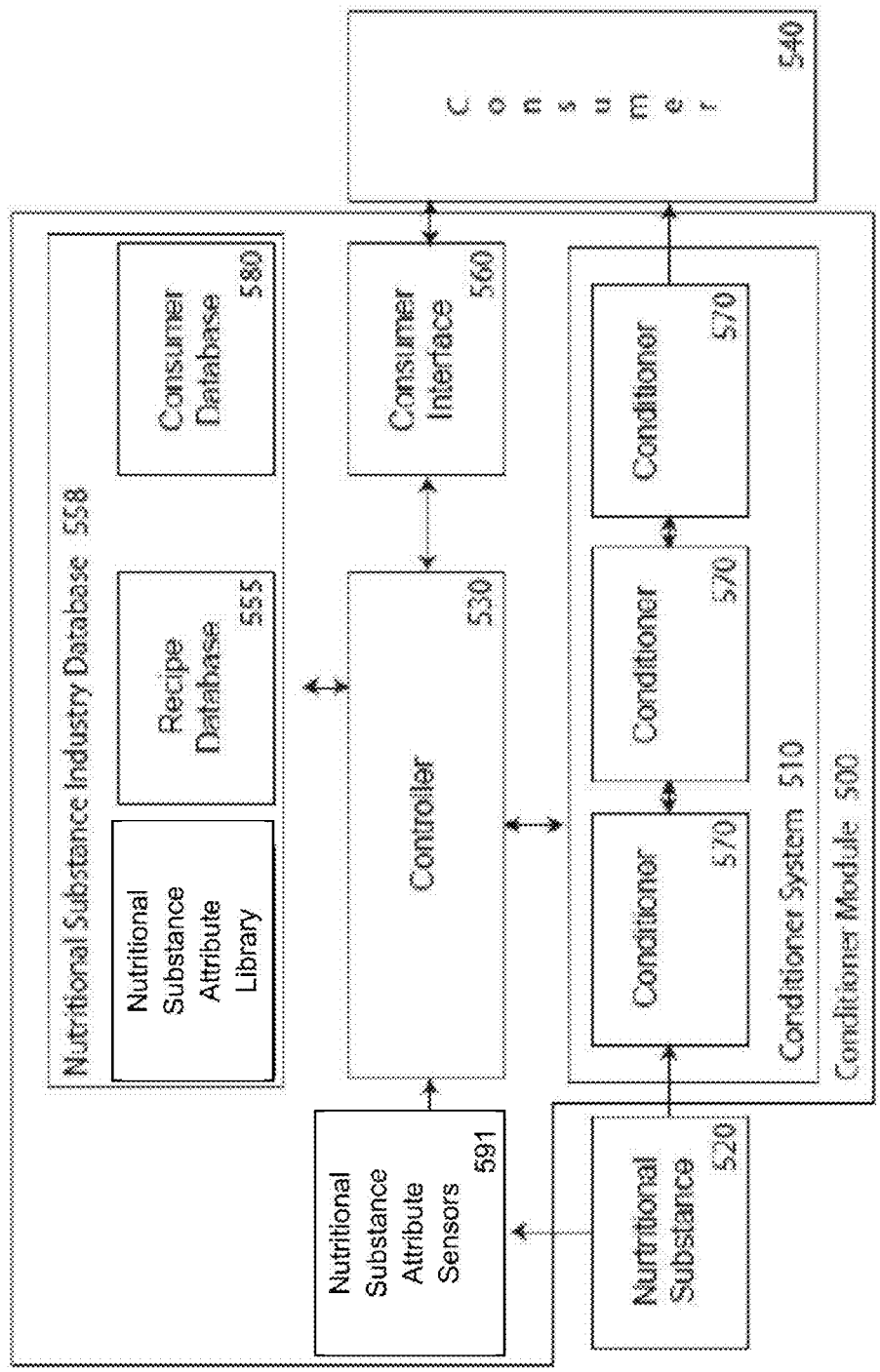
FIG. 12 shows a schematic functional block diagram of a conditioning module according to the present invention.

FIG. 12 shows an alternate embodiment of a conditioner module according to the present invention, wherein a conditioner, also referred to herein as a conditioning appliance, may have features enabling it to communicate with an alternate database that facilitates identification, and the development of optimal conditioning protocols for a nutritional substance. Such features may include, but are not limited to, sensors capable of measuring and collecting data regarding visual appearance, taste, smell, volatiles, texture, touch, sound, chemical composition, temperature, weight, volume, density, hardness, viscosity, surface tension, and any other known physical attribute of the nutritional substance, and are also referred to herein as nutritional substance attribute sensors. These may include, but are not limited to, optical sensors, laser sensors, cameras, electric noses, microphones, olfactory sensors, surface topography measurement equipment, three dimensional measuring equipment, chemical assays, hardness measuring equipment, ultrasound equipment, impedance detectors, temperature measuring equipment, weight measurement equipment, and any known sensor capable of providing data regarding a physical attribute of a nutritional substance. The alternate database would consist of a massive library of nutritional substance attribute data, related to the visual appearance, taste, smell, texture, touch, weight, color, chemical composition and any other known physical attributes, referenced to corresponding nutritional, organoleptic, and aesthetic states of known nutritional substances, and is herein referred to as the nutritional substance attribute library. Additionally, the alternative nutritional substance database would include information regarding conditioning protocols for the nutritional substances 520, and the resulting residual nutritional, organoleptic, and aesthetic values that will be provided based on the conditioning protocols. Furthermore, the database may also contain information how those residual nutritional, organoleptic, and aesthetic values will be affected based on various quantified aspects of the nutritional substances detected by the various sensors and determined by the controller 530. For instance, the database 550 may contain information about the resulting residual nutritional, organoleptic, and aesthetic values of a particular conditioning protocol on a particular nutritional substance 520, and additional data on how the residual nutritional, organoleptic, and aesthetic values would change using the same protocol, if the nutritional substance 520 had different, weight, color, texture, hydration levels, proportions, or other attributes. This may take the form of different data points that are tested and input into the system based on conditioning various nutritional substances 520, for example by conditioning the same type of nutritional substances but using different weights or shapes of it, and measuring the resultant residual nutritional, organoleptic, and aesthetic values through sensors or human feedback. In other examples, the controller 530 may estimate the resulting residual nutritional, organoleptic, and aesthetic values that results from a particular conditioning protocol, on a particular nutritional substance, having particular feature or aspects quantitatively sensed by the sensors 591. It is understood that such conditioning appliances may also be provided with a nutritional substance reader 590, such that they can interact with nutritional substances provided with, and without, dynamic information identifiers. The nutritional substance attribute library may be separate from nutritional substance industry database 558, or is preferably part of the nutritional substance industry database 558. Further, the nutritional substance attribute library may be separate from the nutritional substance database 550, or may exist within nutritional substance database 550. In a preferred embodiment, the nutritional substance attribute library coexists with the nutritional substance database 550, the recipe database 555, and the consumer database 580, within the nutritional substance industry database 558.

There are many examples of sensor technology that might be utilized as a nutritional substance attribute sensor, including, but are not limited to: Surface plasmon resonance sensors (SPR) such as a cell phone based sensor platform disclosed by Preechaburana et at, Angew. Chem. Int. Ed. 2012, 51, 11585-11588, "Surface plasmon resonance chemical sensing on cell phones"; SPR sensors such as those disclosed by Zhang, et al, Zhejiang University, Hangzhou 310058, P.R. China "Detection of penicillin via surface plasmon resonance biosensor"; the combination of microfluidics with Lab-on-a-Chip and Lab-on-a-Foil solutions disclosed by Focke, et al, www.rsc.org/loc, 19 Mar. 2010, "Lab-on-a-Foil: microfluidics on thin and flexible films"; Localized surface plasmon response sensors (LSPR) such as those disclosed by Roche, et al, Journal of Sensors, volume 2011, article ID 406425, doi: 10.1155/2011/406425, "A camera phone localized surface plasmon biosensing platform towards low-cost label-free diagnostic testing"; printed sensors such as those available from Thin Film Electronics ASA, for example the Thinfilm Time-Temperature Sensor; wireless pH sensors such as those discussed in IEE Sensors Journal, Vol 12, No. 3, March 2012 487 "A passive radio-frequency pH sensing tag for wireless food quality monitoring"; sensing of biological quantities such as that discussed in Appl Microbiol Biotechnol (2013) 97:1829-1840 "An overview of transducers as platform for the rapid detection of foodborne pathogens"; cell phone based E. Coli sensor using florescent imaging to detect bacteria in food and water, developed at UCLA Henry Samueli School of Engineering and Applied Science; sensors discussed in Journal of Food Engineering 100 (2010) 377-387 "Biomimetric-based odor and taste sensing systems to food quality and safety characterization: An overview on basic principals and recent achievements"; sensors discussed in Sensors 2010, 10, 3411-3443, doi 10.3390/s100403411 "Advanced Taste Sensors Based on Artificial Lipids with Global Selectivity to Basic Taste Qualities and High Correlation to Sensory Scores"; sensing described in Chem. Sci., 2012, 3, 2542 "Fluorescent DNAs printed on paper: sensing food spoilage and ripening in the vapor phase"; the use of a Silicon Integrated Spectrometer to sense food for ripeness and other qualities is described in IEEE Photonics Journal, 1 (4), p. 225-235 (2009); electronic noses like those discussed by Walt DR., Anal chem 2005 77:A-45; electronic noses like those discussed by Gardner J W et al., Electronic noses: principles an applications. Oxford University press, New York, 1999; colorimetric sensor arrays like those discussed by Suslick et al., Anal Chem 2010 82(5):2067-2073; numerous sensing techniques described in analytica chima acta 605 (2007) 111-129 "A review on novel developments and applications of immunosensors in food analysis"; numerous sensing techniques described in J. Biophotonics 5, No. 7, 483-501 (2012)/doi 10.1002/jbio.201200015 "Surface plasmon resonance based biosensor technique: A review"; LSPR techniques to sense bitterness of tea described in Agric. Food Chem., 2010, 58 (14), pp 8351-8356 "B-Cyclodextrin/Surface plasmon response detection system for sensing bitter astringent taste intensity of green tea catechins"; a review on nano-biosensors to measure tastes and odors discussed in Bio-Nanotechnology: A revolution in food biomedical and health sciences, first edition, 2013, John Wiley & Sons, Ltd. "Nano-Biosensors for mimicking gustatory and olfactory senses"; techniques described in Science Daily, http://www.sciencedaily.com/releases/2013/02/130214111612.htm, 14 Feb. 2013 "World's most sensitive plasmon resonance sensor inspired by the ancient roman cup"; ethylene sensors discussed in Anal. Chem., 2011, 83 (16), pp 6300-6307, doi: 10.1021/ac2009756 "Electrochemical sensing of ethylene employing a thin ionic-liquid layer"; multiplex SPR techniques described in Anal Bioanl Chem (2011) 400: 3005-3011, doi 10.1007/s00216-011-4973-8 "Imaging surface plasmon resonance for multiplex microassay sensing of mycotoxins"; a review of noble metal nono-optical sensors based on LSPR by Zhao, et al, "Localized surface plasmon resonance biosensors"; colorimetric plasmon resonance imaging described by Gartia, et al, Advanced Optical Materials 2013, 1, 68-76, doi: 10.1002/adom.201200040 "Colorimetric plasmon resonance imaging using nano Lycurgus cup arrays"; sensor using multiplex fiber-optic biosensor implemented by integrating multiple particle plasmon resonances (PPRs), molecular bioassays, and microfluidics is disclosed by Lin, et al, Proc. SPIE 8351, Third Asia Pacific Optical Sensors Conference, 83512S (Jan. 31, 2012), doi: 10.117/12.914383 "Multiplex fiber-optic biosensor using multiple particle plasmon resonances"; sensor based on multilayered graphene SPR-based transmission disclosed by Kim, et al, J. Nonosci. Nanotechnol, 2012 Jul. 12(7):5381-5 "Evaluation of multi-layered graphene surface plasmon resonance-based transmission type fiber optic sensor"; sensors to detect Mercury values such as the biosensors, chemical sensors, conductometric sensors, microcantilevel sensors, SAW sensors, piezoelectric sensors, and nanosensors similar to those described by: Selid et al, Sensors 2009, 9, 5446-5459; doi: 10.3390/s90705446; and Katherine Davies, Royal Society of Chemistry, Chemistry World, New chemosensor for mercury detection (http://www.rsc.org/chemistryworld/Issues/2005/July/mercury_detection.asp); sensors to detect caffeine values may be similar to those described by: Chung I C, et al, J Nanosci Nanotechnol. 2011 December; 11(12):10633-8, A portable electrochemical sensor for caffeine and (−) epigallocatechin gallate based on molecularly imprinted poly(ethylene-co-vinyl alcohol) recognition element; or Ebarvia, et al, Analytical and Bioanalytical Chemistry, March 2004, Volume 378, Issue 5, pp 1331-1337, Biomimetic piezoelectric quartz sensor for caffeine based on a molecularly imprinted polymer.; or Zhao, et al, http://www.researchgate.net/publication/225410860, Department of Material and Chemistry Engineering, Henan Institute of Engineering, Zhengzhou, 450007 China, Article-Voltammetric sensor for caffeine based on a glassy carbon electrode modified with Nafion and graphene oxide; sensors to detect sugar values may be similar to those described by: Kumar, et al, Study of fiber optic sugar sensor; or Scampicchio, et al, Nanotechnology 20 135501 doi:10.1088/0957-4484/20/13/135501, Issue 13, 1 Apr. 2009, Optical nanoprobes based on gold nanoparticles for sugar sensing; sensors to detect temperature values may be similar to those manufactured by MICRO-EPSILON, and described at www.micro-epsilon as miniature non-contact IR sensors thermoMETER CSmicro and non-contact IR sensors with laser aiming thermoMETER CSlaser; sensors for detecting temperature values may also include any thermocouple type sensor suitable for contact sensing of temperature. It is understood that sensors may be configured to perform multiple test assays in a single use to develop a multidimensional dataset from each use.

Other examples of sensor technology that might be utilized include sensors similar to those manufactured by MICRO-EPSILON and described at www.micro-epsilon as fixed lens color sensors color SENSOR OT-3-GL and OT-3-LU. These sensors illuminate a surface with white light and sense the reflected color values, and are particularly useful for color recognition of non-homogeneous targets and glossy targets, for instance, a piece of beef or other animal tissue packaged in clear cellophane, packaged in shrink-wrap, or not currently packaged. These sensors can also provide useful information regarding the turbidity of liquids. Alternatively, sensors may be similar to those manufactured by MICRO-EPSILON and described at www.micro-epsilon as fiber color sensors, color SENSOR LT-1-LC-20, WLCS-M-41, and LT-2. These sensors use a modulated white light LED to project a spot onto or through a target, and focusing part of the reflected or transmitted light with fiber optic onto a color detector element. Common sensing techniques include, but are not limited to: projecting a spot directly on and normal to an inspection target and focusing part of the back-scattered light with fiber optic onto a color detector; projecting a spot indirectly, that is at an angle to, an inspection target and focusing part of the reflected light with fiber optic onto a color detector; and projecting a spot directly through an inspection target and focusing part of the transmitted light with fiber optic onto a color detector. Such a nutritional substance attribute sensor may be configured to include a white light source and color detector as a permanent part of a detector, for instance, a detector provided as part of a nutritional substance reader or dynamic appliance reader, and a coupler that enables attachment of the detector to the mating coupler of various fiber optic probe configurations to project light from the light source onto or through a target and to focus reflected or transmitted light from the target onto the color detector. Such fiber optic probes may be provided as a permanent part of a sealed nutritional substance package, wherein the portions of the probe required to interface with the nutritional substance are in direct contact with the nutritional substance, and the mating coupler that allows removable attachment to the sensor coupler provided with the detector is available externally of the package. Permanently incorporating the sensor probe into the package has many benefits. The portion of the sensor probes in contact with the nutritional substance can be tailored to the specific product and package, while the mating coupler on the outside of the package is always provided in the configuration compatible with the sensor coupler on the detector. This enables sensing of a wide array of packaged nutritional substances without disrupting package integrity. It also simplifies the task greatly for a user, and ensures consistent and accurate sensing technique.

Sensing technologies utilizing hyperspectral imaging are potentially useful as nutritional substance attribute sensors, and because of their speed and ability to provide in-process detection, may be particularly useful for applications during local storage and conditioning of nutritional substances. Hyperspectral imaging may be utilized in some embodiments of the present invention, for example, for in-line inspection of multiple produce items, such as apples or strawberries, as they are placed into a dynamic appliance such as a refrigerator, or alternatively, for rapid inspection of meat products such as poultry or seafood, as they are removed from a dynamic appliance such as a refrigerator, or placed into a dynamic appliance such as a toaster oven. This technology is particularly useful for identifying anomalies in nutritional substances without disrupting the nutritional substance. All substances have unique spectral signatures, which can be saved in a library. Libraries including the spectral responses of known nutritional substances in known nutritional, organoleptic, or aesthetic conditions, and further including known sources of adulteration, such as fecal matter, chemical contamination, micro-organisms and other pathogens or disease conditions, can be used for comparison to spectral responses of nutritional substances currently being sensed, and in this way the currently sensed nutritional substance can be quickly identified according to desired criteria. Hyperspectral sensing may further be utilized for plant and crop phenotyping, whereby a composite of a nutritional substance's observable characteristics provides a unique nutritional substance fingerprint. This can be particularly beneficial to rule out adulteration such as by partial or total ingredient substitution, and may be accomplished by an appropriately equipped dynamic appliance.

Sensing technologies utilizing near-infrared spectroscopy may be potentially useful as nutritional substance attribute sensors, because of their ability to provide detection below the surface of a sensed object, may be particularly useful for identifying the type and concentration of various components of a nutritional substance. Examples of this type of sensor include the microPHAZIR RX from Thermo Fisher Scientific and near-infrared technologies under development by Fraunhofer Institute for Electronic Nano Systems.

Other examples of optical sensor technology that might be utilized include, but are not limited to: handheld Raman spectrometers available from Serstech, www.serstech.com; PinPointer™ handheld Raman spectrometer available from Ocean Optics, www.oceanoptics.com; TruScan RM handheld Raman spectrometer available from Thermo Fisher Scientific; near infra-red sensor available from Thermo Fisher Scientific; Xantus Mini™ remote controlled, smartphone compatible Raman spectrometer available from Rigaku, www.rigaku.com; Lighting Passport handheld or remote smartphone compatible spectrometer from Asensetek, www.alliedscientificpro.com.

At this juncture it can be understood that a nutritional, organoleptic or aesthetic value of a nutritional substance can be indicated by its olfactory values or its taste values. Typically, but not necessarily, olfactory values and taste values are detectable by the human sense of smell. However, nutritional substances may emit or produce gaseous components that are not detectable or discernible by the human sense of smell, or components not detectable or discernible by human sense of taste, but, nevertheless, may be indicative of a particular nutritional, organoleptic, and aesthetic state of the nutritional substance. In addition, olfactory values and taste values can be indicative of adulteration of nutritional substances, such as by spoilage, contamination, or substitution of other nutritional substances.

It is understood that the utilization of the nutritional substance attribute sensors according to the present invention can provide beneficial information regarding adulteration or mislabeling of nutritional substances.

In an example of a conditioning appliance equipped with nutritional substance attribute sensors, a consumer places a turkey breast in a combination microwave, convection, and grill oven equipped with nutritional substance attribute sensors. The nutritional substance attribute sensors collect a variety of physical attribute data from the turkey breast. The conditioning appliance's controller then transmits the physical attribute data collected to the nutritional substance industry database, for comparison to the nutritional substance attribute library contained therein. For example, the weight, color, temperature, texture, moisture, or other attributes of the turkey breast may be detected and communicated to the nutritional substance attribute library. It is understood that while FIG. 12 shows the nutritional substance industry database as part of the conditioner module, it may reside in the information module. It is further understood that while the nutritional substance attribute library is shown as part of the nutritional substance industry database, this only for the purposes of example and not intended to be limiting in any way, and it may reside within the information module or may exist as an independent database. When a match is found for the physical attribute data collected from the turkey breast placed in the conditioning appliance, the nutritional substance industry database can determine that the matching nutritional substance attribute library dataset corresponds to a turkey breast with known nutritional, organoleptic, and aesthetic values, and that it weighs 2 pounds, it is at a certain hue, it has a certain texture, and is at a temperature of 40 deg. F. Thereafter, the conditioning appliance controller can request input from the consumer by providing options for the consumer to choose from through a consumer interface, also referred to herein as a dynamic nutritional substance menu panel, which may be a panel, screen, keyboard, or any known type of user interface. The dynamic nutritional substance menu panel provides the consumer with the ability to input the desired end results for the residual nutritional, organoleptic, or aesthetic value that will remain after conditioning, such as by choosing among different possible end results offered by the dynamic nutritional substance menu panel. The controller 530 then creates, or retrieves from the nutritional substance industry database, adaptive conditioning parameters that are responsive to: the nutritional, organoleptic, and aesthetic value information retrieved from the nutritional substance industry database using the nutritional substance attribute library including adjustments made as necessary for the sensor attribute data and the consumer input obtained through the dynamic nutritional substance menu panel. These adaptive conditioning parameters, also referred to herein as adaptive preparation sequence, are then communicated to the consumer for implementation through the dynamic nutritional substance menu panel, or alternatively, automatically implemented by the controller, or adapted based on feedback from the attribute sensors 591 in the conditioner 570.

In the above example, the consumer is ready to prepare a turkey breast using a combination microwave, convection, and grill oven equipped with nutritional substance attribute sensors. The consumer places the turkey breast in the combination oven, where the oven's nutritional substance attribute sensors sense various physical attribute data from the turkey breast, for example the weight, color, temperature, and texture. The combination oven controller then transmits the sensed attribute data to the nutritional substance industry database for comparison to the nutritional substance attribute library. The nutritional substance industry database determines that the sensed data matches the nutritional substance attribute library dataset corresponding to turkey breast having specific nutritional, organoleptic, and aesthetic values, and a certain weight and temperature. The conditioning appliance's controller additionally requests input from the consumer regarding the desired residual nutritional, organoleptic, or aesthetic value of the turkey breast following conditioning, by providing options for the consumer to choose from through its dynamic nutritional substance menu panel. It is understood that these options may be presented in any known fashion, and while particular presentation forms will be discussed herein, they are in no way limiting. In this example, the dynamic nutritional substance menu panel presents options for the consumer to choose from in a format similar to the options provided by routing and navigation applications (i.e. "shortest distance", "shortest time", "least freeway travel", and so forth). For instance, the options provided by the dynamic nutritional substance menu panel may be "fastest preparation time", "highest nutritional value", and "tender" (corresponding to highest residual organoleptic value for texture). The consumer can find out more detailed information regarding the residual nutritional, organoleptic, and aesthetic values that will result from a particular option by selecting that option, whereupon the dynamic nutritional substance menu panel will provide a summary of the corresponding residual nutritional, organoleptic, and aesthetic values, also referred to herein as a nutritional substance residual value table. The dynamic nutritional substance menu panel may further provide other useful information, such as, but not limited to, the corresponding amount of conditioning time required to achieve the selected option based on, among other factors, the weight of the nutritional substance. If the consumer determines that he is not pleased with his selection based upon the more detailed information provided through the dynamic nutritional substance menu panel, particularly the information in the nutritional substance residual value table, he can return to the previous screen and choose another option. The consumer can continue to select options, review the more detailed information in the nutritional substance residual value table, as well as the other useful information provided, until he determines that an option meets his requirements. Upon determining that an option meets his needs, particularly needs related to the information about residual nutritional, organoleptic, and aesthetic values summarized by the nutritional substance residual value table, the consumer can proceed with the option by using the dynamic nutritional substance menu panel, such as by selecting "proceed". The conditioning appliance controller then implements adaptive conditioning parameters that are responsive to: the information it has retrieved from the nutritional substance industry database by comparing sensed physical attribute data to the nutritional substance attribute library; and/or the consumer input obtained through the dynamic nutritional substance menu panel. These adaptive conditioning parameters, also referred to herein as adaptive preparation sequence, assure that the consumer will be provided with an adaptively conditioned turkey breast that meets his needs, particularly his needs related to residual nutritional, organoleptic, and aesthetic values of the adaptively conditioned turkey breast.

In one example of the present invention, the consumer wishing to prepare the turkey breast selects the "fastest preparation time" option on the dynamic nutritional substance menu panel, as he needs to eat as soon as possible. The dynamic nutritional substance menu panel then provides the consumer with a nutritional substance residual value table showing the residual nutritional, organoleptic, and aesthetic values that will result from adaptively conditioning the turkey breast with the corresponding adaptive preparation sequence, and additionally provides the amount of time required to do so for the piece of turkey at the certain temperature and weight, for example. The consumer determines from the nutritional substance residual value table that one of the turkey breast's residual nutritional values, for the purpose of this example, its residual protein content, will be 60% of its starting value or may provide the residue value or change in value in an actual quantity of protein such as 50 grams remaining or a decrease of 30 grams of protein. It is understood that the nutritional substance residual value table may provide any number of individual residual nutritional values, such as residual complex carbohydrate content, residual fat content, residual folic acid content, and so forth, and that those provided for the purpose of this example are in no way limiting. It is also understood that residual nutritional value may be provided as an aggregated value based on several independent residual nutritional values. The consumer may additionally determine from the nutritional substance residual value table that the turkey breast's residual organoleptic value for tenderness after conditioning will be 10%, where 0% represents not at all tender and 100% represents very tender. It is understood that the nutritional substance residual value table may provide any number of individual residual organoleptic values, such as a rating to determine if the turkey breast will be well done, a rating for overall moistness of the turkey breast, and so forth, and that those provided for the purpose of this example are in no way limiting. It is also understood that residual organoleptic value may be provided as an aggregated value based on several independent residual organoleptic values. The consumer also determines from the dynamic nutritional substance menu panel that the adaptive conditioning will take only 8 minutes. Today, preparation time is the most important criteria to the consumer, so he proceeds by selecting the "proceed" option on the dynamic nutritional substance menu panel. The combination oven can now instruct the consumer through its dynamic nutritional substance menu panel on the various settings and time requirements to adaptively condition the turkey breast according to the corresponding adaptive preparation sequence. Alternatively, the combination oven's controller can automatically implement the adaptive preparation sequence, so that the consumer is free to do other things while the turkey breast is adaptively conditioned. The adaptive preparation sequence may further be responsive to input obtained from one or more attribute sensors during conditioning. In this example, the adaptive preparation sequence requires mostly the application of microwave at high intensity with a few seconds of grill at the end of the sequence to cause a small amount of crispness in the skin.

On another day, the same consumer is again going to prepare a similar turkey breast in his combination oven. He remembers that the last time he did, he was impressed with the speed of preparation, but wished it would have had higher residual protein value and also wished it had been more tender. Today he has no time constraints, and is more interested in the residual nutritional, organoleptic, and aesthetic values that can be achieved. He places the turkey breast in the combination oven, where the oven's nutritional substance attribute sensors sense various physical attribute data from the turkey breast, including its weight and temperature. The conditioning appliance's controller then transmits the physical attribute data collected to the nutritional substance industry database, for comparison to the nutritional substance attribute library contained therein. In other examples, the physical attributes may include elevation, ambient pressure in the conditioner, texture, moisture, relative humidity in the conditioner, color of the turkey, and other attributes. When a match is found for the physical attribute data collected from the turkey breast, the nutritional substance industry database can determine that the matching nutritional substance attribute library dataset corresponds to a turkey breast with known nutritional, organoleptic, and aesthetic values, and that it weighs 2.2 pounds and is at a temperature of 42 deg. F. The controller additionally requests input from the consumer regarding the desired residual nutritional, organoleptic, or aesthetic value of the turkey breast following conditioning, by providing options for the consumer to choose from through its dynamic nutritional substance menu panel. The options are "fastest preparation time", "highest nutritional value", and "tender". The consumer selects the "highest nutritional value" option from the dynamic nutritional substance menu panel, as he wants to eat a healthy meal. The dynamic nutritional substance menu panel then provides the consumer with a nutritional substance residual value table showing the residual nutritional, organoleptic, and aesthetic values that will result from adaptively conditioning the turkey breast with the corresponding adaptive preparation sequence, and additionally provides the amount of time required to do so. The consumer determines from the nutritional substance residual value table that one of the turkey breast's residual nutritional values, for the purpose of this example, its protein content, will be 90% of its starting value, 90 grams total or a change in 10 grams. It is understood that the nutritional substance residual value table may provide any number of individual residual nutritional values, such as residual complex carbohydrate content, residual folic acid content, residual fat content, and so forth, and that those provided for the purpose of this example are in no way limiting, and this data could be provided in many different forms, such as percentages, graphs, or absolute values. It is also understood that residual nutritional value may be provided as an aggregated value based on several independent residual nutritional values. The consumer may additionally determine from the nutritional substance residual value table that the turkey breast's residual organoleptic value for tenderness after conditioning will be 50%, where 0% represents not at all tender and 100% represents very tender. It is understood that the nutritional substance residual value table may provide any number of individual residual organoleptic values, such as a rating to determine if the turkey breast will be well done, a rating for overall moistness of the turkey breast, and so forth, and that those provided for the purpose of this example are in no way limiting. It is also understood that residual organoleptic value may be provided as an aggregated value based on several independent residual organoleptic values. The consumer also determines from the dynamic nutritional substance menu panel that the conditioning will take 40 minutes. Today, residual nutritional value is the most important criteria to the consumer, so he proceeds by selecting the "proceed" option on the dynamic nutritional substance menu panel. The combination oven can now instruct the consumer through its dynamic nutritional substance menu panel on the various settings and time requirements to adaptively condition the turkey breast according to the corresponding adaptive preparation sequence. Alternatively, the combination oven's controller can automatically implement the adaptive preparation sequence, so that the consumer is free to do other things while the turkey breast is adaptively conditioned. The adaptive preparation sequence may further be responsive to input obtained from one or more attribute sensors during conditioning. In this example, the adaptive preparation sequence requires mostly the application of convection heat with two minutes of grill at the end of the sequence to cause a small amount of crispness in the skin without burning the skin exposed to the grill.

On yet another day, the same consumer is again going to prepare a similar turkey breast in his combination oven. He remembers that the last time he did this he was impressed with the high residual nutritional value of the turkey breast, but wondered if he could achieve a still more tender turkey breast with acceptable residual nutritional values. Today he has no time constraints, and is more interested in the residual nutritional, organoleptic, and aesthetic values that can be achieved. He places the turkey breast in the combination oven, where the oven's nutritional substance attribute sensors sense various physical attribute data from the turkey breast. The conditioning appliance's controller then transmits the physical attribute data collected to the nutritional substance industry database, for comparison to the nutritional substance attribute library contained therein. When a match is found for the physical attribute data collected from the turkey breast, the nutritional substance industry database can determine that the matching nutritional substance attribute library dataset corresponds to a turkey breast with known nutritional, organoleptic, and aesthetic values, and that it weighs 2.1 pounds and is at a temperature of 41 deg. F. In other examples, the physical attributes may include elevation, ambient pressure in the conditioner, texture, moisture, relative humidity in the conditioner, color of the turkey, and other attributes. The controller additionally requests input from the consumer regarding the desired residual nutritional, organoleptic, or aesthetic value of the turkey breast following conditioning, by providing options for the consumer to choose from through its dynamic nutritional substance menu panel. The options are "fastest preparation time", "highest nutritional value", and "tender". The consumer selects the "tender" option from the dynamic nutritional substance menu panel, as he prefers to eat a tender piece of turkey breast if he can determine that it is still a healthy meal. The dynamic nutritional substance menu panel then provides the consumer with a nutritional substance residual value table showing the residual nutritional, organoleptic, and aesthetic values that will result from adaptively conditioning the turkey breast with the corresponding adaptive preparation sequence, and additionally provides the amount of time required to do so. The consumer determines from the nutritional substance residual value table that one of the turkey breast's residual nutritional values, for the purpose of this example, its residual protein content, will be 88% of its starting value. It is understood that the nutritional substance residual value table may provide any number of individual residual nutritional values, such as residual complex carbohydrate content, residual folic acid content, residual fat content, and so forth, and that those provided for the purpose of this example are in no way limiting. It is also understood that residual nutritional value may be provided as an aggregated value based on several independent residual nutritional values. The consumer may additionally determine from the nutritional substance residual value table that the turkey breast's residual organoleptic value for tenderness after conditioning will be 98%, where 0% represents not at all tender and 100% represents very tender. It is understood that the nutritional substance residual value table may provide any number of individual residual organoleptic values, such as a rating to determine if the turkey breast will be well done, a rating for overall moistness of the turkey breast, and so forth, and that those provided for the purpose of this example are in no way limiting. It is also understood that residual organoleptic value may be provided as an aggregated value based on several independent residual organoleptic values. The consumer also determines from the dynamic nutritional substance menu panel that the conditioning will take 80 minutes. Today, residual organoleptic value, specifically tenderness, is the most important criteria to the consumer, so he proceeds by selecting the "proceed" option on the dynamic nutritional substance menu panel. The combination oven can now instruct the consumer through its dynamic nutritional substance menu panel on the various settings and time requirements to adaptively condition the turkey breast according to the corresponding adaptive preparation sequence. Alternatively, the combination oven's controller can automatically implement the adaptive preparation sequence, so that the consumer is free to do other things while the turkey breast is adaptively conditioned. The adaptive preparation sequence may further be responsive to input obtained from one or more attribute sensors during conditioning. In this example, the adaptive preparation sequence requires mostly the application of low convection heat with two cycles of 3 minutes of grill at the end of the sequence to cause a moderate amount of crispness in the skin.

In a further embodiment, the consumer may provide experience input, such as through consumer interface 560, regarding his experience and satisfaction with the adaptively conditioned nutritional substance. Such experience input may be stored by controller 530, so that it can be utilized in the future for possible further modification of conditioning parameters for similar nutritional substances. In this way, the controller learns how to adapt, or not adapt, conditioning parameters responsive to the consumer's experience input. For example, the consumer input through the consumer interface of a toaster oven when placing a turkey breast into the toaster oven may be that he desires it to be rare after conditioning. After conditioning, the consumer may provide his experience input regarding the conditioned turkey breast, such as by selecting a description of the conditioned turkey breast from a screen providing the options of "under cooked", "rare", "medium", and "well done". If the consumer selected "under cooked", the toaster oven's controller could further modify future conditioning parameters for turkey breast to provide longer exposure to heat. If the consumer selected "rare", the controller would not further modify future conditioning parameters for turkey breast. If the consumer selected "medium", the controller could adapt future conditioning parameters for turkey breast to provide less exposure to heat. If the consumer selected "well done", the controller could adapt future conditioning parameters for turkey breast to provide reduced heat and duration of exposure to heat.

In another embodiment, a conditioning appliance is provided with nutritional substance reader 590 and nutritional substance attribute sensors 591. The nutritional substance reader 590 scans a dynamic information identifier associated with a nutritional substance, and the nutritional substance attribute sensors 591 scan the nutritional substance. The controller of the conditioning appliance uses the dynamic information identifier to determine the nutritional substance content and current nutritional, organoleptic, or aesthetic value referenced to the dynamic information identifier in the nutritional substance database. The controller uses the data obtained from the nutritional substance attribute sensors to determine the nutritional substance content and current nutritional, organoleptic, or aesthetic value corresponding to the values in the nutritional substance attribute library, including for example the weight of the nutritional substance. In other examples, the physical attributes may include elevation, ambient pressure in the conditioner, texture, moisture, relative humidity in the conditioner, color of the turkey, and other attributes. The controller compares the nutritional substance content and nutritional, organoleptic, or aesthetic value information determined from the nutritional substance database to that determined from the nutritional substance attribute library. If the information is determined to be similar, adaptive conditioning parameters responsive to the current nutritional, organoleptic, and aesthetic values of the nutritional substance can be provided. If the information is determined to be dis-similar, adaptive conditioning parameters may not be provided, or alternatively, the consumer may be provided with options through the consumer interface. Options may include, but are not limited to, proceeding with conditioning by manually entered conditioning parameters; proceeding with adaptive conditioning parameters responsive to information determined from nutritional substance database; proceeding with adaptive conditioning parameters responsive to information determined from nutritional substance attribute library; or not proceeding with conditioning.

Figure 14:
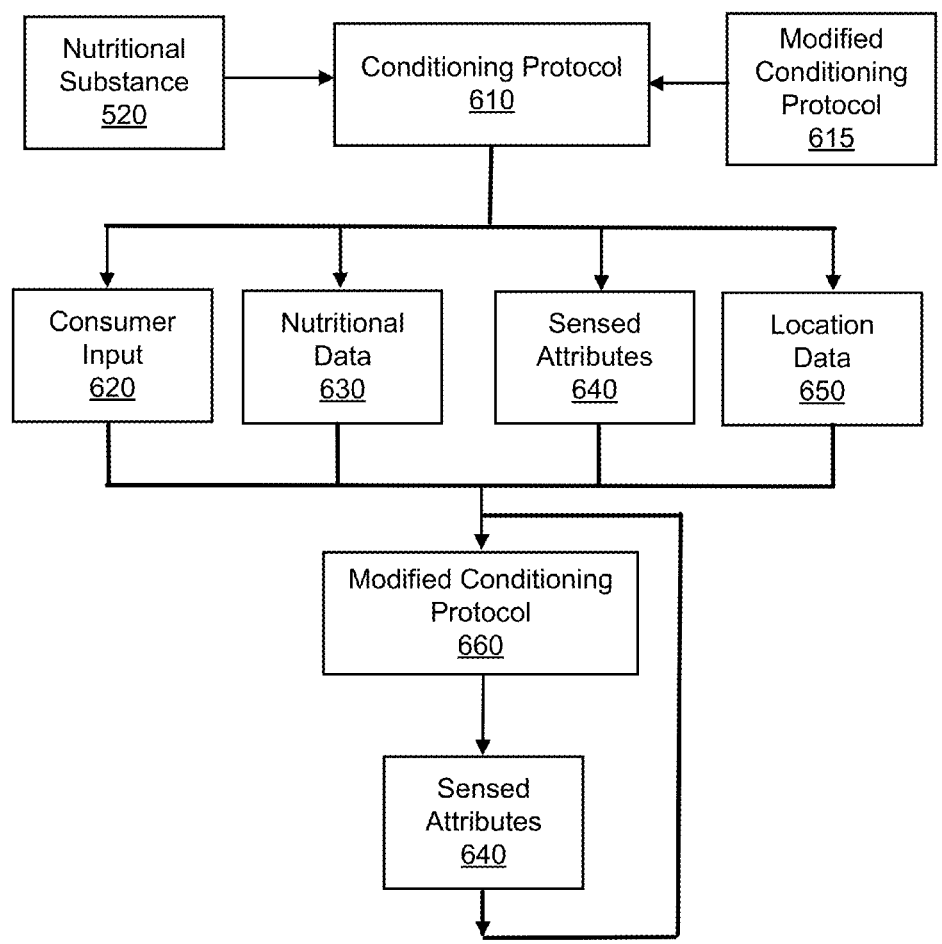
FIG. 14 shows a schematic functional block diagram of a process for modifying a conditioning protocol accordingly to the present invention.

FIG. 14 illustrates an embodiment of a process for adapting a conditioning protocol 610 to the following factors: (1) consumer input 620, (2) nutritional data 630 or data sets on changes in nutrition resulting from various conditioning protocols (3) sensed attributes 640 of a specific nutritional substance 520 useful for determining the effect of the conditioning protocol 610 on the actual substance 520, and (5) geographic location data 650 regarding the location of the food that can be used to determine the ambient pressure, elevation, humidity, or other location based factors that may be relevant to conditioning a nutritional substance 520 and changes in the resulting nutritional, organoleptic, or aesthetic values from conditioning. These five attributes or others may be utilized to modify or adjust a conditioning protocol 610 to optimize it for a particular nutritional substance 520, and produce a modified conditioning protocol 660. For instance, a conditioning protocol 610 for a certain type of nutritional substance, 520, for example, salmon, may be accessed from a nutritional substance database 550 by a controller 530, in order to retrieve of potential condition protocols 610 or a base conditioning protocol that may be further refined or selected to optimize the conditioning protocol 610 for the particular nutritional substance 520 (i.e. piece of salmon) and to optimize it to the consumer preferences based on consumer input 620. Then once the conditioner 570 and controller 530 receives input regarding from attribute sensors 591, from the consumer 540, from GPS data 650, from the nutritional values database 550, and any other relevant sources, this data may be utilized to modify the conditioning protocol 660 to optimize it for a particular amount or portion of nutritional substance 520. As described herein, the conditioning protocols 610 may be modified or altered in the database based on new testing data, or other features. This will allow the end user or conditioning device to access the most current conditioning protocols.

For instance, a piece of salmon may be scanned with the nutritional substance reader 590, or identified using the attribute sensors 591. The sensors 591 used to identify the nutritional substance 520 may be colorimetric sensor arrays, color sensors, spectrometer, standard optical detectors or others matching profiles using statistical analysis or other methods as disclosed herein. Next, once the category or type of nutritional substance 520 is identified, (i.e. salmon) the specific attributes of that nutritional substance 520 may be identified and stored as sensed attributes 640. These sensed attributes 640 may include the initial weight of the salmon, the color (i.e. wild versus farm raised), the initial temperature, the texture, the shape, and other relevant factors. In other embodiments, these attributes may be wholly or partially obtained from a nutritional substance reader 590 associated with the conditioner 570 that reads a nutritional substance identifier where the nutritional substance is pre weighed, and the other attributes are predetermined before packaging and provided on information in a label or in a database. In some embodiments, only the nutritional substance is identified, and no specific attributes are sensed 640 and rather average or estimated data is utilized. Next, the conditioner optionally may consider location data, including using GPS, or consumer input 620 to determine the local ambient conditions that are relevant to conditioning. For example, certain climates may be more humid or certain geographic locations may have significantly different elevations that substantially affect cooking Next, various information or nutritional data 630 may be stored in the nutritional information database 550 regarding the nutritional substance 520 (i.e. salmon) and how the nutritional, organoleptic, or aesthetic values of the nutritional substance 520 changes based on various conditioning protocols. This nutritional data 630, or change in nutritional data may be obtained from prior tests of conditioning protocols on various nutritional substances 520, including the same type of nutritional substances but in different quantities, initial temperatures, initial colors, and other sensed attributes 640. Accordingly, this information may be utilized to predict how a particular nutritional substance 520 will change over various conditioning protocols based on its unique sensed attributes 640, including how it's various nutritional, organoleptic, or aesthetic values will change. Accordingly, this may be an estimated change.

A database 550 or recipe database 555 that provides information on sensed attributes 640 may include information on, various weights, lengths, and shapes of salmon that were conditioned using various protocols and the resulting nutritional, organoleptic, or aesthetic values that were recorded. For instance, a larger piece of salmon will need to be cooked longer to ensure the inside is not raw, but also that the outside is not tough and rubbery. Contrarily, a smaller piece of salmon will need a different conditioning protocol to optimally condition the salmon without overcooking it, or denaturing too many of its omega three fatty acids. Accordingly, the database 550 may have the appropriate cooking time for various weights of salmon, and use that to extrapolate in between for a particular piece of salmon or to accommodate its precise sensed weight. Additionally, the same could be performed for starting temperature, color and other sensed attributes 640. In other embodiments, mathematical models may be developed based on experimental data for conditioning certain types of foods, for instance more popular foods such as fish or salmon that are notoriously harder to condition to perfection without sensing the attributes of the actual nutritional substance about to be conditioned. Additionally, the location of the conditioner 570 may be utilized to determine the ambient pressure and other characteristics that are important to cooking times and utilized to output a modified conditioning protocol 660.

Then, the controller 530 may output various conditioning options to the consumer for conditioning the salmon as disclosed herein, to maximize nutritional, organoleptic, or aesthetic values, or other consumer preferences. The controller 530 would then take the consumer input 620 to further modify the conditioning protocol to output a new modified conditioning protocol 660 that may be implemented to condition the salmon. For example, the consumer may input their desire to preserve the maximum amount of omega 3 fatty acids in the piece of salmon. Therefore, the controller 530 will determine based on the modified conditioning protocols 660 provided by input from the sensed attributes 640, nutritional data 630, and location data 650, how to further modify the protocols or select the optimum protocol to maximize the omega three content of the salmon. For instance, it may be known, or testing may show that both microwaving and the shortest cooking time maximize the omega 3. Therefore, the conditioner may the implement the modified conditioning protocol 660 that primarily or solely microwaves the fish. In another embodiment, a combination of microwaving and convection or grilling may be used for a modified conditioning protocol 660 that preserves most omega threes but also maximizes taste.

Conditioning protocols 610, may include various protocols for cooking or condition nutritional substances 520 based on time, heat, surface temperature of food, different cycles, different conditioning methods, including microwaving, convention, grilling, etc. For instance, it may be noted that for salmon, microwaving is the optimal way to preserve the nutritional value of a piece of salmon as determined by the controller 530 accessing the nutritional data 630 from the database. Other embodiments may use a combination of microwave, convention, grilling or other methods to maximize the nutritional, organoleptic, or aesthetic values desired by the consumer based on the consumer input 620. As described herein, those conditioning protocols may be stored in a database where they can be modified.

Once the conditioner begins conditioning the nutritional substance 520, the attribute sensors 591 may continue provide data regarding sensed attributes 640 of the nutritional substance during cooking. This data may be utilized to further modify the conditioning protocol 610 based on deviations from the expected values. For example, if a piece of salmon is used and an infrared surface temperature attribute sensor 591 detects the salmon surface temperature, once the modified conditioning protocol 660 is determined and implemented, the sensor 591 may continue to detect the surface temperature and compare it to data from the database 550 from prior tests. It may be that this salmon surface temperature rises more quickly, perhaps because although the salmon weighs the same, the salmon is thicker than the tested salmon. Therefore, the modified conditioning protocol 660 may be further modified based on feedback from the sensors in the form of sensed attributes 640. This may be a continuous or periodic feedback loop that allows the various attribute sensors 591 to detect various factors to indicate the progress of cooking and whether the conditioning protocol needs to be modified to account for individual variation. In this case, if the temperature rises faster than expected the overall cooking time or target surface temperature may be decreased appropriately to form a new modified conditioning protocol 660. In other examples, color based sensors may be able to detect changes in food that are associated with being cooked or finished cooking. Accordingly, a combination of visual, temperature, and weight data may be utilized to find the optimal stopping time for when the nutritional substance 520 is finished cooking.

In another embodiment, a conditioning appliance is provided with at least one of a nutritional substance reader 590 and nutritional substance attribute sensors 591, including a weight sensor. In other examples, the physical attributes sensors may include elevation (i.e. GPS), ambient pressure, texture, moisture, relative humidity, color, and other attribute sensors. The conditioning appliance is further provided with the ability to identify specific types of containers, including, but not limited to, plates, bowls, pan, grill, cookware, and so forth. The conditioning appliance may identify such a container by using the nutritional substance reader to identify an identifier on the container unique to that type of container, using an attribute sensor to identify an attribute unique to such a container, or using container detectors to identify unique types of containers, for instance the container may have an RFID tag enabling an RFID reader used as the container detector to identify it. Such a conditioning appliance can be used to determine adaptive conditioning parameters that are responsive to the current nutritional, organoleptic, and aesthetic values of the nutritional substance, consumer input, consumer experience input, and attribute sensor information during conditioning, but are additionally responsive to the specific container being used (for example by subtracting the weight of the specific container from the sensed weight of the nutritional substance 520). In this way, the adaptive conditioning parameters may even account for the physical properties of the container holding the nutritional substance, including, but not limited to, the container's weight, thermal conductivity, and so forth.

In an embodiment of the present invention, conditioner 570 is provided without controller 530 and nutritional substance attribute sensors 591, however it is provided in a format to be compatible with controller 530 and nutritional substance attribute sensors 591. Such a conditioner is also referred to herein as an information and sensing capable conditioner. In contrast, traditional conditioners, also referred to herein as dumb conditioners, are not information and sensing capable, are not compatible with controller 530 and nutritional attribute sensors 591, and accordingly will always be dumb conditioners. As information and sensing enabled conditioning systems according to the present invention are increasingly available, dumb conditioners will become increasingly obsolete.

Information and sensing capable conditioners may be provided in a variety of configurations known to those skilled in the art, and the examples offered herein are for purposed of illustration and not intended to be limiting in any way. In one example of an information and sensing capable conditioner, it is provided with traditional functionality, that is, it will interact with nutritional substances in a traditional fashion. However, the information and sensing capable conditioner is compatible with separately available controller 530 and nutritional substance attribute sensors 591, such that at any time during or after the manufacture and sale of the information and sensing capable conditioner, controller 530 and nutritional substance attribute sensors 591 may be coupled with the information and sensing capable conditioner to enable the full functionality and benefit of conditioner module 500. Information and sensing capable conditioners provide appliance manufacturers and consumers great flexibility, and will not become obsolete like dumb conditioners.

The coupling of controller 530 and nutritional attribute sensors 591 to the information and sensing capable conditioner may take any physical and/or communication format known to those skilled in the art. These may include, but are not limited to: information and sensing capable conditioner provided with Bluetooth, or other wireless near-field communication capability, to communicate with a communication-compatible controller 530, wherein nutritional substance attribute sensors 591 are coupled with, or in communication with, controller 530. The controller 530 may be any of a completely separate unit, an externally attachable unit, and an internally placed unit, while portions of the nutritional substance attribute sensors may be positioned in proximity to, on, or within the conditioner 570, such as in ports or windows provided with the information and sensing capable conditioner; an information and sensing capable conditioner provided with a USB port, or other electrical communication capability, to communicate with a communication-compatible controller 530, wherein nutritional substance attribute sensors 591 are coupled with, or in communication with, controller 530. The controller 530 may be any of a completely separate unit, an externally attachable unit, and an internally placed unit, while portions of the nutritional substance attribute sensors may be positioned in proximity to, on, or within the information and sensing capable conditioner, such as in ports or windows provided with the information and sensing capable conditioner; an information and sensing capable conditioner provided with a fiber optic port, or other optical communication capability, to communicate with a communication-compatible controller 530, wherein nutritional substance attribute sensors 591 are coupled with, or in communication with, controller 530. The controller 530 may be any of a completely separate unit, an externally attachable unit, and an internally placed unit, while portions of the nutritional substance attribute sensors may be positioned in proximity to, on, or within the information and sensing capable conditioner, such as in ports or windows provided with the information and sensing capable conditioner; or an information and sensing capable conditioner provided with WiFi, or other wireless communication capability, to communicate with a WiFi compatible controller 530, wherein nutritional substance attribute sensors 591 are coupled with, or in communication with, controller 530. The controller 530 may be any of a completely separate unit, an externally attachable unit, and an internally placed unit, while portions of the nutritional substance attribute sensors may be positioned in proximity to, on, or within the conditioner 570, such as in ports or windows provided with the information and sensing capable conditioner. It is understood that the controller 530 may be provided with its own consumer interface, may communicate and be operated through the consumer interface provided with the information and sensing capable conditioner, or a combination of both.

For example, an external weight sensor may be provided that may be wirelessly coupled to conditioner 570 or provided any other means of connecting the weight sensor to conditioner 570, for instance, by a USB port. The external weight sensor 591 may take the form of a separate scale that is provided with its own nutritional substance reader 590. Accordingly, the consumer 540 may scan a dynamic information identifier on a nutritional substance 520, and then weigh the nutritional substance on the external weight sensor 591 in order to determine a current $\Delta N$ value of the nutritional substance by reference to a nutritional substance database 550, and/or a nutritional substance attribute library dataset within the database. This external weight sensor 591 may be integrated with any of the various systems disclosed herein and may be utilized at any time to determine a $\Delta N$ value of the nutritional substance 520 that is approximated more precisely based on the actual weight of the substance 520. This may be beneficial to allow a consumer that wishes to consume a portion of a nutritional substance 520 that is prepackaged as a specific size, or a portion that does not fall neatly within a predetermined or pre-calculated serving size of a nutritional substance 520. This external weight sensor may be a freestanding electronic scale or integrated into any other appliance, in order to allow a consumer 540 to retrieve current $\Delta N$ information of a nutritional substance 520, regardless of the portion size the consumer or other entities along the food chain wish to evaluate and/or consumer.

Figure 19:
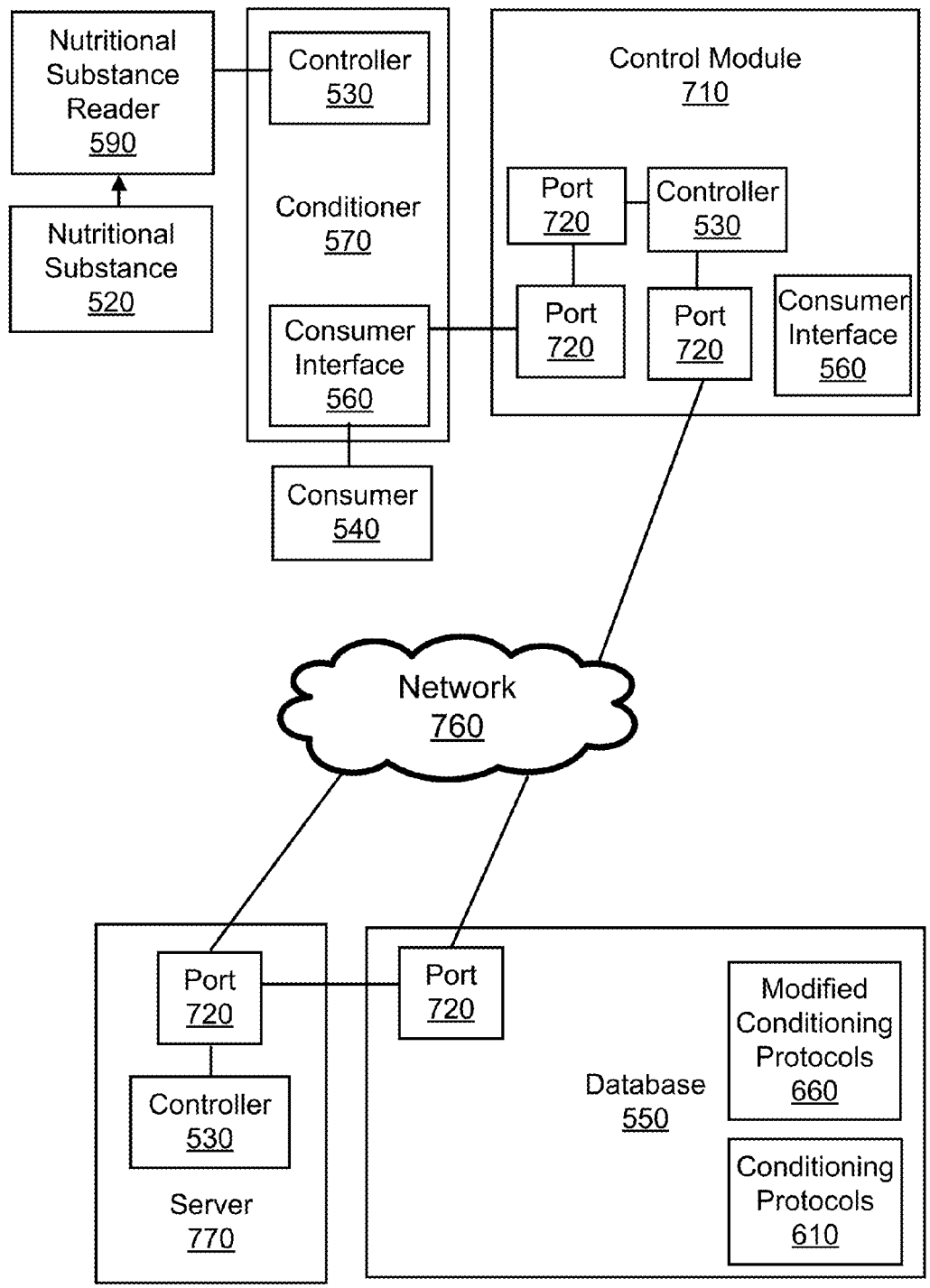
FIG. 19 shows a schematic functional block diagram of a system incorporating a control module according to the present invention.

FIG. 19 is a diagram of a system for providing a database of conditioning protocols 610 referenced to specific nutritional substances 520 that may be accessed remotely by conditioners 570 and updated to provide the most recent recipe information each time the protocol is accessed. For example, nutritional substances 520 may be provided with a dynamic information identifier. This identifier could be referenced to various conditioning protocols 610 in the database 550, so that when a consumer 540 scans the dynamic information identifier on a nutritional substance 520, the appropriate conditioning protocols 610 could be retrieved in order to automatically, or with consumer input, condition the nutritional substance 520. The conditioning protocols 610 could then be updated continuously, when for example, laboratory experimentation showed preferred cooking conditions, or new data on changes in nutritional, organoleptic, or aesthetic values based on the current conditioning protocols 610. This way, a consumer 540 could retrieve the most up to date conditioning protocols 610 by scanning the dynamic information identifier associated with the nutritional substance 520.

FIG. 19 illustrates an example of a control module 710 in communication with a conditioner 570 that may be implemented to coordinate the identification, retrieval, modification, and implementation of conditioning protocols 610 for conditioning a particular nutritional substance 520. The control module 710 may have various controllers 530 and/or control systems to coordinate the retrieval and sending of data, and the potential modification of conditioning protocols 610. The control module 710 may have ports 720 that interface and provide communication with the conditioner 570 and a remote (or local) server 770 and recipe database 550 over a network 760. When a consumer 540 scans a dynamic information identifier of a nutritional substance 510 with a nutritional substance reader 590 or otherwise provides information to identify the nutritional substance 510, that information may be sent to the control module 710. The control module 710 may then coordinate the retrieval of an appropriate conditioning protocol for the nutritional substance 520 from the database 550. Then, once the protocol 610 is retrieved, the control module 710 may then coordinate conditioning of the nutritional substance 520 by the conditioner 570.

The control module 710 may contain various ports 720 to interface with the conditioner 570, network 760, server 770, and other components of the system in order to transfer information. Ports 720 may be physical ports, including data connections such as any RS-232 ports, RS-423, RS-485, serial ports, parallel ports, Ethernet, firewall, USB, Mini, PCI, Serial ATA, FireWire, and other various other suitable ports. In some embodiments, ports 720 may be software ports (i.e. virtual ports) for receiving communications from the various components of the system based on various appropriate protocols, including RS-232. The ports 720 may include ports for receiving and requesting conditioning protocols 610 from the server 770 and database 550, ports for communicating with the conditioner 570, and ports for receiving consumer input. In some embodiments, the various ports 720 may be combined and receive input from more than one component of the system. For example, the control module may include an input port or first port for receiving information related to a dynamic information identifier provided with a nutritional substance. Additionally, the control module may include a second port in communication with the database 550 with information referenced to dynamic information identifiers. Furthermore, the control module 710 may also include a third port 720 for receiving consumer input.

The control module 710 may contain various forms of memory to locally store conditioning protocols 610 for easier access when a network 760 connection is not functioning or for faster access. The control module 710 may also contain software for updating conditioning protocols 610 to appropriately format for execution by an associated conditioner 570. This may include the ability to load software for each particular conditioner 570 associated with the control module 710.

The recipe database 550 and server 770 may be a centrally located system that provides access to conditioning protocols 610 and modified condition protocols 660 that are referenced to particular nutritional substances 520 and/or an associated dynamic information identifier(s). The database 550 may contain information referenced to dynamic information identifiers that identify a particular nutritional substance 520. For example, each dynamic information identifier may be referenced or assigned to a particular conditioning protocol 610 or numerous conditioning protocols 610 and/or modified condition protocols 660. Additionally, various other information may be associated with each conditioning protocol 610 or 660 in the database 550, including data relating to changes in nutritional, organoleptic, and/or aesthetic values of a particular nutritional substance 520 that is subject to the particular conditioning protocol 610 as described herein.

Control modules 710 attached to conditioners 570 will then be able to retrieve the most up to date conditioning protocols 610 that are referenced to a particular nutritional substance 520 or dynamic information identifier. The database 550 may be easily updatable to change various aspects of the conditioning protocols 610 referenced to certain dynamic information identifiers and to update the conditioning protocols 610 to create modified conditioning protocols 660. These modified conditioning protocols 660 may then be referenced to the same dynamic information identifiers so the modified conditioning protocol 660 may be retrieved instead of the original conditioning protocol 610. A control module's request for a conditioning protocol 610 referenced to that dynamic information identifier would be returned with the modified conditioning protocol 660.

The control module 710 may then send a retrieved or modified condition protocol 710 to the conditioner 570 for implementation to condition the nutritional substance 520. In some embodiments, the control module 710 may directly control or send control instructions to the conditioner 570 to operate its heating and other conditioning elements appropriately, or may send the condition protocol(s) 610 for implementation by a controller 530 associated with the conditioner 540.

The control module 710 may utilize methods for accessing and implementing appropriate condition protocols 610. For example, a consumer 540 may unpack a nutritional substance 520 that the consumer 540 would like to condition. The consumer 540 may then scan a dynamic information identifier associated with the nutritional substance 520 with the nutritional substance reader 590, or enter identifying information in the consumer interface 560.

This information may be entered into a consumer interface 560 on the conditioner or optionally a consumer interface 560 on or connected to the control module 710. This information may then be sent to the control module 710. The control module 710 may then send a request for a condition protocol 610 to the server 770. Once receiving the request, the server's 770 controller 530 may then process the identifying data, and use it to access the database 550 and select conditioning protocols 610 that are appropriate. Then, the server 770 may create a response to the request for condition protocol 610 that includes the appropriate protocols 610 identified from the database 550, and send the protocols back to the control module 710 over the network 760.

The control module 710 may then either send the conditioning protocols 610 to the conditioner 570 or display the various options to the consumer 540 on its own consumer interface 560. Then the consumer 540 may select the condition protocol 610 it desires and enter any preferences for the particular conditioning protocol 610 that may be modifiable. Once this information is entered, the control module 710 (or in some embodiments, the conditioner 570 and/or the server 770) may process the condition protocol 610 and the parameters for the consumer 540 input to create a conditioning protocol 610 that is executable by the conditioner 570. This may be created by modifying the selected and uploaded condition protocol from the database 550.

It is understood that nutritional substance attribute sensors according to the present inventions, can beneficially be provided with, or combined with, other nutritional substance modules, including transformation, preservation, and consumer modules. For example, the nutritional substance attribute sensors could be provided with the local storage environments, containers, and coupons described herein. Nutritional substance attribute sensors, or at least a portion of the nutritional substance attribute sensor, could be provided with or incorporated into the package of any prepackaged nutritional substance, such that a consumer may interrogate the package without disrupting its integrity to obtain information related to a nutritional, organoleptic, or aesthetic value of the nutritional substance contained therein. Further, nutritional substance attribute sensors, or at least a portion of the nutritional substance attribute sensor, could be provided with, coupled to, or incorporated into smartphones. This would enable a wide array of users and scenarios wherein nutritional substances can be identified and their current nutritional, organoleptic, and aesthetic state can be determined.

Unless the context clearly requires otherwise, throughout the description and the claims, the words "comprise," "comprising," and the like are to be construed in an inclusive sense (i.e., to say, in the sense of "including, but not limited to"), as opposed to an exclusive or exhaustive sense. As used herein, the terms "connected," "coupled," or any variant thereof means any connection or coupling, either direct or indirect, between two or more elements. Such a coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. While processes or blocks are presented in a given order in this application, alternative implementations may perform routines having steps performed in a different order, or employ systems having blocks in a different order. Some processes or blocks may be deleted, moved, added, subdivided, combined, and/or modified to provide alternative or sub-combinations. Also, while processes or blocks are at times shown as being performed in series, these processes or blocks may instead be performed or implemented in parallel, or may be performed at different times. Further any specific numbers noted herein are only examples. It is understood that alternative implementations may employ differing values or ranges.

The various illustrations and teachings provided herein can also be applied to systems other than the system described above. The elements and acts of the various examples described above can be combined to provide further implementations of the invention.

Any patents and applications and other references noted above, including any that may be listed in accompanying filing papers, are incorporated herein by reference. Aspects of the invention can be modified, if necessary, to employ the systems, functions, and concepts included in such references to provide further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

While certain aspects of the invention are presented below in certain claim forms, the applicant contemplates the various aspects of the invention in any number of claim forms. For example, while only one aspect of the invention is recited as a means-plus-function claim under 35 U.S.C. §112, sixth paragraph, other aspects may likewise be embodied as a means-plus-function claim, or in other forms, such as being embodied in a computer-readable medium. Any claims intended to be treated under 35 U.S.C. §112, ¶6 will begin with the words "means for." Accordingly, the applicant reserves the right to add additional claims after filing the application to pursue such additional claim forms for other aspects of the invention.

The invention claimed is:

1. A dynamic control module for a conditioning system for nutritional substances comprising:
   a first port for receiving information related to a dynamic information identifier provided with a nutritional substance;
   a second port in communication with a database with information referenced to the dynamic information identifier, the database including various conditioning protocols for the nutritional substance that may be modified to create various modified conditioning protocols stored in the database and referenced to the same nutritional substance, wherein the conditioning protocols and modified conditioning protocols include instructions that modify the conditioning protocol based on feedback from a nutritional substance attribute sensor during conditioning;

a third port for receiving consumer input; and a controller configured to send a request to the database for at least one of the modified conditioning protocols after receiving the information related to the dynamic information identifier of the nutritional substance, and further configured to output a final conditioning protocol based on the at least one modified conditioning protocol received from the data base and the consumer input, wherein the final conditioning protocol contains instructions executable by a control system of a conditioner.

2. The system of claim 1, wherein the controller is configured to further modify the modified conditioning protocol so that it is compatible with the conditioner before outputting the final conditioning protocol.

3. The system of claim 1, wherein the dynamic control module is integrated with the conditioner.

4. The system of claim 1, wherein the first port and second port both transmit data over the same conductors.

5. The system of claim 1, wherein the database additionally contains ΔN information associated with the various conditioning protocols.

6. The system of claim 1, wherein the conditioning protocols are comprised of a hierarchy of conditioning protocols.

7. The system of claim 6, wherein the hierarchy includes nodes that branch to specific conditioning protocols based on consumer input.

8. The system of claim 6, wherein the hierarchy includes nodes that branch to specific conditioning protocols based on information relating to a type of conditioner.

9. The system of claim 1, wherein the condition protocols include contingent instructions that require consumer input.

10. The system of claim 1, wherein the dynamic condition protocols that may be modified include data values representing various conditioning instructions that may be modified to alter the conditioning temperature.

11. The system of claim 1, wherein the dynamic condition protocols that may be modified include data values representing various conditioning instructions that may be modified to alter the conditioning time.

12. A system for providing dynamic conditioning protocols to conditioners for nutritional substances comprising:

an input port configured to receive information regarding a nutritional substance;

a library comprising conditioning protocols referenced to known nutritional substances, wherein the conditioning protocols are able to be modified and stored in the library as modified conditioning protocols referenced to the same known nutritional substances, wherein the conditioning protocols and modified conditioning protocols include instructions that modify the conditioning protocol based on feedback from a nutritional substance attribute sensor during conditioning;

a controller configured to compare the information regarding the nutritional substance with the modified conditioning protocols to determine at least one matching modified conditioning protocol for conditioning the nutritional substance and to send the modified conditioning protocol to a conditioner, wherein the modified conditioning protocol sent to the conditioner contains instructions executable by a control system of the conditioner.

13. The system of claim 12, wherein the input port additionally receives information regarding a type of conditioner.

14. The system of claim 13, wherein the controller determines a modified conditioning protocol based additionally on the information regarding the type of conditioner.

15. The system of claim 13, wherein the input port additionally receives data representing consumer input.

16. The system of claim 15, wherein the controller determines a matching modified conditioning protocol additionally based on the consumer input.

17. The system of claim 12, wherein the controller is incorporated in a server.

18. The system of claim 12, wherein the conditioning protocols are additionally referenced to ΔN information.

19. A method for providing an updated conditioning protocol for conditioning a nutritional substance, the method comprising:

updating various conditioning protocols in a database of conditioning protocols referenced to known nutritional substances, wherein the conditioning protocols include instructions that modify the conditioning protocol based on feedback from a nutritional substance attribute sensor during conditioning;

accessing at least one of the updated conditioning protocols in the database referenced to known nutritional substances;

receiving consumer input regarding preferences for conditioning; and adapting a final conditioning protocol for the nutritional substance based at least on the updated conditioning protocol and the consumer input, wherein the final conditioning protocol contains instructions executable by a control system of a conditioner.

20. The method of claim 19, wherein the conditioning protocols are referenced to ΔN information in the database.

21. The method of claim 19, wherein the conditioning protocol is additionally adapted based on the ΔN information.

22. The method of claim 19, wherein the ΔN is historical information.

23. The method of claim 19, wherein the accessed updated conditioning protocol is first selected to be accessed based on the consumer input.

24. The method of claim 19, wherein the accessed updated conditioning protocol is first selected to be accessed based on information relating to a conditioner in communication with the system.

25. The method of claim 19, wherein the ΔN is an estimated value.

26. The method of claim 19, wherein the updating includes changing a temperature of the conditioning protocol.

27. The method of claim 19, wherein the updating includes changing a time of the conditioning protocol.

* * * * *